US009756863B2

(12) United States Patent
Puopolo et al.

(10) Patent No.: US 9,756,863 B2
(45) Date of Patent: Sep. 12, 2017

(54) BACTERIAL *LYSOBACTER CAPSICI* STRAIN AND USES THEREOF

(71) Applicant: Fondazione Edmund Mach, S. Michele all'Adige (IT)

(72) Inventors: Gerardo Puopolo, Nocera Superiore (IT); Ilaria Pertot, Tesero (IT)

(73) Assignee: Fondazione Edmund Mach, S. Michele all'Adige (IT)

( * ) Notice: Subject to any disclaimer, the term of this patent is extended or adjusted under 35 U.S.C. 154(b) by 0 days.

(21) Appl. No.: 14/785,541

(22) PCT Filed: Apr. 22, 2014

(86) PCT No.: PCT/EP2014/058151
§ 371 (c)(1),
(2) Date: Oct. 19, 2015

(87) PCT Pub. No.: WO2014/173906
PCT Pub. Date: Oct. 30, 2014

(65) Prior Publication Data

US 2016/0081350 A1 Mar. 24, 2016

(30) Foreign Application Priority Data

Apr. 22, 2013 (EP) .................................... 13164716

(51) Int. Cl.

| | |
|---|---|
| ***A01N 59/20*** | (2006.01) |
| ***C12N 1/20*** | (2006.01) |
| ***A01N 63/00*** | (2006.01) |
| ***C12R 1/64*** | (2006.01) |
| ***C12R 1/01*** | (2006.01) |

(52) U.S. Cl.
CPC ............ *A01N 63/00* (2013.01); *A01N 59/20* (2013.01); *C12N 1/20* (2013.01); *C12R 1/01* (2013.01); *C12R 1/64* (2013.01)

(58) Field of Classification Search
None
See application file for complete search history.

(56) References Cited

U.S. PATENT DOCUMENTS 5,116,825 A * 5/1992 Malras .................. A01N 59/20 514/231.2
2008/0148432 A1 6/2008 Abad
2009/0183270 A1 7/2009 Adams et al.

OTHER PUBLICATIONS

Haywood, AC; et al; "Stenotrophomonas and Lysobacter: ubiquitous plant-associated gamma-proteobacteria of developing significance in applied microbiology" Journal of Applied Microbiology, 108, 756-770, 2010.*

Hayward, AC; et al; "Stenotrophomonas and Lysobacter: ubiquitous plant-associated gamma-proteobacteria of developing significance in applied microbiology" Journal of Applied Microbiology, 108, 756-770, 2009.*

Narayanasamy, P; "Detection and Identification of Bacterial Biological Control Agents" Biological Management of Diseases of Crops, 15, 201-293, 2013.*

Puopolo, G; et al; "Lysobacter capsici AZ78 produces cyclo(L-Pr o-L-Tyr), a 2,5-diketopiperazine with toxic ac tivity against sporangia of Phytophthora infestans and Plasmopara viticola" Journal of Applied Microbiology, 117, 1168-1180, 2014.*

Park, Joo Hwang; et al; "Lysobacter capsici sp. nov., with antimicrobial activity, isolated from the rhizosphere of pepper, and emended description of the genus *Lysobacter*" International Journal of Systematic and Evolutionary Microbiology, 58, 387-392, 2008.*

Arguello et al., "The structure and function of heavy metal transport P1B-ATPases." Biometals. 20(3-4):233-48 (2007).

Banin et al., "Iron and Pseudomonas aeruginosa biofilm formation." Proc Natl Acad Sci USA. 102(31):11076-81 (2005).

Christensen et al., "*Lysobacter*, a new genus of nonfruiting, gliding bacteria with a high base ratio." Int J Syst Bacteriol. 28(3):367-93 (1978).

Cooksey, "Molecular mechanisms of copper resistance and accumulation in bacteria." FEMS Microbiol Rev. 14:381-6 (1994).

Cooley et al., "Colonization of *Arabidopsis thaliana* with *Salmonella enterica* and enterohemorrhagic *Escherichia coli* O157:H7 and competition by *Enterobacter asburiae*." Appl Environ Microbiol. 69(8):4915-26 (2003).

Dagostin et al., "Are there alternatives to copper for controlling grapevine downy mildew in organic viticulture?" Crop Prot. 30(7):776-88 (2011).

De la Iglesia et al., "Novel polymerase chain reaction primers for the specific detection of bacterial copper P-type ATPases gene sequences in environmental isolates and metagenomic DNA." Lett Appl Microbiol. 50(6):552-62 (2010).

De Souza et al., "Biochemical, genetic and zoosporicidal properties of cyclic lipopeptide surfactants produced by *Pseudomonas fluorescens*." App Environ Microbiol. 69(12):7161-72 (2003).

Dulla et al., "Quorum size of *Pseudomonas syringae* is small and dictated by water availability on the leaf surface." Proc Natl Acad Sci USA. 105(8):3082-7 (2008).

Elasri et al., "Study of the response of a biofilm bacterial community to UV radiation." Appl Environ Microbiol. 65(5):2025-31 (1999).

EPPO. EPPO Standards PP1/31(3). Efficacy evaluation of fungicides & bactericides. 2004; 2:47-49.

Folman et al., "Ecophysiological characterization of rhizosphere bacterial communities at different root locations and plant developmental stages of cucumber grown on rockwool." Microbial Ecol. 42(4):586-97 (2001).

(Continued)

*Primary Examiner* — David Berke-Schlessel
(74) *Attorney, Agent, or Firm* — Clark & Elbing LLP; Kristina Bicker-Brady

(57) ABSTRACT

The present invention relates to a novel bacterial strain belonging to *Lysobacter capsici* species, *Lysobacter capsici* AZ78, bacteria of said bacterial strain, and bacterial preparations related thereto, as well as to uses of the above for preparing a plant protection product—as well as to plant protection products comprising any of the above as well as to further related uses and methods.

11 Claims, 17 Drawing Sheets

(56) References Cited

OTHER PUBLICATIONS

Figure 1:
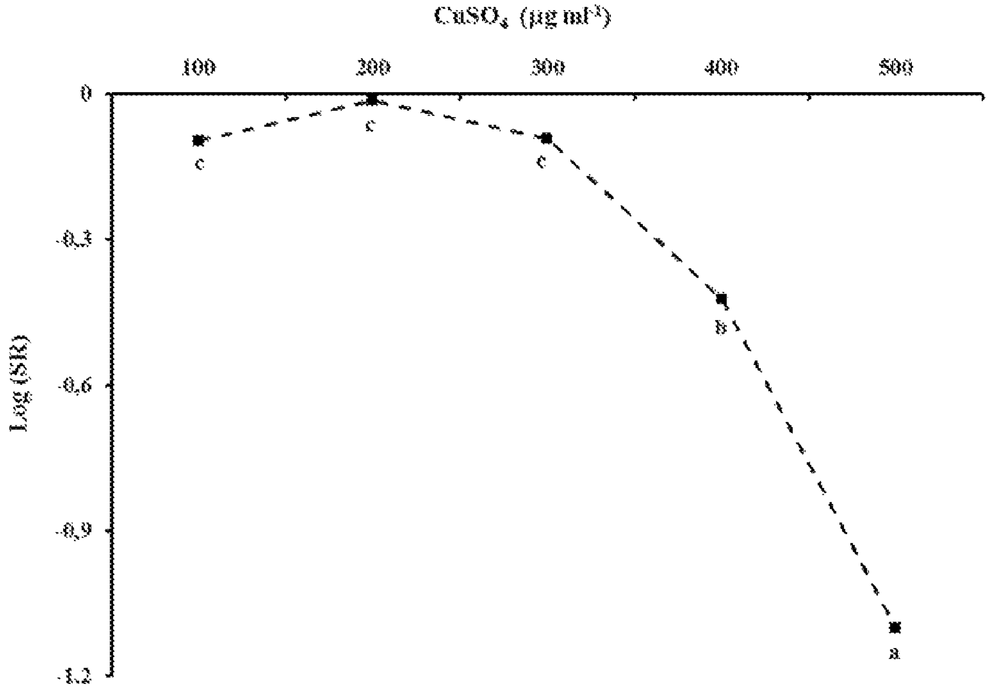

Folman et al., "Characterisation of *Lysobacter enzymogenes* (Christensen and Cook 1978) strain 3.1T8, a powerful antagonist of fungal diseases of cucumber." Microbiol Res. 158(2):107-15 (2003).
Folman et al., "Production of antifungal compounds by *Lysobacter enzymogenes* isolate 3.1T8 under different conditions in relation to its efficacy as a biocontrol agent of *Pythium aphanidermatum* in cucumber." Biol Control. 31(2):145-154 (2004).
Fry et al., "Resurgence of the Irish potato famine fungus." Bioscience 47(6):363-71 (1997).
Fu et al., "Sequence, mapping and disruption of CCC2, a gene that cross-complements the Ca(2+)-sensitive phenotype of csg1 mutants and encodes a P-type ATPase belonging to the Cu(2+)-ATPase subfamily." Yeast. 11:283-92 (1995).
Ge et al., "Nucleotide sequence and mutational analysis indicate that two *Helicobacter pylori* genes encode a P-type ATPase and cation-binding protein associated with copper transport." Mol Microbiol. 15:97-106 (1995).
Gessler et al., "*Plasmopara viticola*: a review of knowledge on downy mildew of grapevine and effective disease management." Phytopathol Mediterr. 50:3-44 (2011).
Giesler et al., "Evaluation of *Stenotrophomonas maltophilia* strain C3 for biocontrol of brown patch disease." Crop Prot. 17(6):509-13 (1998).
Hayward et al., "*Stenotrophomonas* and *Lysobacter*: ubiquitous plant-associated gamma-proteobacteria of developing significance in applied microbiology." J App Microbiol. 108:756-70 (2010).
Homma et al., "Suppression of sugar beet damping-off and production of antagonistic substances by strains of rhizobacteria." Ann Phytopathol Soc Jpn. 59(3):282 (1993).
Islam et al., "Suppression of damping-off disease in host plants by rhizoplane bacterium *Lysobacter* sp. strain SB-K88 is linked to plant colonization and antibiosis against soilborne peronosporomycetes." Appl Environ Microbiol. 71(7):3786-96 (2005).
Jochum et al., "Fusarium head blight biological control with *Lysobacter enzymogenes* strain C3." Biol Control. 39:336-44 (2006).
Kilic-Ekici et al., "Induced resistance as a mechanism of biological control by *Lysobacter enzymogenes* strain C3." Phytopathology. 93:1103-10 (2003).
King et al., "Two simple media for the demonstration of pyocyanin and fluorescin." J Lab Clin Med. 44:301-7 (1954).
Kobayashi et al., "The role of clp-regulated factors in antagonism against *Magnaporthe poae* and biological control of summer patch disease of Kentucky bluegrass by *Lysobacter enzymogenes* C3." Can J Microbiol. 51:719-23 (2005).
Leben, "Relative humidity and the survival of epiphytic bacteria with buds and leaves of cucumber plants." Phytopathology. 78(2):179-85 (1988).
Lejon et al., "Fingerprinting and diversity of bacterial copA genes in response to soil types, soil organic status and copper contamination." FEMS Microbiol Ecol. 61:424-37 (2007).
Lourenço et al., "Biocontrol of tomato late blight with combination of epiphytic antagonists and rhizobacteria." Biol Control. 38:331-40 (2006).
Lugtenberg et al., "Plant-growth-promoting rhizobacteria." Annu Rev Microbiol. 63:541-56 (2009).
Maddula et al., "Quorum sensing and phenazines are involved in biofilm formation by *Pseudomonas chlororaphis* (aureofaciens) strain 30-84." Microb Ecol. 52:289-301 (2006).
Mizubuti et al., "Management of late blight with alternative products." Pest Technology. 1(2):106-16 (2007).
Morris et al., "Methods for observing microbial biofilms directly on leaf surfaces and recovering them for isolation of culturable microorganisms." Appl Environ Microbiol. 63(4):1570-6 (1997).
Nakayama et al., "Possible role of xanthobaccins produced by *Stenotrophomonas* sp. strain SB-K88 in suppression of sugar beet damping-off disease." Appl Environ Microbiol. 65(10):4334-9 (1999).
Ophir et al., "A role for exopolysaccharides in the protection of microorganisms from desiccation." Appl Environ Microbiol. 60(2):740-5 (1994).
Park et al., "*Lysobacter capsici* sp. nov., with antimicrobial activity, isolated from the rhizosphere of pepper, and emended description of the genus *Lysobacter*." Int J Syst Evol Microbiol. 58:387-92 (2008).
Pavissich et al., "Sulfate reduction, molecular diversity, and copper amendment effects in bacterial communities enriched from sediments exposed to copper mining residues." Environ Toxicol Chem. 29(2):256-64 (2010).
Perrot et al., "Gel immobilization improves survival of *Escherichia coli* under temperature stress in nutrient-poor natural water." Water Res. 32(12):3521-6 (1998).
Petersen et al., "Control of copper homeostasis in *Escherichia coli* by a P-type ATPase, CopA and a MerR-like transcriptional activator, CopR." Gene. 261:289-98 (2000).
Postma et al., "Soil suppressiveness and functional diversity of the soil microflora in organic farming systems." Soil Biol Biochem. 40:2394-406 (2008) (13 pages).
Puopolo et al., "Identification and characterization of *Lysobacter capsici* strain PG4: a new plant health promoting rhizobacterium." J Plant Path. 92(1):157-64 (2010).
Rensing et al., "*Escherichia coli* mechanisms of copper homeostasis in a changing environment." FEMS Microbiol Rev. 27:197-213 (2003).
Ritchie et al., "Copper- and streptomycin-resistant strains and host differentiated races of *Xanthomonas campestris* pv. *vesicatoria* in North Carolina." Plant Dis. 75:733-736 (1991).
Rondon et al., "Biocontrol and root colonization by the gliding bacterium *Lysobacter antibioticus*." Phytopathology. 89:S66 (1999).
Stockwell et al., "The sigma factor RpoS is required for stress tolerance and environmental fitness of *Pseudomonas fluorescens* Pf-5," Microbiology. 151:3001-9 (2005).
Stockwell et al., "Role of RpoS in stress tolerance and environmental fitness of the phyllosphere bacterium *Pseudomonas fluorescens* strain 122," Phytopathology. 99(6):689-95 (2009).
Sundin et al., "Ultraviolet radiation (UVR) sensitivity analysis and UVR survival strategies of a bacterial community from the phyllosphere of field-grown peanut (*Arachis hypogeae* L.)," Microb Ecol. 38:27-38 (1999).
Tilcher et al., "Effects of microbial antagonists on leaf infestation, sporangia germination and zoospore behaviour of *Plasmopara viticola* (Berk. & Curtis) Berl. & de Toni," Med. Fac. Landbouww. Univ. Gent. 59:919-29 (1994).
Tilcher et al., "About the use of antagonistic bacteria and fungi." In: Boos M, editor. *10th International Conference on Cultivation Technique and Phytopathological Problems in Organic Fruit-Growing and Viticulture. Proceedings to the Conference* from Feb. 4, to 7, 2002 at Weinsberg/Germany 2002. 142-5 (2002).
Tomaras et al., "Attachment to and biofilm formation on abiotic surfaces by *Acinetobacter baumannii*: involvement of a novel chaperone-usher pili assembly system," Microbiology. 149:3473-84 (2003).
Wilson et al., "Location and survival of leaf-associated bacteria in relation to pathogenicity and potential for growth within the leaf," Appl Environ Microbiol. 65(4):1435-43 (1999).
Wong et al., "Heterothallism in *Plasmopara viticola*," Plant Pathol. 50:427-32 (2001).
Zakharchenko et al., "Effect of rhizosphere bacteria *Pseudomonas aureofaciens* on the resistance of micropropagated plants to phytopathogens," Appl Biochem Microbiol. 47(7):661-6 (2011).

* cited by examiner

| Untreated grapevine plant challenged with *Plasmopara viticola* | AZ78-treated grapevine plant inoculated with *Plasmopara viticola* |
|---|---|
|  |  |

| Untreated tomato plant challenged with *Phytophthora infestans* | AZ78-treated tomato plant inoculated with *Phytophthora infestans* |
|---|---|
|  |  |

FIG. 8A

**> *Lysobacter capsici* AZ78 gene *ctp*A, 2415 bp** (SEQ ID NO: 1)

ATGACCTGCAGCTCCTGCGTCGGCCGCATCGAGCGGGCCGTGTCCGCCCTGCCCGGCGTCGCCGAGGTCAGCG
TCAATCTGGCCACCGAAATCGCCGAGGTCGCCCACGACGCCAGCGTCTCCGCCGCGCAGATCGAACGCGCCAT
CGCCGCCGCCGGTTACAGCGTCCCCAGCGAGGAGCTCGTGCTGGCGCTGCGCGGATGAATTGCGGCTCCTGC
GTCGGCCGGATCGAGAAGGCGCTCACCGCGGTGCCGGGCGTGCTCGAGGCCTCGGTCAATCTGGCCACCGAGC
GCGCCAGGCTGCGCATGCTCGAAGGCACCGACACGGCCGCGCTGATCGCCGCAGTCAAGCGCGCCGGTTACGA
AGCGAGCCTGCCCGACAGCGATCCCGACAACCCGTCCGGCGGCGGCGCAAGCAGCGCATCCGCTGGCGACAGC
TCGCACGCGCCGCGTACCGACAGCGGCATCGCCACCGCCGCCGCCCACGGCAACGCCAAGCCCGCGCTGACGC
GCGAAACCCGCCATCTGCTGATCGCCGCCGCGCTGTCGCTGCCCTTGGTCGCGCCGATGCTCGGCCTGTTGTT
CGGTCAGCACTGGATGCTGCCGGGCTGGCTGCAGTTCGCCCTGGCCACGCCGGTGCAGTTCTGGCTCGGCGCG
CGCTTTTATCGCGCCGGCTGGAGCGCACTGCGCGCGCGCAGCGGCAACATGGACCTGCTGGTCGCGCTCGGCA
GCAGCGCCGGTTACGGCCTGAGCCTGTACCACCTGCTGCGCGGCGATCAGATGCAGCTGTATTTCGAAACCTC
GGCGGTGATCGTCACCCTGATCCTGTTCGGCAAATGGCTGGAAGCGCGCGCCAAGCGCCAGACCACCGCGGCG
ATCCGCGCCCTGCAGGCGCTGCGCCCGAGCAGCGCGCGGGTGCTGCGCGACGGCGTCGAACACGAACTGCCGC
TGGCGCAGTTGCGGGTCGGCGACCTCGTGGTGGTGCGTCCGGGCGAACGCCTGCCGGCCGACGGCCGCATCGT
CGAAGGCCTCACCCACGTCGACGAATCCCTGCTCACCGGCGAATCCCTGCCGGTCGCGCGCGAGCGCGGCGAC
CGCGTCACCGGCGGCGCGATCAACGGCGAAGGCCGCATCGTGGTCGAGACCGTGGCGGTCGGCGCGGAGAGCG
CGCTCGCCCGCATCATCCGTCTGGTCGAGGACGCGCAGGCCAAGAAGGCGCCGATCCAGCACTTGGTCGACCG
GGTCAGCGCGGTGTTCGTGCCGGTGGTGATCGCGATCGCGCTGCTGACCCTGATCGGCTGGGGCCTGTATGCC
GGCGACTGGAGCCAGGCCGTGCTCAACGCGGTCGCGGTGCTGGTGATCGCCTGTCCGTGCGCGCTGGGCCTGG
CCACGCCGACCGCGATCATGGCCGGCACCGGCGTGGCCGCGCGCGCGGGCATTCTGATCAAGGACGCCGAAGC
GCTGGAAATCGCGCATCGAATCGACGTGGTCGCGTTCGACAAGACCGGCACCCTGACCGAAGGCAAGCCGGTG
CTGAGCGAATGGACCGCGCTCGACGGCGACCGCGACGCACTGCTGCGCTTCGCCGCGGCGCTGCAATCGGGCA
GCGAGCATCCGCTGGCCCGCGCCACCCTCGACGCGGCGCGCGCGCTGAGCCTGCCGCCGGTGTCGCAATTGCA
GGCGCTGGCCGGACGCGGCCTGCGCGGCGAGGTCGAAGGCCGCAACCTGCTGCTCGGCAGCACCCGCATGCTC
GAAGAAGCCGGCGTCGATCTGCAACCACTGCGCGAGGCGGCGCAGCGCCTGGCCGACAGCGGCCACAGCGTAT
CGTGGCTGGCGCGCGACGGCGCCGACGGCGCGCAGTTGCTCGGCCTGCTCGGCTTCCGCGATACCCCGCGCGC
CAACGCCCGCGCGGCGATCGAACGCCTGCATGCATTGGGTGTGAGCACCGCGATGATCTCCGGCGATCACATC
GGCGCAGCGCGCGCGGTCGCCGCCGAACTCGGCATCGACCAGATCCGCGCCGACGTATTGCCCGAACAGAAGG
CCGCCGCGGTCGCCGAACTCGGCCAGTTCCGCACCGTGGCGATGGTCGGCGACGGTGTCAACGACGCGCCGGC
GCTGGCCGCGGCCGATGTCGGCATCGCCATGGGCAGCGGCACCGACGTGGCGATGCAGGCCGCCGGCATCACC
CTGATGCGCGCCGAGCCGGGACTGGTCGCCGACGCGATCGAAATCTCGCGCCGCACCAGCCGCAAGATCCGCC
AGAACCTGTTCTGGGCGTTCGGCTACAACGTGATCGGCATCGGCCTGGCGACCTTGGGCTGGTTGAACCCGGT
GGTCGCCGCCGCGGCGATGGCCTTCTCCAGCGTCAGCGTGATCGGCAACACTCTGCTGCTGCGCCGCTGGAAA
CCGGCA

FIG. 8B

**> *Lysobacter capsici* AZ78 Copper-translocating P-type ATPase A** (SEQ ID NO: 2)

MTCSSCVGRIERAVSALPGVAEVSVNLATEIAEVAHDASVSAAQIERAIAAAGYSVPSEELVLALRGMNCGSC
VGRIEKALTAVPGVLEASVNLATERARLRMLEGTDTAALIAAVKRAGYEASLPDSDPDNPSGGGASSASAGDS
SHAPRTDSGIATAAAHGNAKPALTRETRHLLIAAALSLPLVAPMLGLLFGQHWMLPGWLQFALATPVQFWLGA
RFYRAGWSALRARSGNMDLLVALGSSAGYGLSLYHLLRGDQMQLYFETSAVIVTLILFGKWLEARAKRQTTAA
IRALQALRPSSARVLRDGVEHELPLAQLRVGDLVVVRPGERLPADGRIVEGLTHVDESLLTGESLPVARERGD
RVTGGAINGEGRIVVETVAVGAESALARIIRLVEDAQAKKAPIQHLVDRVSAVFVPVVIAIALLTLIGWGLYA
GDWSQAVLNAVAVLVIACPCALGLATPTAIMAGTGVAARAGILIKDAEALEIAHRIDVVAFDKTGTLTEGKPV
LSEWTALDGDRDALLRFAAALQSGSEHPLARATLDAARALSLPPVSQLQALAGRGLRGEVEGRNLLLGSTRML
EEAGVDLQPLREAAQRLADSGHSVSWLARDGADGAQLLGLLGFRDTPRANARAAIERLHALGVSTAMISGDHI
GAARAVAAELGIDQIRADVLPEQKAAAVAELGQFRTVAMVGDGVNDAPALAAADVGIAMGSGTDVAMQAAGIT
LMRAEPGLVADAIEISRRTSRKIRQNLFWAFGYNVIGIGLATLGWLNPVVAAAAMAFSSVSVIGNTLLLRRWK
PA

FIG. 8C

**> *Lysobacter capsici* AZ78 gene *copA*, 1800 bp** (SEQ ID NO: 3)

ATGAACAGATTTTTCTCCGACGACGGCGGCGCATCGATCGATGCCGGCCGTCGCCGTTTCGTCACCGGCCTGG
CGGTCGGCGGCCTAGCCGCAGGCAGCGGCCTGTGGCGTTCGGCCTATGCCGCGCCCGCGCTGGCCGGTGCGCC
GCAGGTATTGAGCGGGACCGAATTCGATCTCTCGATCGGCTCGTCGCTGGCCAACTTCACCGGCAAGACGCGC
CCGGCGATCACCGTCAACGGCAGCCTGCCCGCGCCGATCCTGCGCTGGCGCGAAGGCGATACGGTGACCTTGC
GGGTCGCCAACCGGCTCGCCGAAGGCATGAGCTCGATCCATTGGCACGGCCTGATCCTGCCGGCCAACATGGA
CGGCGTGCCGGGCCTGAGCTTCGACGGCATCCATCCGGGCGAAAGCTACGTGTACCGCTTCCGGGTCGGGCAG
TCGGGCACGTACTGGTATCACAGCCATTCGATGTTCCAGGAACAGGCCGGGCTGTACGGCGCGATCGTGATCG
ATCCGCGCGAACCGGCGCCGTTCCACTTCGATCGCGAGCATGTGCTGCTGCTGTCGGACTGGACCGACATGGA
CCCGGCGGCGCTGTTCCGGCGCCTGAAAAAGATGTCGAGTTACGACAACTACGCCAAGCGCACGGTCGGCGAT
TTCATGCGCGACGCGCGCGAACGCGGGCTGGCCGCGACCCTGCGCGATCGCGGCGAATGGGGCCGCATGCGCA
TGACCCCGACCGATCTGTCCGACGTCAACGGCAACACCTACACCTACCTGCTCAACGGCGCCGCGCCGGCCGG
CAACTGGACCGGGCTGTTCCGTCCGGGCGAAAAGGTGTTGCTGCGTTTCATCAACGGCTCGGCGATGACCTAC
TTCGACGTGCGCATTCCCGGTTTGAAGATGACCGTGGTCGCCGCCGACGGCCAGTACATCCATCCGGTCACGG
TCGACGAATTCCGCATCGCGGTGGCCGAAACCTTCGACGTGCTGGTCGAACCGGCCGGCCAGGACGCGTACAC
CATCTTCGCCCAGGACAACGGCCGCACCGGCCATGCGCGCGGCACCCTGGCGGTGCGCGAAGGCCTGCAGGCC
GAGGTACCGCCGCACGATCCGCGGCCGTTGCTGACCATGGACGACATGGGCCATGGCGGCATGGGCGGCATGG
ATCACGGCGCGATGGGGGGCGGTCACGACATGAGCAAGATGAAAGGCATGGAAGGCGGTTGCGGCGCGAACAT
GGGCATGGCCGGCATGGATCACGGCGCGATGCAGCACGGCGCCGCGGCCGCGCCCGCCAAGGGCGACGAACGC
CTGATCGACATGCGCGCGATGGCGACCTCGCCCAAGCTCGACGACCCGGGCATCGGCCTGCGCAACAACGGCC
GCAAGGTGCTGACTTATAGCGACCTGCGCAGTGTGTTCGACGATCCCGATGGTCGCGAGCCGAGCCGCGAGAT
CGAGCTGCACCTGACCGGCCACATGGAGAAATTCGCATGGTCGTTCGACGGCCAGAAATTCATGGGCGCCGAG
CCGATCCGCCTGACCTACGGCGAGCGCATGCGCATCGTCCTGGTCAACGACACCATGATGACCCACCCGATCC
ATCTGCACGGTCTGTGGAGCGATCTGGAGAACGAGGCCGGCGAGTTCCAGGTGCGCAAGCACACCATCGACAT
GCCGCCGGGAACGCGGCGCAGCTACCGCGTGCGCGCCGATGCGCTCGGCCGCTGGGCCTACCACTGCCACCTG
CTGTACCACATGGAAGCCGGGATGATGCGCGAAGTGAGGGTCGAGGAA

FIG. 8D

**>*Lysobacter capsici* AZ78 Copper resistance protein A** (SEQ ID NO: 4)

MNRFFSDDGGASIDAGRRRFVTGLAVGGLAAGSGLWRSAYAAPALAGAPQVLSGTEFDLSIGSSLANFTGKTR
PAITVNGSLPAPILRWREGDTVTLRVANRLAEGMSSIHWHGLILPANMDGVPGLSFDGIHPGESYVYRFRVGQ
SGTYWYHSHSMFQEQAGLYGAIVIDPREPAPFHFDREHVLLLSDWTDMDPAALFRRLKKMSSYDNYAKRTVGD
FMRDARERGLAATLRDRGEWGRMRMTPTDLSDVNGNTYTYLLNGAAPAGNWTGLFRPGEKVLLRFINGSAMTY
FDVRIPGLKMTVVAADGQYIHPVTVDEFRIAVAETFDVLVEPAGQDAYTIFAQDNGRTGHARGTLAVREGLQA
EVPPHDPRPLLTMDDMGHGGMGGMDHGAMGGGHDMSKMKGMEGGCGANMGMAGMDHGAMQHGAAAAPAKGDER
LIDMRAMATSPKLDDPGIGLRNNGRKVLTYSDLRSVFDDPDGREPSREIELHLTGHMEKFAWSFDGQKFMGAE
PIRLTYGERMRIVLVNDTMMTHPIHLHGLWSDLENEAGEFQVRKHTIDMPPGTRRSYRVRADALGRWAYHCHL
LYHMEAGMMREVRVEE

FIG. 8E

**> *Lysobacter capsici* AZ78 16S rDNA** (SEQ ID NO: 5)

GGTTAAGCTACCTGCTTCTGGTGCAACAAACTCCCATGGTGTGACGGGCGGTGTGTACAAGGCCCGGGAACGT
ATTCACCGCAGCAATGCTGATCTGCGATTACTAGCGATTCCGACTTCACGGAGTCGAGTTGCAGACTCCGATC
CGGACTGAGATAGGGTTTCTGGGATTGGCTTGCCCTCGCGGGTTTGCAGCCCTCTGTCCCTACCATTGTAGTA
CGTGTGTAGCCCTGGCCGTAAGGGCCATGATGACTTGACGTCATCCCCACCTTCCTCCGGTTTGTCACCGGGG
GTCTCCTTAGAGTTCCCACCATTACGTGCTGGCAACTAAGGACAAGGGTTGCGCTCGTTGCGGGACTTAACCC
AACATCTCACGACACGAGCTGACGACAGCCATGCAGCACCTGTCTCACGGTTCCCGAAGGCACCAATCTATCT
CTAGAAAGTTCCGTGGATGTCAAGGCCAGGTAAGGTTCTTCGCGTTGCATCGAATTAAACCACATACTCCACC
GCTTGTGCGGGCCCCCGTCAATTCCTTTGAGTTTCAGTCTTGCGACCGTACTTCCCAGGCGGCGAACTTAACG
CGTTAGCTTCGATACTGAGAGCCAAGTTGCTCCCAACATCCAGTTCGCATCGTTTAGGGCGTGGACTACCAGG
GTATCTAATCCTGTTTGCTCCCCACGCTTTCGTGCCTCAGTGTCAGTGCTGGTCCAGGTAGTCGCCTTCGCCA
CAGATGTTCCTCCCGATATCTACGCATTTCACTGCTACACCGGGAATTCCACTACCCTCTACCGCACTCTAGT
CAGCCAGTTTCCAATGCCATTCCCAGGTTGAGCCCAGGGCTTTCACATCAGACTTAACAAACCACCTACGCAC
GCTTTACGCCCAGTAATTCCGAGTAACGCTTGCACCCTTCGTATTACCGCGGCTGCTGGCACGAAGTTAGCCG
GTGCTTATTCTTCCGGTACCGTCATGACCTCAGGGTATTAACCCAAGGCTTTTCTTTCCGGACAAAAGTGCTT
TACAACCCGAAGGCCTTCTTCACACACGCGGCATGGCTGGATCAGGCTTGCGCCCATTGTCCAATATTCCCCA
CTGCTGCCTCCCGTAGGAGTCTGGACCGTGTCTCAGTTCCAGTGTGGCTGATCATCCTCTCAGACCAGCTACG
GATCGTCGCCTTGGTGGGCCTTTACCCCGCCAACTAGCTAATCCGACGTCGGCTCATCTATCTGCGCGAAGCC
CGAAGGTCCTCCGCTTTCACCCGTAGGTCGTATGCGGTATTAGCGTAAGTTTCCCTACGTTATCCCCCACAAA
TAGGCAGATTCCGACGTATTCCTCACCCGTCCGCCACTCGCCACCCAAGGAGCAAGCTCCTCTGTGCTGCCGT
TCGACTGCA

FIG. 8F

**> *Lysobacter capsici* AZ78 *atpA* (SEQ ID NO: 6)** (ATP synthase subunit alpha)

ATGGCAAGCACCCAGCTCAACCCGTCCGAAATCAGTGAACTGATCAAGACCCGCATCGAGAAGGTCAAGCTGG
CCGCCGAAGCGCGCAACGAAGGCACCGTCACCTCGGTGTCCGACGGCATCGTGCGCATCCACGGCCTGGCTGA
CGTGATGCAGGGCGAAATGATCGAACTGCCGAACAACACCTTCGCGCTCGCGCTGAACCTGGAGCGCGACTCG
GTCGGCGCCGTGGTCCTGGGCGATTACGAGCACCTGCGCGAAGGCGACATCGCCAAGACCACCGCGCGCATCC
TGGAAGTGCCGGTCGGTCGCGAACTGCTCGGCCGCGTGGTCAACGCGCTCGGCGAGCCGATCGACGGCAAGGG
TCCGATCGGCGCGGCGATGACCGCTCCGGTGGAGCGCGTCGCCCCGGGCGTGATCTGGCGCAAGTCGGTCGAT
CAGCCGGTGCAGACCGGTTACAAGACCGTCGACGCGATGATCCCGATCGGCCGCGGCCAGCGCGAGCTGATCA
TCGGCGACCGTCAGACCGGCAAGACCGCGCTGGCGATCGACGCGATCATCAACCAGAAGGGCACCGGCATTAA
GTGCGTGTACGTCGCGATCGGCCAGAAGGCCAGCTCGGTCGCCAACGTCGTGCGCAAGCTGGAAGAAAACGGC
GCGCTCGCCCACACCATCGTGGTCGCCGCGACCGCGTCGGAATCGGCCGCGATGCAGTACATCAGCGCCTACT
CGGGCTGCACCATGGGCGAGTACTTCCTCGACCGCGGCGAAGACGCGCTGATCGTGTACGACGATCTGTCCAA
GCAGGCCGTGGCCTACCGCCAGATCTCGCTGCTGCTCAAGCGCCCGCCGGGTCGCGAAGCCTATCCGGGCGAC
GTGTTCTACCTGCACAGCCGCCTGCTCGAGCGCGCCGCGCGCGTGTCGACCGAGTACGTCGAGAAGTTCACCA
ACGGCGAAGTGAAGGGCAAGACCGGTTCGCTGACCGCGCTGCCGATCATCGAAACCCAGGCCGGCGACGTTTC
GGCGTTCGTGCCGACCAACGTGATCTCGATCACCGACGGCCAGATCTTCCTGGAAACCGACCTGTTCAACGCC
GGCATCCGCCCGGCCGTGAACGCCGGTATCTCGGTGTCGCGCGTCGGTGGCGCGGCCCAGACCAAGATCGTCA
AGAAGCTGTCCGGCGGCATCCGTATCGCCCTGGCCCAGTACCGCGAGCTGGCTGCGTTCGCGCAGTTCGCTTC
CGACCTCGACGAAGCCACCCGCAAGCAGCTCGAGCGCGGTCAGCGCGTCACCGAGCTGATGAAGCAGAAGCAG
TACGCGCCGATGTCGATCGCCCTGCAGTCGCTGTCGATCTACGCGGTCGACAAGGGCTTCATGGACGACGTGC
CGGTGAACAAGATCGGTGCGTTCGAAGAAGCGCTGCACGCGCACTTCACCAATACCGCCGGCGAGCTGGTCGA
TCAGATCAACGCCACCGGCAATTGGAACGACGACATCGAAGGCGCCTTCAAGAAGGGCATCGAAGAGTTCAAG
CAGACCGGGACCTGG

FIG. 8G

**> *Lysobacter capsici* AZ78 *atpD* (SEQ ID NO: 7)** (ATP synthase subunit beta)

ATGAGCAGCCAGGGCAAGATCGTTCAGATCATCGGTGCGGTCGTCGACGTCGAGTTCGCACGCGAGTCGGTTC
CGCGCGTGTACGACGCGTTGAAGGTCGAGAACACCGCCATCACCCTCGAAGTGCAGCAGCAGCTGGGCGACGG
CATCGTGCGCGCGATCGCGCTCGGTTCCACCGACGGTCTCAAGCGCAACCTGGTGGCGATCAACACCGGCAAG
GGCGTGTCGGTGCCGGTCGGCGCGGGCACCCTGGGCCGCATCATGAACGTGCTCGGCGAGCCGATCGACGAAG
CCGGTCCGGTCGAAGCCACCGAGCATTGGGAAATCCACCGCGCGGCGCCCGATTACGCCGACCAGTCCTCGGG
CAACGAGCTGCTGGAAACCGGCATCAAGGTCATCGACCTGATGTGCCCGTTCGCCAAGGGCGGCAAGGTCGGC
CTGTTCGGCGGCGCCGGCGTGGGCAAGACGGTCAACATGCTTGAGCTGATCAACAACATCGCCACCGAGCATG
CCGGTCTGTCGGTGTTCGCCGGCGTCGGCGAGCGCACCCGCGAAGGCAACGACTTCTACCACGAGATGGCCGA
AGCCGGCGTCATCCAGCTCGAGAGCCTGAAGGACTCGAAGGTCGCGATGGTGTACGGCCAGATGAACGAGCCG
CCGGGCAACCGCCTGCGCGTCGCGCTGACCGGCCTGACCATGGCCGAATACTTCCGCGACGAAAAGGACGCCG
ACGGCAAGGGCCGCGACGTGCTGTTCTTCGTCGACAACATCTACCGCTACACCCTGGCCGGCACCGAAGTGTC
GGCGCTGCTCGGCCGCATGCCGTCGGCGGTGGGTTACCAGCCGACCCTGGCCGAGGAAATGGGCGTTCTGCAG
GAGCGCATCACCTCGACCAAGACCGGCTCGATCACCTCGATCCAGGCCGTGTACGTGCCCGCCGACGACTTGA
CCGACCCCTCGCCCGCGACCACCTTCGCCCACCTCGACGCCACCGTCGTGTTGAGCCGTAACATCGCCTCGCT
GGGTATCTACCCGGCGGTCGATCCGCTCGACTCGACCTCGCGTCAGCTCGACCCGAACGTGATCGGCGCCGAG
CACTACGACACCGCGCGCCGCGTCCAGGCCACCTTGCAGAAGTACAAGGAGCTCAAGGACATCATCGCGATCC
TCGGCATGGACGAGCTGTCGGAAGAAGACAAGCAGGCCGTGTCGCGCGCGCGCAAGATCGAGCGTTTCTTCTC
GCAGCCGTTCCACGTCGCCGAAGTGTTCACCGGCGCCCCGGGCAAGTACGTGTCGCTGAAGGACACGATCCGC
GGCTTCAAGGGCATCTGCGACGGCGAATACGACCACCTGCCGGAGCAGGCGTTCTACATGGTCGGCGGCATCG
AGGAAGCGGTCGAGAAGGCCAAGAAGATGGGCGTGGGC

FIG. 8H

**> *Lysobacter capsici* AZ78 *carA*** (SEQ ID NO: 8)

(Carbamoyl-phosphate synthase small chain)

GTGACCCAACCCGCAATCCTCGCACTCGAAGACGGCACCGTGTTCGAGGGCGTTTCCGTAGGCGCGCCCGGCC
TCAGCGTCGGCGAAGTCGTATTCAACACCGCGATCACCGGCTACCAGGAAATCCTCACCGATCCTTCGTACGC
CCGTCAGCTGGTCACGCTGACCTACCCGCACGTCGGCAACACCGGCATCACCGCGCAGGACGACGAAGCCAGC
CAAGTCTGGGCCTCGGGCCTGATCGTGCGCGACGTGCCGCGCCGCCCCAGCAACTGGCGCAGCACGATCGCGC
TGCCGCAGTGGCTGGCCGATCGCGGCGTGGTCGCGATCTCCGACATCGACACCCGCAAGCTGACCCGATTGCT
GCGCGACACCGGCGCCCAGAACGGCGCGCTGATGGCCGGCGAGATCGACGTCGCCAAGGCGATCGAAGCCGCG
CGCAAGTTCCCGGGCCTGAAGGGCATGGACCTGGCCAAGGAAGTCTGCACGCGCGAACGTTACGAGTGGACCG
AAGGTCAGCTCGACCTCGACCGCAACGCGTTCGTGAATGCGCAATCGCGTTTTCATGTGGTTGCCTACGACTT
CGGCGTCAAGCTCAACATCCTGCGCATGCTCGCCGAGCGCGGCTGCCGGGTGACCGTGGTGCCGGCGCAGACC
TCGGCCGCCGAGGTGCTGGCGCTCAAGCCCGATGGCGTGTTCCTGTCCAACGGCCCCGGCGATCCGGAGCCTT
GCGACTACGCGATCGCGGCGATCAAGGAATTCCTCGCGCAAAAGATCCCGACCTTCGGCATCTGCCTGGGCCA
TCAGCTGCTCGGCCTGGCCTCCGGCGCCAAGACCCTGAAGATGAAGTTCGGCCATCACGGCGCGAACCATCCG
GTCCAGGACCTCGACAGCGGCCGGGTGATGATCACCTCGCAGAACCACGGCTTCGCGGTCGATGAGGCCAGCC
TGCCGGCCAACGTGCGCGTGACCCACCGCTCGCTGTTCGACGGCAGCAATCAGGGCATCGCCCTGACCGACGC
GCCGGCTTTCAGTTTCCAGGGCCACCCGGAAGCGAGCCCGGGCCCGCACGATGTGTCGCCGTTGTTCGATCGG
TTCGTGGTGTCGATGGAACAGGCCAAGGCCGCC

FIG. 8I
> *Lysobacter capsici* AZ78 *gyrB* (SEQ ID NO: 9) (DNA gyrase subunit B)

```
ATGACCAACACCGAGCACGACCCCTCGACTGAATCGGCCACCGGTTCGACCCCGCCGCAAAGCGCGCAAACCC
CGCAGACCTACGACTCGAGCAAGATCACCGTCCTGCGCGGCCTCGAGGCGGTGCGCAAGCGCCCGGGCATGTA
CATCGGCGATGTCCACGACGGTACCGGCCTGCATCACATGGTCTTCGAGGTGGTCGACAACGCGATCGACGAG
GCCCTCGCCGGCCACGCCGACGATGTGGTGGTGACCTTGCACGAAGACGGTTCGGTCTCCTGCTACGACAACG
GCCGCGGCATCCCGGTCGATATCCACAAGGAAGAAGGCGTGTCGGCGGCCGAGGTGATCCTCACCGTGCTGCA
CGCCGGCGGCAAGTTCGACGACAACAGCTACAAAGTCTCCGGCGGCCTGCACGGCGTGGGCGTGTCGGTGGTC
AACGCGCTGTCCGAGCACCTGTGGCTCAACATCGGCGCGACGGTTTCCATCACCAGCAGGAATACGCGCTCG
GCGAGCCGATCTATCCGCTCAAGCAGCTGGAAGCCTCGACCAAGCGCGGCACCCTGCTGCGCTTCAAGCCGGC
GGTGGAAATCTTCACCGACGTCGAGTTCCACTACGACATCCTGGCCAAGCGCCTGCGCGAGCTGTCGTTCCTC
AACTCGGGCGTCAAGATCACTCTGGTCGACGAGCGCGGCGAAGGCCGCCGCGACGTGTTCCAGTACGAGGGCG
GGATCCGTTCCTTCGTCGAGCATCTGGCCCAGGTCAAGACGCCGCTGCACCCGAACGTGATCTCGGTGTCGGG
CGAAATGAACGGCATCACCGTCGACGTGGCGTTGCAGTGGACCGATTCCTACCAGGAAACGATGTTCTGCTTC
ACCAACAACATCCCGCAGAAAGACGGCGGCACCCACCTGATCGGTTTCCGCGCCGCGCTGACCCGCACGCTGG
CCACTTACATCGAGAAGACCGGCGCGGCCAAGCAGTCCAAGATCGCGCTGTCGGGCGAGGACATGCGCGAAGG
CATGATCGCGGTGCTGTCGGTCAAGGTGCCCGATCCGAGCTTTTCCTCGCAGACCAAGGAAAAACTGGTCAGT
TCCGAGGTGCGCCCGGTCGTTGAGAACACGTTCGGTACACGTTTGGAGGAGTTCCTGCAAGAACACCCCAACG
AAGCGCGTGCGATCACCAGCAAGATCATCGAGGCGGCGACCGCCCGCGAAGCCGCGCGCAAGGCGCGCGACCT
GACCCGCCGCAAGGGCGCGCTCGACATCGCCGGCCTGCCCGGCAAGCTCGCCGACTGCCAGGAAAAAGACCCG
GCCAAGTCCGAACTGTTCATCGTCGAGGGCGACTCCGCCGGCGGCTCGGCCAAGCAAGGCCGTAATCGCAAGA
CCCAAGCGATCCTGCCGCTCAAGGGCAAGATCCTCAACGTCGAACGCGCGCGTTTCGATCGCATGCTCGGCAG
CGCCGAAGTCGGCACCTTGATCACCGCGCTGGGCACCGGCATCGGCAAGGACGAGTACAACCCGGACAAGCTG
CGTTATCACCGCATCATCCTGATGACCGACGCCGACGTCGACGGCTCGCACATCCGCACCTTGCTGCTGACGT
TCTTCTACCGGCAGATGCCCGAGCTGATCGAGCGCGGCCACATCTACATCGGCCTGCCGCCGCTGTACAAGAT
CAAGCAGGGCAAGAACGAAATTTATCTCAAGGACGACGCGGCGCTGGATCAGTACCTGGCCAACAACGCGGTC
GAAGGCGCGGCATTGATCCCGGCGACCGGCGAGCCGCCGATCGAAGGCGCGGCGCTGGAAAAACTGCTGCTCG
CCTACGCCGGCGCGCGCGAGACCATCGCGCGCAACTCGCATCGCTACGATCCCAACGTGCTGCAGGCGCTGAT
CGATTTCACCCCGCTCGATACCGAGCACCTGCTGGCCAACGTCGATGAGCGGCACGAACTCGACGCCCTGGAA
AAGCGCCTCAACCAGACCGGACTGGGCAAGCCGCGCTACGCGCTGCAGCTGCATCCGGCCAACGAGACGCGCC
AGGCGGCGCTGCTGGTCACCCGCACCCACATGGGCCAGCAACTGATCCAGGTGCTGCCGTTGTCGGCGTTCGA
AGGCGGCGAACTGCGTTCGCTGCGCGAGGCCGCCTCGATGCTGCACGGCCTGGTGCGCGAAGGCGCGCAGATC
ATCCGCGGCAATCGCGCGCAGCCGATCAACAGCTTCGCTCAGGCGCAGGCCTGGTTGCTCGAGGAAGCCAAGA
AGGGCCGCGCGATCCAGCGCTTCAAGGGCCTGGGCGAAATGAACCCCGAGCAGCTGTGGGACACCACGGTCAA
TCCCGAAACGCGCCGTCTGTTGCAGGTGCGCATCGAGGACGCCGTGGCGGCCGACCAGATCTTCAGCACCCTG
ATGGGCCATGTCGTCGAACCGCCCCGCCAGTTCATCGAGGACAACGCGCTCAAGGTCTCCAATCTCGACGTC
```

FIG. 8J

**> *Lysobacter capsici* AZ78 *recA*** (SEQ ID NO: 10)

ATGGACGAGAACAAGAAGCGCGCCCTTACCGCCGCTCTGAGCCAGATCGACAAGCAATTCGGCAAGGGCTCGG
TGATGCGCATGGGCGACCGCGCGGTCGAGATCACCGAAGTCATCGGTACCGGCTCGCTGATGCTCGACATCGC
GCTGGGCATCGGCGGCCTGCCCAAGGGCCGCGTGGTCGAGATCTACGGTCCGGAGTCCTCGGGCAAGACCACC
TTGACCCTGCAGGCCATCGCCGAATGCCAGAAGAAGGGCGGCACCGCCGCCTTCATCGACGCCGAGCACGCGC
TCGACCCGATCTATGCCGCCAAGCTCGGCGTCAATGTCGACGACCTGCTGCTGTCGCAGCCCGACACCGGCGA
ACAGGCGCTGGAAATCGCCGACATGCTGGTGCGTTCGGCCGCGGTCGACATCGTCGTGATCGACTCGGTCGCC
GCGCTGACCCCGAAGGCCGAAATCGAAGGCGAAATGGGCGACCAGCTGCCGGGCCTGCAGGCCCGTCTGATGA
GCCAGGCGCTGCGCAAGCTGACCGGCAACATCAAGCGCTCGGGCACCCTGGTGGTGTTCATCAATCAGCTGCG
CATGAAGATCGGCGTGATGATGCCGGGCCAGAGCCCGGAAGTGACCACCGGCGGCAACGCGCTCAAGTTCTAC
GCCTCGGTGCGCCTGGACATCCGCCGCATCGGCGCGATCAAGAAGGGCGACGAGATCATCGGCAACCAGACCA
AGATCAAGGTCGTCAAGAACAAGCTCGCCCCGCCGTTCAAGCAGGTCGTCACCGAAATCCTCTACGGCGAAGG
CATCTCGCGCGAAGGCGAACTGATCGACATGGGCGTGGAAGCCAAGCTGGTCGAGAAGTCCGGCGCCTGGTAC
AGCTGCGGCGACGAGCGCATCGGCCAGGGCAAGGAAAACGCCCGCCAGTACCTCAAGGAAAACCCCGAGATGG
CGGCCCGCCTGGAAGCGACGCTGCGCGAGAAGTTCGTGCCCAGCGACGCCCCGCGCGAAGAAGTCATCGAGGA
C

FIG. 8K

**> *Lysobacter capsici* AZ78 *rpoA*** (SEQ ID NO: 11)
(DNA-directed RNA polymerase subunit alpha)

ATGACGGTTACCGCCAATCAGGTACTGCGCCCGCGTGGTCCGCAGATCGAACGCCTCACCGGCAATCGCGCGA
AGGTCGTGATCGAGCCGCTGGAGCGCGGTTACGGCCATACGCTGGGCAACGCGCTGCGGCGCGTGCTGCTGTC
GTCGATCCCGGGTTTCGCCATCACCGAGGTCGAAATCGATGGCGTGCTGCATGAGTACACCACGGTCGAAGGT
CTGGAAGAGGACGTGCTGGAGGTTCTGCTGAACCTCAAGGACGTCGCCATCCGCATGCACACCGGCGACGCGT
CGACGCTGTCGCTGGCCAAGCAAGGTCCCGGCATCGTCACCGCCGGCGACATCAAGACCGACCACAACGTCGA
AATCCTCAACACCGACCACGTGATCTGCCACCTGACCAAGGATACGGCGATCAACATGCGTCTGAAGATCGAA
CGCGGTTTCGGCTACCAGCCGGCGGCTTCGCGCCGTCGTCCGGACGAAGAAACCCGCGCGATCGGTCGTCTGA
TGCTGGACGCGAGCTTCTCGCCGGTCCGTCGCGTCGCCTACGCGGTGGAAGCCGCGCGCGTCGAGCAGCGCAC
CGATCTCGACAAGCTGGTGCTGGACATCGAAACCAACGGCACGATCGACGCCGAGGAAGCCGTGCGCACCGCC
GCCGACATCCTCACCGATCAGCTGTCGGTGTTCGGCGACTTCACCCACCGCGACCGCGGTGCGGCGAAGCCGG
CCACCAGCGGCATCGATCCGATCCTGCTGCGCCCGATCGACGATCTCGAGCTCACCGTGCGTTCGGCCAACTG
CCTCAAGGCCGAGAGCATCTACTACGTCGGCGATCTGATCCAGAAGACCGAAGTCGAGCTGCTCAAGACCCCG
AACCTGGGCAAGAAGTCGCTCACCGAGATCAAGGAAGTGCTGGCTCAGCGCGGCCTGTCGCTCGGCATGAAGC
TGGAAAACTGGCCGCCGGCGGGTATCGCCTCGCACGGAATGATGGGG

FIG. 8L

**> *Lysobacter capsici* AZ78 *rpoD*** (SEQ ID NO: 12)

(RNA polymerase sigma factor rpoD)

```
ATGGCCAACGAACGTCAGCCCCCTCCGTCCGATATCAAGCTCCTGATCAGCAAGGGCTTGGAGCAGGGCTATC
TGACCTATGCCGAGGTCAACGATCACCTGCCCGACGATCTCGTCGACGCCGAACAGATCGAAGACATCATCGG
CATGATCAACGGCATGGGCATCGAGGTGCATGAAGTTGCGCCCGATGCCGAAACGCTGTTGCTCGCCGACGGC
AATACCGGTAACCGCGAAGTCGACGACACCGCCGCTGAAGAAGCCGCGGCGGCGCTGACTGCGCTCGACGGCG
AAGGCGGCCGTACCACCGACCCGGTGCGCATGTACATGCGCGAAATGGGCACGGTGGAACTGCTGACCCGCGA
AGGCGAAATCGCCATCGCCAAGCGCATCGAAGAAGGCCTCAACCAGGTCCAGGCTTCGCTCGCTCTGTTCCCG
TCCACCATCCAGCTGATCCTGGAGGACTACGAAACCCACAAGGCCGGCAAAAAGCGCCTGGCCGAGATCGTCG
TGGGCTTCAACGATCACCTCGACGAAGAACCCGAACCGCCGGCGCCGCCGGTGGTGGTAGCCGAAACCGACGC
CGACGCGGACGACGACGAAGAAGTCGAAGCCGCCGGCGACGATGCCGACGCCGAGGAAACCACGTCCGGCCCC
GATCCGGTCGAAGTCGCCGCGCGCATGGAGGCCATCGCCGACCTGTACGGCAAGTTCGTCAAGGCCCAGGCCA
AGAACGGCGCCGGCCACAAGACCGTGACCAAGCTGCGCGAAGACATCGCCGCGGTGTTCGTCACCCTCAAGCT
GCCGCTCGCCCTGACCGACAGCCTGATGCGCAACCTGCGCGACGTGGTCGGTTCGATCAAGGACCGCGAGCGC
AAGATTCTGGATCTGGCCACCCGCGTCGCCAAGATGCCGCGCAAGGATTTCATCCGCGCGTGGGAAGGCAACC
AGACCAATCTGGAATGGGTCGACGAACTGCTCAAGCGCAAGCAGAAGTGGTCGTCGGGCCTGCGCGACGTCAA
GGATCAGATCATCGTCGAACAGCAGACGACGATCGAAATCGAACAGGCCTCGCTGCTGACCTTGAACGACATC
AAGGAAATCAGCCGCGCGATGGCCTACGGCGAGGCCAAGGCGCGCAAGGCCAAGAAGGAAATGGTCGAGGCCA
ACCTGCGTCTGGTGATCTCGATCGCCAAGAAGTACACCAACCGCGGCCTGCAGTTCCTCGATCTGATCCAGGA
AGGCAACATCGGTCTGATGAAGGCGGTCGACAAGTTCGAATTCCGCCGCGGCTTCAAGTTCTCGACCTACGCC
ACGTGGTGGATCCGTCAGGCCATCACCCGTTCGATCGCCGATCAGGCCCGCACCATCCGTATCCCGGTGCACA
TGATCGAGACGATCAACAAGCTCAACCGCATCTCGCGTCAGATGCTCCAGCAGTACGGCCGCGAGGCCACGCC
GGAAGAGCTTGCGAAAGAAATGGACATGCCCGAGGACAAGATCCGCAAGGTCATGAAGATCGCCAAGGAGCCC
ATCTCGATGGAAACTCCGATCGGCGACGACGAAGACTCGCACCTGGGCGACTTCATCGAGGACACCAACGTGG
AGTCCCCGGTCGAAGCCACCACCAACATCAACCTGTCGGAAACGGTCCGCGACGTGCTCGCCGGCCTGACCCC
GCGCGAGGCCAAGGTGTTGCGCATGCGTTTCGGCATCGACATGAACACCGATCACACGCTGGAAGAAGTCGGC
AAGCAGTTCGACGTGACCCGCGAGCGCATCCGTCAGATCGAAGCGAAGGCGCTGCGCAAGCTGCGTCATCCGA
GCCGGTCGGAACAGCTGCGCAGCTTCCTCGATATCGAT
```

FIG. 8M

**> *Lysobacter capsici* AZ78 *uvrB*** (SEQ ID NO: 13) (UvrABC system protein B)

ATGGACGACAGTCAGCAGTCCGCCGGTTTCCAGCTAGTTTCGCCGTATTCGCCGGCCGGCGATCAGCCGCAGG
CGATCGACAAGCTGGTCGCCGGTTTCGAGGGCGGCCTGGCCCAGCAGACCCTGCTCGGCGTGACCGGCTCGGG
CAAGACCTACACCATCGCCAACGTGGTCCAGGCGGTGCAGAAGCCGACCCTGGTGATGGCGCCGAACAAGACC
CTGGCCGCGCAGCTGTACGGCGAGTTCAAGGCGTTCTTTCCGCACAACGCGGTCGAGTACTTCGTCAGCTACT
ACGACTACTACCAGCCCGAGGCCTACGTGCCGTCGAGCGACACCTTCATCGAGAAGGACAGCTCGGTCAACGA
GCACATCGAGCAGATGCGGCTGTCGGCGACCAAGGCCCTGCTCGAGCGGCGCGACGCGCTGATCGTGTGCACG
GTTTCGGCGATCTACGGCCTGGGCGATCCGAACGAATACTTCCGCATGGTCCTGCACATGGTCCGCGGCGAGC
GCATCGACCAGCGCGAGCTGATCCGCCGCCTGACCGAGATGCAGTACACCCGCAACGACACCGAACTGCGCCG
CGCGACCTACCGCGTGCGCGGCGAAGTCATCGACGTGCATCCGGCCGAAAGCGATTCGCAGGCGCTGCGCGTG
GAGCTGTTCGACGGCGAAATCGAAAACCTGACCCTGTTCGATCCGCTGACCGGCGAAACCCTGGAACGGGTGC
CGCGCTTCACCATCTACCCCGGTTCGCACTACGTCACCACCCGCCGCACCGTGCTCGACGCGATCGAGACGAT
CAAGGAAGAGCTGCGCGAGCGCCTGGAATACCTGTACGCGAACAACAAGCTGGTCGAGGCGCAGCGCCTGGCC
CAGCGCACCCAGTTCGACCTTGAGATGCTGGCCGAGGTCGGCTACTGCAACGGCATCGAGAACTACTCGCGGC
ACCTGAGCGGGCACATGCCCGGCGAGCCGCCGCCGTGCCTGTTCGACTACCTGCCGCCCGACGCGCTGCTGGT
GGTCGACGAATCGCACGTCACCATTCCGCAGATCGGCGCGATGTACAAAGGCGACCGCTCGCGCAAGGAAACC
CTGGTCGAGTTCGGTTTCCGCATGCCCTCGGCGCTGGACAACCGGCCGCTGCGGTTCGAAGAATGGGAAGGGC
GCTCGCCGCGCGCGATCTATGTCTCGGCCACGCCCGGTCCGTATGAACTGAAGAAGTCGGAAGGGCAGATCAC
CGAGCTGGTGGTGCGTCCGACCGGCCTGATCGATCCGGTGGTCGAGATCCGCCCGGTCGCGACCCAGGTCGAC
GACGTGCTCGGCGAGATCCGCGAGCGCGTGGCGATGGGCGATCGCGTGCTGATCACCACCCTGACCAAGCGCA
TGTCGGAAAACCTCACCGAATACCTCGGCGAACACGGGATCAAGGTGCGCTACCTGCATTCGGACATCGAGAC
CGTGGAGCGGGTCGAGATCATCCGCGACCTGCGCCTGGGCAAGTTCGACGTGCTGGTCGGCATCAACCTGCTG
CGCGAGGGCCTGGACATGCCCGAGGTGTCGCTGGTCGCGATCCTCGACGCCGACAAGGAAGGTTTCCTGCGTT
CGACCGGTTCGCTGATCCAGACCATCGGCCGCGCCGCGCGCAACCTGCGCGGCAAGGCGATCCTGTACGCCGA
CCGCATCACCAACTCGATGCAGCGCGCGATCGAGGAAACCGACCGACGCCGGCAGAAACAGGTCGAGTACAAC
GAAGCCCACGGCATCACCCCTAAGTCGGTCGACAAGGCGGTGGTCGACATCATGGAAGGCGCCCGGGTCGATC
CCGAAGCGCTCAAGGCGCGCGGCAAGGGCCGTCGGGCGACCGAGGACGCGGCGGACGTCGCGAGCCTCAGCCC
GGCCCAGTTCGCGGCCAGGATCAAGGCGCTGGAGCAGCAGATGTACCAGCACGCCCGCGATCTGGAGTTCGAA
CAGGCCGCGGCGGTGCGCGATCAACTGCGCAAACTCAAGGACGCCGGACTGGGCGCC

SEQUENCE LISTING

```
<160> NUMBER OF SEQ ID NOS: 17

<210> SEQ ID NO 1
<211> LENGTH: 2415
<212> TYPE: DNA
<213> ORGANISM: Lysobacter capsici
<220> FEATURE:
<221> NAME/KEY: CDS
<222> LOCATION: (1)..(2415)

<400> SEQUENCE: 1

atg acc tgc agc tcc tgc gtc ggc cgc atc gag cgg gcc gtg tcc gcc       48
Met Thr Cys Ser Ser Cys Val Gly Arg Ile Glu Arg Ala Val Ser Ala
1               5                   10                  15

ctg ccc ggc gtc gcc gag gtc agc gtc aat ctg gcc acc gaa atc gcc       96
Leu Pro Gly Val Ala Glu Val Ser Val Asn Leu Ala Thr Glu Ile Ala
            20                  25                  30

gag gtc gcc cac gac gcc agc gtc tcc gcc gcg cag atc gaa cgc gcc      144
Glu Val Ala His Asp Ala Ser Val Ser Ala Ala Gln Ile Glu Arg Ala
        35                  40                  45

atc gcc gcc gcc ggt tac agc gtc ccc agc gag gag ctc gtg ctg gcg      192
Ile Ala Ala Ala Gly Tyr Ser Val Pro Ser Glu Glu Leu Val Leu Ala
    50                  55                  60

ctg cgc ggg atg aat tgc ggc tcc tgc gtc ggc cgg atc gag aag gcg      240
Leu Arg Gly Met Asn Cys Gly Ser Cys Val Gly Arg Ile Glu Lys Ala
65                  70                  75                  80

ctc acc gcg gtg ccg ggc gtg ctc gag gcc tcg gtc aat ctg gcc acc      288
Leu Thr Ala Val Pro Gly Val Leu Glu Ala Ser Val Asn Leu Ala Thr
                85                  90                  95

gag cgc gcc agg ctg cgc atg ctc gaa ggc acc gac acg gcc gcg ctg      336
Glu Arg Ala Arg Leu Arg Met Leu Glu Gly Thr Asp Thr Ala Ala Leu
            100                 105                 110

atc gcc gca gtc aag cgc gcc ggt tac gaa gcg agc ctg ccc gac agc      384
Ile Ala Ala Val Lys Arg Ala Gly Tyr Glu Ala Ser Leu Pro Asp Ser
        115                 120                 125

gat ccc gac aac ccg tcc ggc ggc ggc gca agc agc gca tcc gct ggc      432
Asp Pro Asp Asn Pro Ser Gly Gly Gly Ala Ser Ser Ala Ser Ala Gly
    130                 135                 140

gac agc tcg cac gcg ccg cgt acc gac agc ggc atc gcc acc gcc gcc      480
Asp Ser Ser His Ala Pro Arg Thr Asp Ser Gly Ile Ala Thr Ala Ala
145                 150                 155                 160
```

-continued

```
gcc cac ggc aac gcc aag ccc gcg ctg acg cgc gaa acc cgc cat ctg      528
Ala His Gly Asn Ala Lys Pro Ala Leu Thr Arg Glu Thr Arg His Leu
                165                 170                 175

ctg atc gcc gcc gcg ctg tcg ctg ccc ttg gtc gcg ccg atg ctc ggc      576
Leu Ile Ala Ala Ala Leu Ser Leu Pro Leu Val Ala Pro Met Leu Gly
            180                 185                 190

ctg ttg ttc ggt cag cac tgg atg ctg ccg ggc tgg ctg cag ttc gcc      624
Leu Leu Phe Gly Gln His Trp Met Leu Pro Gly Trp Leu Gln Phe Ala
        195                 200                 205

ctg gcc acg ccg gtg cag ttc tgg ctc ggc gcg cgc ttt tat cgc gcc      672
Leu Ala Thr Pro Val Gln Phe Trp Leu Gly Ala Arg Phe Tyr Arg Ala
    210                 215                 220

ggc tgg agc gca ctg cgc gcg cgc agc ggc aac atg gac ctg ctg gtc      720
Gly Trp Ser Ala Leu Arg Ala Arg Ser Gly Asn Met Asp Leu Leu Val
225                 230                 235                 240

gcg ctc ggc agc agc gcc ggt tac ggc ctg agc ctg tac cac ctg ctg      768
Ala Leu Gly Ser Ser Ala Gly Tyr Gly Leu Ser Leu Tyr His Leu Leu
                245                 250                 255

cgc ggc gat cag atg cag ctg tat ttc gaa acc tcg gcg gtg atc gtc      816
Arg Gly Asp Gln Met Gln Leu Tyr Phe Glu Thr Ser Ala Val Ile Val
            260                 265                 270

acc ctg atc ctg ttc ggc aaa tgg ctg gaa gcg cgc gcc aag cgc cag      864
Thr Leu Ile Leu Phe Gly Lys Trp Leu Glu Ala Arg Ala Lys Arg Gln
        275                 280                 285

acc acc gcg gcg atc cgc gcc ctg cag gcg ctg cgc ccg agc agc gcg      912
Thr Thr Ala Ala Ile Arg Ala Leu Gln Ala Leu Arg Pro Ser Ser Ala
    290                 295                 300

cgg gtg ctg cgc gac ggc gtc gaa cac gaa ctg ccg ctg gcg cag ttg      960
Arg Val Leu Arg Asp Gly Val Glu His Glu Leu Pro Leu Ala Gln Leu
305                 310                 315                 320

cgg gtc ggc gac ctc gtg gtg gtg cgt ccg ggc gaa cgc ctg ccg gcc     1008
Arg Val Gly Asp Leu Val Val Val Arg Pro Gly Glu Arg Leu Pro Ala
                325                 330                 335

gac ggc cgc atc gtc gaa ggc ctc acc cac gtc gac gaa tcc ctg ctc     1056
Asp Gly Arg Ile Val Glu Gly Leu Thr His Val Asp Glu Ser Leu Leu
            340                 345                 350

acc ggc gaa tcc ctg ccg gtc gcg cgc gag cgc ggc gac cgc gtc acc     1104
Thr Gly Glu Ser Leu Pro Val Ala Arg Glu Arg Gly Asp Arg Val Thr
        355                 360                 365

ggc ggc gcg atc aac ggc gaa ggc cgc atc gtg gtc gag acc gtg gcg     1152
Gly Gly Ala Ile Asn Gly Glu Gly Arg Ile Val Val Glu Thr Val Ala
    370                 375                 380

gtc ggc gcg gag agc gcg ctc gcc cgc atc atc cgt ctg gtc gag gac     1200
Val Gly Ala Glu Ser Ala Leu Ala Arg Ile Ile Arg Leu Val Glu Asp
385                 390                 395                 400

gcg cag gcc aag aag gcg ccg atc cag cac ttg gtc gac cgg gtc agc     1248
Ala Gln Ala Lys Lys Ala Pro Ile Gln His Leu Val Asp Arg Val Ser
                405                 410                 415

gcg gtg ttc gtg ccg gtg gtg atc gcg atc gcg ctg ctg acc ctg atc     1296
Ala Val Phe Val Pro Val Val Ile Ala Ile Ala Leu Leu Thr Leu Ile
            420                 425                 430

ggc tgg ggc ctg tat gcc ggc gac tgg agc cag gcc gtg ctc aac gcg     1344
Gly Trp Gly Leu Tyr Ala Gly Asp Trp Ser Gln Ala Val Leu Asn Ala
        435                 440                 445

gtc gcg gtg ctg gtg atc gcc tgt ccg tgc gcg ctg ggc ctg gcc acg     1392
Val Ala Val Leu Val Ile Ala Cys Pro Cys Ala Leu Gly Leu Ala Thr
    450                 455                 460

ccg acc gcg atc atg gcc ggc acc ggc gtg gcc gcg cgc gcg ggc att     1440
Pro Thr Ala Ile Met Ala Gly Thr Gly Val Ala Ala Arg Ala Gly Ile
```

-continued

```
465                 470                 475                 480

ctg atc aag gac gcc gaa gcg ctg gaa atc gcg cat cga atc gac gtg     1488
Leu Ile Lys Asp Ala Glu Ala Leu Glu Ile Ala His Arg Ile Asp Val
                485                 490                 495

gtc gcg ttc gac aag acc ggc acc ctg acc gaa ggc aag ccg gtg ctg     1536
Val Ala Phe Asp Lys Thr Gly Thr Leu Thr Glu Gly Lys Pro Val Leu
            500                 505                 510

agc gaa tgg acc gcg ctc gac ggc gac cgc gac gca ctg ctg cgc ttc     1584
Ser Glu Trp Thr Ala Leu Asp Gly Asp Arg Asp Ala Leu Leu Arg Phe
        515                 520                 525

gcc gcg gcg ctg caa tcg ggc agc gag cat ccg ctg gcc cgc gcc acc     1632
Ala Ala Ala Leu Gln Ser Gly Ser Glu His Pro Leu Ala Arg Ala Thr
    530                 535                 540

ctc gac gcg gcg cgc gcg ctg agc ctg ccg ccg gtg tcg caa ttg cag     1680
Leu Asp Ala Ala Arg Ala Leu Ser Leu Pro Pro Val Ser Gln Leu Gln
545                 550                 555                 560

gcg ctg gcc gga cgc ggc ctg cgc ggc gag gtc gaa ggc cgc aac ctg     1728
Ala Leu Ala Gly Arg Gly Leu Arg Gly Glu Val Glu Gly Arg Asn Leu
                565                 570                 575

ctg ctc ggc agc acc cgc atg ctc gaa gaa gcc ggc gtc gat ctg caa     1776
Leu Leu Gly Ser Thr Arg Met Leu Glu Glu Ala Gly Val Asp Leu Gln
            580                 585                 590

cca ctg cgc gag gcg gcg cag cgc ctg gcc gac agc ggc cac agc gta     1824
Pro Leu Arg Glu Ala Ala Gln Arg Leu Ala Asp Ser Gly His Ser Val
        595                 600                 605

tcg tgg ctg gcg cgc gac ggc gcc gac ggc gcg cag ttg ctc ggc ctg     1872
Ser Trp Leu Ala Arg Asp Gly Ala Asp Gly Ala Gln Leu Leu Gly Leu
    610                 615                 620

ctc ggc ttc cgc gat acc ccg cgc gcc aac gcc cgc gcg gcg atc gaa     1920
Leu Gly Phe Arg Asp Thr Pro Arg Ala Asn Ala Arg Ala Ala Ile Glu
625                 630                 635                 640

cgc ctg cat gca ttg ggt gtg agc acc gcg atg atc tcc ggc gat cac     1968
Arg Leu His Ala Leu Gly Val Ser Thr Ala Met Ile Ser Gly Asp His
                645                 650                 655

atc ggc gca gcg cgc gcg gtc gcc gcc gaa ctc ggc atc gac cag atc     2016
Ile Gly Ala Ala Arg Ala Val Ala Ala Glu Leu Gly Ile Asp Gln Ile
            660                 665                 670

cgc gcc gac gta ttg ccc gaa cag aag gcc gcc gcg gtc gcc gaa ctc     2064
Arg Ala Asp Val Leu Pro Glu Gln Lys Ala Ala Ala Val Ala Glu Leu
        675                 680                 685

ggc cag ttc cgc acc gtg gcg atg gtc ggc gac ggt gtc aac gac gcg     2112
Gly Gln Phe Arg Thr Val Ala Met Val Gly Asp Gly Val Asn Asp Ala
    690                 695                 700

ccg gcg ctg gcc gcg gcc gat gtc ggc atc gcc atg ggc agc ggc acc     2160
Pro Ala Leu Ala Ala Ala Asp Val Gly Ile Ala Met Gly Ser Gly Thr
705                 710                 715                 720

gac gtg gcg atg cag gcc gcc ggc atc acc ctg atg cgc gcc gag ccg     2208
Asp Val Ala Met Gln Ala Ala Gly Ile Thr Leu Met Arg Ala Glu Pro
                725                 730                 735

gga ctg gtc gcc gac gcg atc gaa atc tcg cgc cgc acc agc cgc aag     2256
Gly Leu Val Ala Asp Ala Ile Glu Ile Ser Arg Arg Thr Ser Arg Lys
            740                 745                 750

atc cgc cag aac ctg ttc tgg gcg ttc ggc tac aac gtg atc ggc atc     2304
Ile Arg Gln Asn Leu Phe Trp Ala Phe Gly Tyr Asn Val Ile Gly Ile
        755                 760                 765

ggc ctg gcg acc ttg ggc tgg ttg aac ccg gtg gtc gcc gcc gcg gcg     2352
Gly Leu Ala Thr Leu Gly Trp Leu Asn Pro Val Val Ala Ala Ala Ala
    770                 775                 780

atg gcc ttc tcc agc gtc agc gtg atc ggc aac act ctg ctg ctg cgc     2400
```

-continued

```
Met Ala Phe Ser Ser Val Ser Val Ile Gly Asn Thr Leu Leu Leu Arg
785                 790                 795                 800

cgc tgg aaa ccg gca                                                2415
Arg Trp Lys Pro Ala
                805


<210> SEQ ID NO 2
<211> LENGTH: 805
<212> TYPE: PRT
<213> ORGANISM: Lysobacter capsici

<400> SEQUENCE: 2

Met Thr Cys Ser Ser Cys Val Gly Arg Ile Glu Arg Ala Val Ser Ala
1               5                   10                  15

Leu Pro Gly Val Ala Glu Val Ser Val Asn Leu Ala Thr Glu Ile Ala
            20                  25                  30

Glu Val Ala His Asp Ala Ser Val Ser Ala Ala Gln Ile Glu Arg Ala
        35                  40                  45

Ile Ala Ala Ala Gly Tyr Ser Val Pro Ser Glu Glu Leu Val Leu Ala
    50                  55                  60

Leu Arg Gly Met Asn Cys Gly Ser Cys Val Gly Arg Ile Glu Lys Ala
65                  70                  75                  80

Leu Thr Ala Val Pro Gly Val Leu Glu Ala Ser Val Asn Leu Ala Thr
                85                  90                  95

Glu Arg Ala Arg Leu Arg Met Leu Glu Gly Thr Asp Thr Ala Ala Leu
            100                 105                 110

Ile Ala Ala Val Lys Arg Ala Gly Tyr Glu Ala Ser Leu Pro Asp Ser
        115                 120                 125

Asp Pro Asp Asn Pro Ser Gly Gly Gly Ala Ser Ser Ala Ser Ala Gly
    130                 135                 140

Asp Ser Ser His Ala Pro Arg Thr Asp Ser Gly Ile Ala Thr Ala Ala
145                 150                 155                 160

Ala His Gly Asn Ala Lys Pro Ala Leu Thr Arg Glu Thr Arg His Leu
                165                 170                 175

Leu Ile Ala Ala Ala Leu Ser Leu Pro Leu Val Ala Pro Met Leu Gly
            180                 185                 190

Leu Leu Phe Gly Gln His Trp Met Leu Pro Gly Trp Leu Gln Phe Ala
        195                 200                 205

Leu Ala Thr Pro Val Gln Phe Trp Leu Gly Ala Arg Phe Tyr Arg Ala
    210                 215                 220

Gly Trp Ser Ala Leu Arg Ala Arg Ser Gly Asn Met Asp Leu Leu Val
225                 230                 235                 240

Ala Leu Gly Ser Ser Ala Gly Tyr Gly Leu Ser Leu Tyr His Leu Leu
                245                 250                 255

Arg Gly Asp Gln Met Gln Leu Tyr Phe Glu Thr Ser Ala Val Ile Val
            260                 265                 270

Thr Leu Ile Leu Phe Gly Lys Trp Leu Glu Ala Arg Ala Lys Arg Gln
        275                 280                 285

Thr Thr Ala Ala Ile Arg Ala Leu Gln Ala Leu Arg Pro Ser Ser Ala
    290                 295                 300

Arg Val Leu Arg Asp Gly Val Glu His Glu Leu Pro Leu Ala Gln Leu
305                 310                 315                 320

Arg Val Gly Asp Leu Val Val Val Arg Pro Gly Glu Arg Leu Pro Ala
                325                 330                 335

Asp Gly Arg Ile Val Glu Gly Leu Thr His Val Asp Glu Ser Leu Leu
```

-continued

```
            340                 345                 350

Thr Gly Glu Ser Leu Pro Val Ala Arg Glu Arg Gly Asp Arg Val Thr
        355                 360                 365

Gly Gly Ala Ile Asn Gly Glu Gly Arg Ile Val Val Glu Thr Val Ala
    370                 375                 380

Val Gly Ala Glu Ser Ala Leu Ala Arg Ile Ile Arg Leu Val Glu Asp
385                 390                 395                 400

Ala Gln Ala Lys Lys Ala Pro Ile Gln His Leu Val Asp Arg Val Ser
                405                 410                 415

Ala Val Phe Val Pro Val Val Ile Ala Ile Ala Leu Leu Thr Leu Ile
            420                 425                 430

Gly Trp Gly Leu Tyr Ala Gly Asp Trp Ser Gln Ala Val Leu Asn Ala
        435                 440                 445

Val Ala Val Leu Val Ile Ala Cys Pro Cys Ala Leu Gly Leu Ala Thr
    450                 455                 460

Pro Thr Ala Ile Met Ala Gly Thr Gly Val Ala Ala Arg Ala Gly Ile
465                 470                 475                 480

Leu Ile Lys Asp Ala Glu Ala Leu Glu Ile Ala His Arg Ile Asp Val
                485                 490                 495

Val Ala Phe Asp Lys Thr Gly Thr Leu Thr Glu Gly Lys Pro Val Leu
            500                 505                 510

Ser Glu Trp Thr Ala Leu Asp Gly Asp Arg Asp Ala Leu Leu Arg Phe
        515                 520                 525

Ala Ala Ala Leu Gln Ser Gly Ser Glu His Pro Leu Ala Arg Ala Thr
    530                 535                 540

Leu Asp Ala Ala Arg Ala Leu Ser Leu Pro Pro Val Ser Gln Leu Gln
545                 550                 555                 560

Ala Leu Ala Gly Arg Gly Leu Arg Gly Glu Val Glu Gly Arg Asn Leu
                565                 570                 575

Leu Leu Gly Ser Thr Arg Met Leu Glu Glu Ala Gly Val Asp Leu Gln
            580                 585                 590

Pro Leu Arg Glu Ala Ala Gln Arg Leu Ala Asp Ser Gly His Ser Val
        595                 600                 605

Ser Trp Leu Ala Arg Asp Gly Ala Asp Gly Ala Gln Leu Leu Gly Leu
    610                 615                 620

Leu Gly Phe Arg Asp Thr Pro Arg Ala Asn Ala Arg Ala Ala Ile Glu
625                 630                 635                 640

Arg Leu His Ala Leu Gly Val Ser Thr Ala Met Ile Ser Gly Asp His
                645                 650                 655

Ile Gly Ala Ala Arg Ala Val Ala Ala Glu Leu Gly Ile Asp Gln Ile
            660                 665                 670

Arg Ala Asp Val Leu Pro Glu Gln Lys Ala Ala Ala Val Ala Glu Leu
        675                 680                 685

Gly Gln Phe Arg Thr Val Ala Met Val Gly Asp Gly Val Asn Asp Ala
    690                 695                 700

Pro Ala Leu Ala Ala Ala Asp Val Gly Ile Ala Met Gly Ser Gly Thr
705                 710                 715                 720

Asp Val Ala Met Gln Ala Ala Gly Ile Thr Leu Met Arg Ala Glu Pro
                725                 730                 735

Gly Leu Val Ala Asp Ala Ile Glu Ile Ser Arg Arg Thr Ser Arg Lys
            740                 745                 750

Ile Arg Gln Asn Leu Phe Trp Ala Phe Gly Tyr Asn Val Ile Gly Ile
        755                 760                 765
```

```
Gly Leu Ala Thr Leu Gly Trp Leu Asn Pro Val Val Ala Ala Ala Ala
    770                 775                 780

Met Ala Phe Ser Ser Val Ser Val Ile Gly Asn Thr Leu Leu Leu Arg
785                 790                 795                 800

Arg Trp Lys Pro Ala
                805


<210> SEQ ID NO 3
<211> LENGTH: 1800
<212> TYPE: DNA
<213> ORGANISM: Lysobacter capsici
<220> FEATURE:
<221> NAME/KEY: CDS
<222> LOCATION: (1)..(1800)

<400> SEQUENCE: 3

atg aac aga ttt ttc tcc gac gac ggc ggc gca tcg atc gat gcc ggc       48
Met Asn Arg Phe Phe Ser Asp Asp Gly Gly Ala Ser Ile Asp Ala Gly
1               5                   10                  15

cgt cgc cgt ttc gtc acc ggc ctg gcg gtc ggc ggc cta gcc gca ggc       96
Arg Arg Arg Phe Val Thr Gly Leu Ala Val Gly Gly Leu Ala Ala Gly
            20                  25                  30

agc ggc ctg tgg cgt tcg gcc tat gcc gcg ccc gcg ctg gcc ggt gcg      144
Ser Gly Leu Trp Arg Ser Ala Tyr Ala Ala Pro Ala Leu Ala Gly Ala
        35                  40                  45

ccg cag gta ttg agc ggg acc gaa ttc gat ctc tcg atc ggc tcg tcg      192
Pro Gln Val Leu Ser Gly Thr Glu Phe Asp Leu Ser Ile Gly Ser Ser
    50                  55                  60

ctg gcc aac ttc acc ggc aag acg cgc ccg gcg atc acc gtc aac ggc      240
Leu Ala Asn Phe Thr Gly Lys Thr Arg Pro Ala Ile Thr Val Asn Gly
65                  70                  75                  80

agc ctg ccc gcg ccg atc ctg cgc tgg cgc gaa ggc gat acg gtg acc      288
Ser Leu Pro Ala Pro Ile Leu Arg Trp Arg Glu Gly Asp Thr Val Thr
                85                  90                  95

ttg cgg gtc gcc aac cgg ctc gcc gaa ggc atg agc tcg atc cat tgg      336
Leu Arg Val Ala Asn Arg Leu Ala Glu Gly Met Ser Ser Ile His Trp
            100                 105                 110

cac ggc ctg atc ctg ccg gcc aac atg gac ggc gtg ccg ggc ctg agc      384
His Gly Leu Ile Leu Pro Ala Asn Met Asp Gly Val Pro Gly Leu Ser
        115                 120                 125

ttc gac ggc atc cat ccg ggc gaa agc tac gtg tac cgc ttc cgg gtc      432
Phe Asp Gly Ile His Pro Gly Glu Ser Tyr Val Tyr Arg Phe Arg Val
    130                 135                 140

ggg cag tcg ggc acg tac tgg tat cac agc cat tcg atg ttc cag gaa      480
Gly Gln Ser Gly Thr Tyr Trp Tyr His Ser His Ser Met Phe Gln Glu
145                 150                 155                 160

cag gcc ggg ctg tac ggc gcg atc gtg atc gat ccg cgc gaa ccg gcg      528
Gln Ala Gly Leu Tyr Gly Ala Ile Val Ile Asp Pro Arg Glu Pro Ala
                165                 170                 175

ccg ttc cac ttc gat cgc gag cat gtg ctg ctg ctg tcg gac tgg acc      576
Pro Phe His Phe Asp Arg Glu His Val Leu Leu Leu Ser Asp Trp Thr
            180                 185                 190

gac atg gac ccg gcg gcg ctg ttc cgg cgc ctg aaa aag atg tcg agt      624
Asp Met Asp Pro Ala Ala Leu Phe Arg Arg Leu Lys Lys Met Ser Ser
        195                 200                 205

tac gac aac tac gcc aag cgc acg gtc ggc gat ttc atg cgc gac gcg      672
Tyr Asp Asn Tyr Ala Lys Arg Thr Val Gly Asp Phe Met Arg Asp Ala
    210                 215                 220

cgc gaa cgc ggg ctg gcc gcg acc ctg cgc gat cgc ggc gaa tgg ggc      720
Arg Glu Arg Gly Leu Ala Ala Thr Leu Arg Asp Arg Gly Glu Trp Gly
```

-continued

```
225                 230                 235                 240

cgc atg cgc atg acc ccg acc gat ctg tcc gac gtc aac ggc aac acc      768
Arg Met Arg Met Thr Pro Thr Asp Leu Ser Asp Val Asn Gly Asn Thr
                245                 250                 255

tac acc tac ctg ctc aac ggc gcc gcg ccg gcc ggc aac tgg acc ggg      816
Tyr Thr Tyr Leu Leu Asn Gly Ala Ala Pro Ala Gly Asn Trp Thr Gly
            260                 265                 270

ctg ttc cgt ccg ggc gaa aag gtg ttg ctg cgt ttc atc aac ggc tcg      864
Leu Phe Arg Pro Gly Glu Lys Val Leu Leu Arg Phe Ile Asn Gly Ser
        275                 280                 285

gcg atg acc tac ttc gac gtg cgc att ccc ggt ttg aag atg acc gtg      912
Ala Met Thr Tyr Phe Asp Val Arg Ile Pro Gly Leu Lys Met Thr Val
    290                 295                 300

gtc gcc gcc gac ggc cag tac atc cat ccg gtc acg gtc gac gaa ttc      960
Val Ala Ala Asp Gly Gln Tyr Ile His Pro Val Thr Val Asp Glu Phe
305                 310                 315                 320

cgc atc gcg gtg gcc gaa acc ttc gac gtg ctg gtc gaa ccg gcc ggc     1008
Arg Ile Ala Val Ala Glu Thr Phe Asp Val Leu Val Glu Pro Ala Gly
                325                 330                 335

cag gac gcg tac acc atc ttc gcc cag gac aac ggc cgc acc ggc cat     1056
Gln Asp Ala Tyr Thr Ile Phe Ala Gln Asp Asn Gly Arg Thr Gly His
            340                 345                 350

gcg cgc ggc acc ctg gcg gtg cgc gaa ggc ctg cag gcc gag gta ccg     1104
Ala Arg Gly Thr Leu Ala Val Arg Glu Gly Leu Gln Ala Glu Val Pro
        355                 360                 365

ccg cac gat ccg cgg ccg ttg ctg acc atg gac gac atg ggc cat ggc     1152
Pro His Asp Pro Arg Pro Leu Leu Thr Met Asp Asp Met Gly His Gly
    370                 375                 380

ggc atg ggc ggc atg gat cac ggc gcg atg ggg ggc ggt cac gac atg     1200
Gly Met Gly Gly Met Asp His Gly Ala Met Gly Gly Gly His Asp Met
385                 390                 395                 400

agc aag atg aaa ggc atg gaa ggc ggt tgc ggc gcg aac atg ggc atg     1248
Ser Lys Met Lys Gly Met Glu Gly Gly Cys Gly Ala Asn Met Gly Met
                405                 410                 415

gcc ggc atg gat cac ggc gcg atg cag cac ggc gcc gcg gcc gcg ccc     1296
Ala Gly Met Asp His Gly Ala Met Gln His Gly Ala Ala Ala Ala Pro
            420                 425                 430

gcc aag ggc gac gaa cgc ctg atc gac atg cgc gcg atg gcg acc tcg     1344
Ala Lys Gly Asp Glu Arg Leu Ile Asp Met Arg Ala Met Ala Thr Ser
        435                 440                 445

ccc aag ctc gac gac ccg ggc atc ggc ctg cgc aac aac ggc cgc aag     1392
Pro Lys Leu Asp Asp Pro Gly Ile Gly Leu Arg Asn Asn Gly Arg Lys
    450                 455                 460

gtg ctg act tat agc gac ctg cgc agt gtg ttc gac gat ccc gat ggt     1440
Val Leu Thr Tyr Ser Asp Leu Arg Ser Val Phe Asp Asp Pro Asp Gly
465                 470                 475                 480

cgc gag ccg agc cgc gag atc gag ctg cac ctg acc ggc cac atg gag     1488
Arg Glu Pro Ser Arg Glu Ile Glu Leu His Leu Thr Gly His Met Glu
                485                 490                 495

aaa ttc gca tgg tcg ttc gac ggc cag aaa ttc atg ggc gcc gag ccg     1536
Lys Phe Ala Trp Ser Phe Asp Gly Gln Lys Phe Met Gly Ala Glu Pro
            500                 505                 510

atc cgc ctg acc tac ggc gag cgc atg cgc atc gtc ctg gtc aac gac     1584
Ile Arg Leu Thr Tyr Gly Glu Arg Met Arg Ile Val Leu Val Asn Asp
        515                 520                 525

acc atg atg acc cac ccg atc cat ctg cac ggt ctg tgg agc gat ctg     1632
Thr Met Met Thr His Pro Ile His Leu His Gly Leu Trp Ser Asp Leu
    530                 535                 540

gag aac gag gcc ggc gag ttc cag gtg cgc aag cac acc atc gac atg     1680
```

```
Glu Asn Glu Ala Gly Glu Phe Gln Val Arg Lys His Thr Ile Asp Met
545                 550                 555                 560

ccg ccg gga acg cgg cgc agc tac cgc gtg cgc gcc gat gcg ctc ggc      1728
Pro Pro Gly Thr Arg Arg Ser Tyr Arg Val Arg Ala Asp Ala Leu Gly
                565                 570                 575

cgc tgg gcc tac cac tgc cac ctg ctg tac cac atg gaa gcc ggg atg      1776
Arg Trp Ala Tyr His Cys His Leu Leu Tyr His Met Glu Ala Gly Met
            580                 585                 590

atg cgc gaa gtg agg gtc gag gaa                                      1800
Met Arg Glu Val Arg Val Glu Glu
        595                 600


<210> SEQ ID NO 4
<211> LENGTH: 600
<212> TYPE: PRT
<213> ORGANISM: Lysobacter capsici

<400> SEQUENCE: 4

Met Asn Arg Phe Phe Ser Asp Asp Gly Gly Ala Ser Ile Asp Ala Gly
1               5                   10                  15

Arg Arg Arg Phe Val Thr Gly Leu Ala Val Gly Gly Leu Ala Ala Gly
            20                  25                  30

Ser Gly Leu Trp Arg Ser Ala Tyr Ala Ala Pro Ala Leu Ala Gly Ala
        35                  40                  45

Pro Gln Val Leu Ser Gly Thr Glu Phe Asp Leu Ser Ile Gly Ser Ser
    50                  55                  60

Leu Ala Asn Phe Thr Gly Lys Thr Arg Pro Ala Ile Thr Val Asn Gly
65                  70                  75                  80

Ser Leu Pro Ala Pro Ile Leu Arg Trp Arg Glu Gly Asp Thr Val Thr
                85                  90                  95

Leu Arg Val Ala Asn Arg Leu Ala Glu Gly Met Ser Ser Ile His Trp
            100                 105                 110

His Gly Leu Ile Leu Pro Ala Asn Met Asp Gly Val Pro Gly Leu Ser
        115                 120                 125

Phe Asp Gly Ile His Pro Gly Glu Ser Tyr Val Tyr Arg Phe Arg Val
    130                 135                 140

Gly Gln Ser Gly Thr Tyr Trp Tyr His Ser His Ser Met Phe Gln Glu
145                 150                 155                 160

Gln Ala Gly Leu Tyr Gly Ala Ile Val Ile Asp Pro Arg Glu Pro Ala
                165                 170                 175

Pro Phe His Phe Asp Arg Glu His Val Leu Leu Leu Ser Asp Trp Thr
            180                 185                 190

Asp Met Asp Pro Ala Ala Leu Phe Arg Arg Leu Lys Lys Met Ser Ser
        195                 200                 205

Tyr Asp Asn Tyr Ala Lys Arg Thr Val Gly Asp Phe Met Arg Asp Ala
    210                 215                 220

Arg Glu Arg Gly Leu Ala Ala Thr Leu Arg Asp Arg Gly Glu Trp Gly
225                 230                 235                 240

Arg Met Arg Met Thr Pro Thr Asp Leu Ser Asp Val Asn Gly Asn Thr
                245                 250                 255

Tyr Thr Tyr Leu Leu Asn Gly Ala Ala Pro Ala Gly Asn Trp Thr Gly
            260                 265                 270

Leu Phe Arg Pro Gly Glu Lys Val Leu Leu Arg Phe Ile Asn Gly Ser
        275                 280                 285

Ala Met Thr Tyr Phe Asp Val Arg Ile Pro Gly Leu Lys Met Thr Val
    290                 295                 300
```

```
Val Ala Ala Asp Gly Gln Tyr Ile His Pro Val Thr Val Asp Glu Phe
305                 310                 315                 320

Arg Ile Ala Val Ala Glu Thr Phe Asp Val Leu Val Glu Pro Ala Gly
                325                 330                 335

Gln Asp Ala Tyr Thr Ile Phe Ala Gln Asp Asn Gly Arg Thr Gly His
            340                 345                 350

Ala Arg Gly Thr Leu Ala Val Arg Glu Gly Leu Gln Ala Glu Val Pro
        355                 360                 365

Pro His Asp Pro Arg Pro Leu Leu Thr Met Asp Asp Met Gly His Gly
    370                 375                 380

Gly Met Gly Gly Met Asp His Gly Ala Met Gly Gly Gly His Asp Met
385                 390                 395                 400

Ser Lys Met Lys Gly Met Glu Gly Gly Cys Gly Ala Asn Met Gly Met
                405                 410                 415

Ala Gly Met Asp His Gly Ala Met Gln His Gly Ala Ala Ala Ala Pro
            420                 425                 430

Ala Lys Gly Asp Glu Arg Leu Ile Asp Met Arg Ala Met Ala Thr Ser
        435                 440                 445

Pro Lys Leu Asp Asp Pro Gly Ile Gly Leu Arg Asn Asn Gly Arg Lys
    450                 455                 460

Val Leu Thr Tyr Ser Asp Leu Arg Ser Val Phe Asp Asp Pro Asp Gly
465                 470                 475                 480

Arg Glu Pro Ser Arg Glu Ile Glu Leu His Leu Thr Gly His Met Glu
                485                 490                 495

Lys Phe Ala Trp Ser Phe Asp Gly Gln Lys Phe Met Gly Ala Glu Pro
            500                 505                 510

Ile Arg Leu Thr Tyr Gly Glu Arg Met Arg Ile Val Leu Val Asn Asp
        515                 520                 525

Thr Met Met Thr His Pro Ile His Leu His Gly Leu Trp Ser Asp Leu
    530                 535                 540

Glu Asn Glu Ala Gly Glu Phe Gln Val Arg Lys His Thr Ile Asp Met
545                 550                 555                 560

Pro Pro Gly Thr Arg Arg Ser Tyr Arg Val Arg Ala Asp Ala Leu Gly
                565                 570                 575

Arg Trp Ala Tyr His Cys His Leu Leu Tyr His Met Glu Ala Gly Met
            580                 585                 590

Met Arg Glu Val Arg Val Glu Glu
        595                 600
```

<210> SEQ ID NO 5
<211> LENGTH: 1396
<212> TYPE: DNA
<213> ORGANISM: Lysobacter capsici

<400> SEQUENCE: 5

```
ggttaagcta cctgcttctg gtgcaacaaa ctcccatggt gtgacgggcg gtgtgtacaa     60

ggcccgggaa cgtattcacc gcagcaatgc tgatctgcga ttactagcga ttccgacttc    120

acggagtcga gttgcagact ccgatccgga ctgagatagg gtttctggga ttggcttgcc    180

ctcgcgggtt tgcagccctc tgtccctacc attgtagtac gtgtgtagcc ctggccgtaa    240

gggccatgat gacttgacgt catccccacc ttcctccggt ttgtcaccgg gggtctcctt    300

agagttccca ccattacgtg ctggcaacta aggacaaggg ttgcgctcgt tgcgggactt    360

aacccaacat ctcacgacac gagctgacga cagccatgca gcacctgtct cacggttccc    420
```

```
gaaggcacca atctatctct agaaagttcc gtggatgtca aggccaggta aggttcttcg    480
cgttgcatcg aattaaacca catactccac cgcttgtgcg ggcccccgtc aattcctttg    540
agtttcagtc ttgcgaccgt acttcccagg cggcgaactt aacgcgttag cttcgatact    600
gagagccaag ttgctcccaa catccagttc gcatcgttta gggcgtggac taccagggta    660
tctaatcctg tttgctcccc acgctttcgt gcctcagtgt cagtgctggt ccaggtagtc    720
gccttcgcca cagatgttcc tcccgatatc tacgcatttc actgctacac cgggaattcc    780
actaccctct accgcactct agtcagccag tttccaatgc cattcccagg ttgagcccag    840
ggctttcaca tcagacttaa caaaccacct acgcacgctt tacgcccagt aattccgagt    900
aacgcttgca cccttcgtat taccgcggct gctggcacga agttagccgg tgcttattct    960
tccggtaccg tcatgacctc agggtattaa cccaaggctt ttctttccgg acaaaagtgc   1020
tttacaaccc gaaggccttc ttcacacacg cggcatggct ggatcaggct tgcgcccatt   1080
gtccaatatt ccccactgct gcctcccgta ggagtctgga ccgtgtctca gttccagtgt   1140
ggctgatcat cctctcagac cagctacgga tcgtcgcctt ggtgggcctt taccccgcca   1200
actagctaat ccgacgtcgg ctcatctatc tgcgcgaagc ccgaaggtcc tccgctttca   1260
cccgtaggtc gtatgcggta ttagcgtaag tttccctacg ttatccccca caaataggca   1320
gattccgacg tattcctcac ccgtccgcca ctcgccaccc aaggagcaag ctcctctgtg   1380
ctgccgttcg actgca                                                   1396
```

<210> SEQ ID NO 6
<211> LENGTH: 1548
<212> TYPE: DNA
<213> ORGANISM: Lysobacter capsici

<400> SEQUENCE: 6

```
atggcaagca cccagctcaa cccgtccgaa atcagtgaac tgatcaagac ccgcatcgag     60
aaggtcaagc tggccgccga agcgcgcaac gaaggcaccg tcacctcggt gtccgacggc    120
atcgtgcgca tccacggcct ggctgacgtg atgcagggcg aaatgatcga actgccgaac    180
aacaccttcg cgctcgcgct gaacctggag cgcgactcgg tcggcgccgt ggtcctgggc    240
gattacgagc acctgcgcga aggcgacatc gccaagacca ccgcgcgcat cctggaagtg    300
ccggtcggtc gcgaactgct cggccgcgtg gtcaacgcgc tcggcgagcc gatcgacggc    360
aagggtccga tcggcgcggc gatgaccgct ccggtggagc gcgtcgcccc gggcgtgatc    420
tggcgcaagt cggtcgatca gccggtgcag accggttaca agaccgtcga cgcgatgatc    480
ccgatcggcc gcggccagcg cgagctgatc atcggcgacc gtcagaccgg caagaccgcg    540
ctggcgatcg acgcgatcat caaccagaag ggcaccggca ttaagtgcgt gtacgtcgcg    600
atcggccaga aggccagctc ggtcgccaac gtcgtgcgca agctggaaga aaacggcgcg    660
ctcgcccaca ccatcgtggt cgccgcgacc gcgtcggaat cggccgcgat gcagtacatc    720
agcgcctact cgggctgcac catgggcgag tacttcctcg accgcggcga agacgcgctg    780
atcgtgtacg acgatctgtc caagcaggcc gtggcctacc gccagatctc gctgctgctc    840
aagcgcccgc cgggtcgcga agcctatccg ggcgacgtgt tctacctgca cagccgcctg    900
ctcgagcgcg ccgcgcgcgt gtcgaccgag tacgtcgaga agttcaccaa cggcgaagtg    960
aagggcaaga ccggttcgct gaccgcgctg ccgatcatcg aaacccaggc cggcgacgtt   1020
tcggcgttcg tgccgaccaa cgtgatctcg atcaccgacg gccagatctt cctggaaacc   1080
```

-continued

```
gacctgttca acgccggcat ccgcccggcc gtgaacgccg gtatctcggt gtcgcgcgtc   1140

ggtggcgcgg cccagaccaa gatcgtcaag aagctgtccg gcggcatccg tatcgccctg   1200

gcccagtacc gcgagctggc tgcgttcgcg cagttcgctt ccgacctcga cgaagccacc   1260

cgcaagcagc tcgagcgcgg tcagcgcgtc accgagctga tgaagcagaa gcagtacgcg   1320

ccgatgtcga tcgccctgca gtcgctgtcg atctacgcgg tcgacaaggg cttcatggac   1380

gacgtgccgg tgaacaagat cggtgcgttc gaagaagcgc tgcacgcgca cttcaccaat   1440

accgccggcg agctggtcga tcagatcaac gccaccggca attggaacga cgacatcgaa   1500

ggcgccttca agaagggcat cgaagagttc aagcagaccg ggacctgg               1548
```

<210> SEQ ID NO 7
<211> LENGTH: 1425
<212> TYPE: DNA
<213> ORGANISM: Lysobacter capsici

<400> SEQUENCE: 7

```
atgagcagcc agggcaagat cgttcagatc atcggtgcgg tcgtcgacgt cgagttcgca     60

cgcgagtcgg ttccgcgcgt gtacgacgcg ttgaaggtcg agaacaccgc catcaccctc    120

gaagtgcagc agcagctggg cgacggcatc gtgcgcgcga tcgcgctcgg ttccaccgac    180

ggtctcaagc gcaacctggt ggcgatcaac accggcaagg gcgtgtcggt gccggtcggc    240

gcgggcaccc tgggccgcat catgaacgtg ctcggcgagc cgatcgacga agccggtccg    300

gtcgaagcca ccgagcattg ggaaatccac cgcgcggcgc ccgattacgc cgaccagtcc    360

tcgggcaacg agctgctgga aaccggcatc aaggtcatcg acctgatgtg cccgttcgcc    420

aagggcggca aggtcggcct gttcggcggc gccggcgtgg gcaagacggt caacatgctt    480

gagctgatca acaacatcgc caccgagcat gccggtctgt cggtgttcgc cggcgtcggc    540

gagcgcaccc gcgaaggcaa cgacttctac cacgagatgg ccgaagccgg cgtcatccag    600

ctcgagagcc tgaaggactc gaaggtcgcg atggtgtacg gccagatgaa cgagccgccg    660

ggcaaccgcc tgcgcgtcgc gctgaccggc ctgaccatgg ccgaatactt ccgcgacgaa    720

aaggacgccg acggcaaggg ccgcgacgtg ctgttcttcg tcgacaacat ctaccgctac    780

accctggccg gcaccgaagt gtcggcgctg ctcggccgca tgccgtcggc ggtgggttac    840

cagccgaccc tggccgagga aatgggcgtt ctgcaggagc gcatcacctc gaccaagacc    900

ggctcgatca cctcgatcca ggccgtgtac gtgcccgccg acgacttgac cgacccctcg    960

cccgcgacca ccttcgccca cctcgacgcc accgtcgtgt tgagccgtaa catcgcctcg   1020

ctgggtatct acccggcggt cgatccgctc gactcgacct cgcgtcagct cgacccgaac   1080

gtgatcggcg ccgagcacta cgacaccgcg cgccgcgtcc aggccacctt gcagaagtac   1140

aaggagctca aggacatcat cgcgatcctc ggcatggacg agctgtcgga agaagacaag   1200

caggccgtgt cgcgcgcgcg caagatcgag cgtttcttct cgcagccgtt ccacgtcgcc   1260

gaagtgttca ccggcgcccc gggcaagtac gtgtcgctga aggacacgat ccgcggcttc   1320

aagggcatct gcgacggcga atacgaccac ctgccggagc aggcgttcta catggtcggc   1380

ggcatcgagg aagcggtcga gaaggccaag aagatgggcg tgggc                   1425
```

<210> SEQ ID NO 8
<211> LENGTH: 1128
<212> TYPE: DNA
<213> ORGANISM: Lysobacter capsici

<400> SEQUENCE: 8

```
gtgacccaac ccgcaatcct cgcactcgaa gacggcaccg tgttcgaggg cgtttccgta     60
ggcgcgcccg gcctcagcgt cggcgaagtc gtattcaaca ccgcgatcac cggctaccag    120
gaaatcctca ccgatccttc gtacgcccgt cagctggtca cgctgaccta cccgcacgtc    180
ggcaacaccg gcatcaccgc gcaggacgac gaagccagcc aagtctgggc ctcgggcctg    240
atcgtgcgcg acgtgccgcg ccgcccccagc aactggcgca gcacgatcgc gctgccgcag    300
tggctggccg atcgcggcgt ggtcgcgatc tccgacatcg acacccgcaa gctgacccga    360
ttgctgcgcg acaccggcgc ccagaacggc gcgctgatgg ccggcgagat cgacgtcgcc    420
aaggcgatcg aagccgcgcg caagttcccg ggcctgaagg gcatggacct ggccaaggaa    480
gtctgcacgc gcgaacgtta cgagtggacc gaaggtcagc tcgacctcga ccgcaacgcg    540
ttcgtgaatg cgcaatcgcg ttttcatgtg gttgcctacg acttcggcgt caagctcaac    600
atcctgcgca tgctcgccga gcgcggctgc cgggtgaccg tggtgccggc gcagacctcg    660
gccgccgagg tgctggcgct caagcccgat ggcgtgttcc tgtccaacgg ccccggcgat    720
ccggagcctt gcgactacgc gatcgcggcg atcaaggaat tcctcgcgca aaagatcccg    780
accttcggca tctgcctggg ccatcagctg ctcggcctgg cctccggcgc caagaccctg    840
aagatgaagt tcggccatca cggcgcgaac catccggtcc aggacctcga cagcggccgg    900
gtgatgatca cctcgcagaa ccacggcttc gcggtcgatg aggccagcct gccggccaac    960
gtgcgcgtga cccaccgctc gctgttcgac ggcagcaatc agggcatcgc cctgaccgac   1020
gcgccggctt tcagtttcca gggccacccg gaagcgagcc cgggcccgca cgatgtgtcg   1080
ccgttgttcg atcggttcgt ggtgtcgatg gaacaggcca aggccgcc                1128
```

<210> SEQ ID NO 9
<211> LENGTH: 2481
<212> TYPE: DNA
<213> ORGANISM: Lysobacter capsici

<400> SEQUENCE: 9

```
atgaccaaca ccgagcacga cccctcgact gaatcggcca ccggttcgac cccgccgcaa     60
agcgcgcaaa ccccgcagac ctacgactcg agcaagatca ccgtcctgcg cggcctcgag    120
gcggtgcgca agcgcccggg catgtacatc ggcgatgtcc acgacggtac cggcctgcat    180
cacatggtct tcgaggtggt cgacaacgcg atcgacgagg ccctcgccgg ccacgccgac    240
gatgtggtgg tgaccttgca cgaagacggt tcggtctcct gctacgacaa cggccgcggc    300
atcccggtcg atatccacaa ggaagaaggc gtgtcggcgg ccgaggtgat cctcaccgtg    360
ctgcacgccg gcggcaagtt cgacgacaac agctacaaag tctccggcgg cctgcacggc    420
gtgggcgtgt cggtggtcaa cgcgctgtcc gagcacctgt ggctcaacat ctggcgcgac    480
ggtttccatc accagcagga atacgcgctc ggcgagccga tctatccgct caagcagctg    540
gaagcctcga ccaagcgcgg caccctgctg cgcttcaagc cggcggtgga aatcttcacc    600
gacgtcgagt tccactacga catcctggcc aagcgcctgc gcgagctgtc gttcctcaac    660
tcgggcgtca agatcactct ggtcgacgag cgcggcgaag gccgccgcga cgtgttccag    720
tacgagggcg ggatccgttc cttcgtcgag catctggccc aggtcaagac gccgctgcac    780
ccgaacgtga tctcggtgtc gggcgaaatg aacggcatca ccgtcgacgt ggcgttgcag    840
tggaccgatt cctaccagga aacgatgttc tgcttcacca acaacatccc gcagaaagac    900
ggcggcaccc acctgatcgg tttccgcgcc gcgctgaccc gcacgctggc cacttacatc    960
```

gagaagaccg gcgcggccaa gcagtccaag atcgcgctgt cgggcgagga catgcgcgaa 1020
ggcatgatcg cggtgctgtc ggtcaaggtg cccgatccga gcttttcctc gcagaccaag 1080
gaaaaactgg tcagttccga ggtgcgcccg gtcgttgaga acacgttcgg tacacgtttg 1140
gaggagttcc tgcaagaaca ccccaacgaa gcgcgtgcga tcaccagcaa gatcatcgag 1200
gcggcgaccg cccgcgaagc cgcgcgcaag gcgcgcgacc tgacccgccg caagggcgcg 1260
ctcgacatcg ccggcctgcc cggcaagctc gccgactgcc aggaaaaaga cccggccaag 1320
tccgaactgt tcatcgtcga gggcgactcc gccggcggct cggccaagca aggccgtaat 1380
cgcaagaccc aagcgatcct gccgctcaag ggcaagatcc tcaacgtcga acgcgcgcgt 1440
ttcgatcgca tgctcggcag cgccgaagtc ggcaccttga tcaccgcgct gggcaccggc 1500
atcggcaagg acgagtacaa cccggacaag ctgcgttatc accgcatcat cctgatgacc 1560
gacgccgacg tcgacggctc gcacatccgc accttgctgc tgacgttctt ctaccggcag 1620
atgcccgagc tgatcgagcg cggccacatc tacatcggcc tgccgccgct gtacaagatc 1680
aagcagggca agaacgaaat ttatctcaag gacgacgcgg cgctggatca gtacctggcc 1740
aacaacgcgg tcgaaggcgc ggcattgatc ccggcgaccg gcgagccgcc gatcgaaggc 1800
gcggcgctgg aaaaactgct gctcgcctac gccggcgcgc gcgagaccat cgcgcgcaac 1860
tcgcatcgct acgatcccaa cgtgctgcag gcgctgatcg atttcacccc gctcgatacc 1920
gagcacctgc tggccaacgt cgatgagcgg cacgaactcg acgccctgga aaagcgcctc 1980
aaccagaccg gactgggcaa gccgcgctac gcgctgcagc tgcatccggc caacgagacg 2040
cgccaggcgg cgctgctggt cacccgcacc cacatgggcc agcaactgat ccaggtgctg 2100
ccgttgtcgg cgttcgaagg cggcgaactg cgttcgctgc gcgaggccgc ctcgatgctg 2160
cacggcctgg tgcgcgaagg cgcgcagatc atccgcggca atcgcgcgca gccgatcaac 2220
agcttcgctc aggcgcaggc ctggttgctc gaggaagcca agaagggccg cgcgatccag 2280
cgcttcaagg gcctgggcga aatgaacccc gagcagctgt gggacaccac ggtcaatccc 2340
gaaacgcgcc gtctgttgca ggtgcgcatc gaggacgccg tggcggccga ccagatcttc 2400
agcaccctga tgggcgatgt ggtcgaaccg cgccgcgagt tcatcgagga caacgcgctc 2460
aaggtctcca atctcgacgt c 2481

<210> SEQ ID NO 10
<211> LENGTH: 1023
<212> TYPE: DNA
<213> ORGANISM: Lysobacter capsici

<400> SEQUENCE: 10
atggacgaga acaagaagcg cgcccttacc gccgctctga gccagatcga caagcaattc 60
ggcaagggct cggtgatgcg catgggcgac cgcgcggtcg agatcaccga agtcatcggt 120
accggctcgc tgatgctcga catcgcgctg ggcatcggcg gcctgcccaa gggccgcgtg 180
gtcgagatct acggtccgga gtcctcgggc aagaccacct tgaccctgca ggccatcgcc 240
gaatgccaga agaagggcgg caccgccgcc ttcatcgacg ccgagcacgc gctcgacccg 300
atctatgccg ccaagctcgg cgtcaatgtc gacgacctgc tgctgtcgca gcccgacacc 360
ggcgaacagg cgctggaaat cgccgacatg ctggtgcgtt cggccgcggt cgacatcgtc 420
gtgatcgact cggtcgccgc gctgaccccg aaggccgaaa tcgaaggcga aatgggcgac 480
cagctgccgg gcctgcaggc ccgtctgatg agccaggcgc tgcgcaagct gaccggcaac 540
atcaagcgct cgggcaccct ggtggtgttc atcaatcagc tgcgcatgaa gatcggcgtg 600

```
atgatgccgg gccagagccc ggaagtgacc accggcggca acgcgctcaa gttctacgcc    660

tcggtgcgcc tggacatccg ccgcatcggc gcgatcaaga agggcgacga gatcatcggc    720

aaccagacca agatcaaggt cgtcaagaac aagctcgccc cgccgttcaa gcaggtcgtc    780

accgaaatcc tctacggcga aggcatctcg cgcgaaggcg aactgatcga catgggcgtg    840

gaagccaagc tggtcgagaa gtccggcgcc tggtacagct gcggcgacga gcgcatcggc    900

cagggcaagg aaaacgcccg ccagtacctc aaggaaaacc ccgagatggc ggcccgcctg    960

gaagcgacgc tgcgcgagaa gttcgtgccc agcgacgccc cgcgcgaaga agtcatcgag   1020

gac                                                                 1023
```

<210> SEQ ID NO 11
<211> LENGTH: 996
<212> TYPE: DNA
<213> ORGANISM: Lysobacter capsici

<400> SEQUENCE: 11

```
atgacggtta ccgccaatca ggtactgcgc ccgcgtggtc cgcagatcga acgcctcacc     60

ggcaatcgcg cgaaggtcgt gatcgagccg ctggagcgcg gttacggcca tacgctgggc    120

aacgcgctgc ggcgcgtgct gctgtcgtcg atcccgggtt tcgccatcac cgaggtcgaa    180

atcgatggcg tgctgcatga gtacaccacg gtcgaaggtc tggaagagga cgtgctggag    240

gttctgctga acctcaagga cgtcgccatc cgcatgcaca ccggcgacgc gtcgacgctg    300

tcgctggcca agcaaggtcc cggcatcgtc accgccggcg acatcaagac cgaccacaac    360

gtcgaaatcc tcaacaccga ccacgtgatc tgccacctga ccaaggatac ggcgatcaac    420

atgcgtctga agatcgaacg cggtttcggc taccagccgg cggcttcgcg ccgtcgtccg    480

gacgaagaaa cccgcgcgat cggtcgtctg atgctggacg cgagcttctc gccggtccgt    540

cgcgtcgcct acgcggtgga agccgcgcgc gtcgagcagc gcaccgatct cgacaagctg    600

gtgctggaca tcgaaaccaa cggcacgatc gacgccgagg aagccgtgcg caccgccgcc    660

gacatcctca ccgatcagct gtcggtgttc ggcgacttca cccaccgcga ccgcggtgcg    720

gcgaagccgg ccaccagcgg catcgatccg atcctgctgc gcccgatcga cgatctcgag    780

ctcaccgtgc gttcggccaa ctgcctcaag gccgagagca tctactacgt cggcgatctg    840

atccagaaga ccgaagtcga gctgctcaag accccgaacc tgggcaagaa gtcgctcacc    900

gagatcaagg aagtgctggc tcagcgcggc ctgtcgctcg gcatgaagct ggaaaactgg    960

ccgccggcgg gtatcgcctc gcacggaatg atgggg                              996
```

<210> SEQ ID NO 12
<211> LENGTH: 1863
<212> TYPE: DNA
<213> ORGANISM: Lysobacter capsici

<400> SEQUENCE: 12

```
atggccaacg aacgtcagcc ccctccgtcc gatatcaagc tcctgatcag caagggcttg     60

gagcagggct atctgaccta tgccgaggtc aacgatcacc tgcccgacga tctcgtcgac    120

gccgaacaga tcgaagacat catcggcatg atcaacggca tgggcatcga ggtgcatgaa    180

gttgcgcccg atgccgaaac gctgttgctc gccgacggca ataccggtaa ccgcgaagtc    240

gacgacaccg ccgctgaaga agccgcggcg gcgctgactg cgctcgacgg cgaaggcggc    300

cgtaccaccg acccggtgcg catgtacatg cgcgaaatgg gcacggtgga actgctgacc    360
```

-continued

```
cgcgaaggcg aaatcgccat cgccaagcgc atcgaagaag gcctcaacca ggtccaggct    420

tcgctcgctc tgttcccgtc caccatccag ctgatcctgg aggactacga aacccacaag    480

gccggcaaaa agcgcctggc cgagatcgtc gtgggcttca acgatcacct cgacgaagaa    540

cccgaaccgc cggcgccgcc ggtggtggta gccgaaaccg acgccgacgc ggacgacgac    600

gaagaagtcg aagccgccgg cgacgatgcc gacgccgagg aaaccacgtc cggccccgat    660

ccggtcgaag tcgccgcgcg catggaggcc atcgccgacc tgtacggcaa gttcgtcaag    720

gcccaggcca agaacggcgc cggccacaag accgtgacca agctgcgcga agacatcgcc    780

gcggtgttcg tcaccctcaa gctgccgctc gccctgaccg acagcctgat gcgcaacctg    840

cgcgacgtgg tcggttcgat caaggaccgc gagcgcaaga ttctggatct ggccacccgc    900

gtcgccaaga tgccgcgcaa ggatttcatc cgcgcgtggg aaggcaacca gaccaatctg    960

gaatgggtcg acgaactgct caagcgcaag cagaagtggt cgtcgggcct gcgcgacgtc   1020

aaggatcaga tcatcgtcga acagcagacg acgatcgaaa tcgaacaggc ctcgctgctg   1080

accttgaacg acatcaagga aatcagccgc gcgatggcct acggcgaggc caaggcgcgc   1140

aaggccaaga aggaaatggt cgaggccaac ctgcgtctgg tgatctcgat cgccaagaag   1200

tacaccaacc gcggcctgca gttcctcgat ctgatccagg aaggcaacat cggtctgatg   1260

aaggcggtcg acaagttcga attccgccgc ggcttcaagt tctcgaccta cgccacgtgg   1320

tggatccgtc aggccatcac ccgttcgatc gccgatcagg cccgcaccat ccgtatcccg   1380

gtgcacatga tcgagacgat caacaagctc aaccgcatct cgcgtcagat gctccagcag   1440

tacggccgcg aggccacgcc ggaagagctt gcgaaagaaa tggacatgcc cgaggacaag   1500

atccgcaagg tcatgaagat cgccaaggag cccatctcga tggaaactcc gatcggcgac   1560

gacgaagact cgcacctggg cgacttcatc gaggacacca acgtggagtc cccggtcgaa   1620

gccaccacca acatcaacct gtcggaaacg gtccgcgacg tgctcgccgg cctgaccccg   1680

cgcgaggcca aggtgttgcg catgcgtttc ggcatcgaca tgaacaccga tcacacgctg   1740

gaagaagtcg gcaagcagtt cgacgtgacc cgcgagcgca tccgtcagat cgaagcgaag   1800

gcgctgcgca agctgcgtca tccgagccgg tcggaacagc tgcgcagctt cctcgatatc   1860

gat                                                                 1863
```

<210> SEQ ID NO 13
<211> LENGTH: 2028
<212> TYPE: DNA
<213> ORGANISM: Lysobacter capsici

<400> SEQUENCE: 13

```
atggacgaca gtcagcagtc cgccggtttc cagctagttt cgccgtattc gccggccggc     60

gatcagccgc aggcgatcga caagctggtc gccggtttcg agggcggcct ggcccagcag    120

accctgctcg gcgtgaccgg ctcgggcaag acctacacca tcgccaacgt ggtccaggcg    180

gtgcagaagc cgaccctggt gatggcgccg aacaagaccc tggccgcgca gctgtacggc    240

gagttcaagg cgttctttcc gcacaacgcg gtcgagtact tcgtcagcta ctacgactac    300

taccagcccg aggcctacgt gccgtcgagc gacaccttca tcgagaagga cagctcggtc    360

aacgagcaca tcgagcagat gcggctgtcg gcgaccaagg ccctgctcga gcggcgcgac    420

gcgctgatcg tgtgcacggt ttcggcgatc tacggcctgg gcgatccgaa cgaatacttc    480

cgcatggtcc tgcacatggt ccgcggcgag cgcatcgacc agcgcgagct gatccgccgc    540

ctgaccgaga tgcagtacac ccgcaacgac accgaactgc gccgcgcgac ctaccgcgtg    600
```

-continued

```
cgcggcgaag tcatcgacgt gcatccggcc gaaagcgatt cgcaggcgct gcgcgtggag    660

ctgttcgacg gcgaaatcga aaacctgacc ctgttcgatc cgctgaccgg cgaaaccctg    720

gaacgggtgc cgcgcttcac catctacccc ggttcgcact acgtcaccac ccgccgcacc    780

gtgctcgacg cgatcgagac gatcaaggaa gagctgcgcg agcgcctgga atacctgtac    840

gcgaacaaca agctggtcga ggcgcagcgc ctggcccagc gcacccagtt cgaccttgag    900

atgctggccg aggtcggcta ctgcaacggc atcgagaact actcgcggca cctgagcggg    960

cacatgcccg gcgagccgcc gccgtgcctg ttcgactacc tgccgcccga cgcgctgctg   1020

gtggtcgacg aatcgcacgt caccattccg cagatcggcg cgatgtacaa aggcgaccgc   1080

tcgcgcaagg aaaccctggt cgagttcggt ttccgcatgc cctcggcgct ggacaaccgg   1140

ccgctgcggt tcgaagaatg ggaagggcgc tcgccgcgcg cgatctatgt ctcggccacg   1200

cccggtccgt atgaactgaa gaagtcggaa gggcagatca ccgagctggt ggtgcgtccg   1260

accggcctga tcgatccggt ggtcgagatc cgcccggtcg cgacccaggt cgacgacgtg   1320

ctcggcgaga tccgcgagcg cgtggcgatg ggcgatcgcg tgctgatcac caccctgacc   1380

aagcgcatgt cggaaaacct caccgaatac ctcggcgaac acgggatcaa ggtgcgctac   1440

ctgcattcgg acatcgagac cgtggagcgg gtcgagatca tccgcgacct gcgcctgggc   1500

aagttcgacg tgctggtcgg catcaacctg ctgcgcgagg gcctggacat gcccgaggtg   1560

tcgctggtcg cgatcctcga cgccgacaag gaaggtttcc tgcgttcgac cggttcgctg   1620

atccagacca tcggccgcgc cgcgcgcaac ctgcgcggca aggcgatcct gtacgccgac   1680

cgcatcacca actcgatgca gcgcgcgatc gaggaaaccg accgacgccg gcagaaacag   1740

gtcgagtaca acgaagccca cggcatcacc cctaagtcgg tcgacaaggc ggtggtcgac   1800

atcatggaag gcgcccgggt cgatcccgaa gcgctcaagg cgcgcggcaa gggccgtcgg   1860

gcgaccgagg acgcggcgga cgtcgcgagc ctcagcccgg cccagttcgc ggccaggatc   1920

aaggcgctgg agcagcagat gtaccagcac gcccgcgatc tggagttcga acaggccgcg   1980

gcggtgcgcg atcaactgcg caaactcaag gacgccggac tgggcgcc                2028
```

<210> SEQ ID NO 14
<211> LENGTH: 18
<212> TYPE: DNA
<213> ORGANISM: Artificial Sequence
<220> FEATURE:
<223> OTHER INFORMATION: primer

<400> SEQUENCE: 14

```
ggtgctgatc atcgcctg                                                   18
```

<210> SEQ ID NO 15
<211> LENGTH: 18
<212> TYPE: DNA
<213> ORGANISM: Artificial Sequence
<220> FEATURE:
<223> OTHER INFORMATION: primer

<400> SEQUENCE: 15

```
gggcgtcgtt gataccgt                                                   18
```

<210> SEQ ID NO 16
<211> LENGTH: 18
<212> TYPE: DNA
<213> ORGANISM: Artificial Sequence
<220> FEATURE:

-continued

```
<223> OTHER INFORMATION: primer

<400> SEQUENCE: 16

ggsasbtact ggtrbcac                                                    18


<210> SEQ ID NO 17
<211> LENGTH: 20
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (3)..(3)
<223> OTHER INFORMATION: n is a, c, g, or t

<400> SEQUENCE: 17

tgnghcatca tsgtrtcrtt                                                  20
```

BACTERIAL *LYSOBACTER CAPSICI* STRAIN AND USES THEREOF

FIELD OF THE INVENTION

The present invention relates to the field of plant protection products, particularly to biocontrol of plant pathogens, such as plant pathogenic fungi and oomycetes. The invention also relates to a novel bacterial strain *Lysobacter capsici*, uses thereof and methods employing same. The invention also relates to the combined use of compositions comprising copper (such as copper-containing plant protection products) and *Lysobacter capsici* bacteria in treating such pathogens, as well as to related methods.

BACKGROUND OF THE INVENTION

Downy mildew is one of the most serious grapevine (*Vitis vinifera*) diseases in the world. It is caused by the biotrophic oomycete *Plasmopara viticola*, which can attack all green parts of the grapevine (Gessler et al., 2011). These days, control of downy mildew relies mainly on frequent applications of chemical fungicides in conventional agriculture or copper in organic production (Wong et al., 2001; Gessler et al., 2011). Similarly, potato late blight and tomato late blight are serious plant diseases caused by the oomycete *Phytophthora infestans*, which is also routinely treated with e.g. fungicides as mentioned above (Fry and Goodwin, 1997; Mizubuti et al., 2007).

Growing concerns about the negative impact of chemical fungicides (chemical agents) and copper on agricultural soils are driving the search for new, low-impact, active components to e.g. control *Plasmopara viticola* and *Phytophthora infestans*. Certain microorganisms with favourable toxicological and eco-toxicological profiles offer potential solutions.

Although in recent years several bacterial strains have been selected for biological control of plant diseases caused by fungi and oomycetes (Lugtenberg and Kamilova, 2009), very few have been identified for the control of *Plasmopara viticola*. A strain of *Erwinia herbicola* has been shown to inhibit germination of *Plasmopara viticola* sporangia in vitro (Tilcher et al., 1994) and some bacterial strains belonging to *Erwinia*, *Pseudomonas* and other genera have yielded promising results (Tilcher et al., 2002), but no follow-up studies on these bacteria have been reported in spite of the enormous efforts being made to find alternatives to chemical-based fungicides to control *Plasmopara viticola*. On the contrary, several scientific works were dealing with the evaluation of bacterial strains for the control of *Phytophthora infestans* (De Souza et al., 2003; Lourenco et al., 2006; Zakharchencko et al., 2011) but, at the moment, few are the bacteria-based plant protection products that can be exploited for the biocontrol of this plant pathogenic oomycete.

Certain bacteria of the genus *Lysobacter* have been brought in connection with e.g. soil suppressiveness, high production of lytic enzymes, or antibiotic production. Also, the genus *Lysobacter* (Christensen and Cook, 1978) includes bacterial species with a potential for biological control of plant pathogens (Hayward et al., 2010). Moreover, some *Lysobacter* strains have already been shown to actively protect plants from attack by soil-borne oomycetes. For example, *Lysobacter enzymogenes* strain 3.1T8, isolated from rockwool, inhibits mycelial growth of *Phytophthora capsici*, *Pythium ultimum* and *Pythium aphanidermatum* in vitro. Production of extracellular proteases, lipases and unidentified biosurfactants and antifungal molecules by *Lysobacter enzymogenes* strain 3.1T8 is involved in the control of infections caused by *Pythium aphanidermatum* on cucumber plantlets (Folman et al., 2003, 2004). *Lysobacter* sp. strain SB-K88 synthesises Xanthobaccin A, B and C, macrocyclic lactams which are highly effective in vitro against *Aphanomyces cochlioides*, *Phytophthora vignae* f. sp. *adzukicola* and *Pythium ultimum* (Nakayama et al., 1999). Application of strain SB-K88 and the compound Xanthobaccin A to the seeds of sugar beet suppressed damping-off in natural soil hosting populations of *Pythium* spp. (Homma et al., 1993; Nakayama et al., 1999). Furthermore, *Lysobacter* sp. SB-K88 directly antagonises the mycelium of *A. chloclioides* by directly attacking the cell wall of this oomycete (Islam et al., 2005). Strain YC5194, type strain of the species *Lysobacter capsici*, is closely related genetically to strain SB-K88 (Park et al., 2008; Puopolo et al., 2010). It was isolated from the rhizosphere of the pepper plant (*Capsicum annuum*) and inhibits the growth of *Pythium ultimum* and other phytopathogenic fungi in vitro (Park et al., 2008). Another member of this species, *Lysobacter capsici* strain PG4, reduces mycelial growth of several fungi and oomycetes in vitro and when applied to tomato seeds controls tomato foot and root rot caused by *Fusarium oxysporum* f. sp. *radicis-lycopersici* (Puopolo et al., 2010).

However, it has been difficult to find (new) bacterial antagonists to be used as plant protection products. The main reasons for failure in the selection of new bacterial antagonists are the poor survival rate of bacterial biocontrol agents on leaves and their incompatibility with copper-based fungicides, which does not, for example, allow microorganisms to be integrated into a low-dose copper-based strategy (Dagostin et al., 2011).

Accordingly, and despite extensive research and progress made so far, there remains a need for bacterial plant protection products with advantageous features such as persistence on plant leaves. Especially, there remains a need in the art for alternative or improved, respectively, treatments of fungal and oomycete diseases, such as diseases caused by *Plasmopara viticola* or *Phythophthora infestans*. This is particularly so in view of the various well-known advantages of plant protection products that include microorganisms when compared to standard (chemical) plant protection products, particularly if they are considered nonpathogenic and non-infectious to humans and animals. Further, there remains a need for identifying bacterial plant protection products that are compatible with standard (chemical) plant protection products such as copper-based plant protection products such that the use of such non-biological plant protection products can be decreased e.g. by employing combination treatments.

In view of the above, the present inventors identified a new *Lysobacter* strain, *Lysobacter capsici* AZ78, and explored the ability of *Lysobacter capsici* AZ78 to persist in the grapevine and tomato phyllosphere and at the same time to control e.g. *Plasmopara viticola* and *Phytophthora infestans* in vivo. In addition, the present inventors show that AZ78 is resistant to copper ions and can be applied together with copper-based fungicides/plant protection products in low doses to control grapevine downy mildew and tomato late blight. The present inventors also assessed its tolerance to abiotic stresses associated with starvation, high temperatures and UV irradiation. Based on these characteristics, *Lysobacter capsici* AZ78 may be exploited by means of new, integrated, disease-management strategies.

Accordingly, the present inventors have succeeded in finding new advantageous and effective bacteria of *Lysobacter capsici* species, which can be used to control various plant diseases. Moreover, with the present studies, the present inventors have surprisingly found that a new strain of *Lysobacter capsici* shows resistance to copper and, moreover, surprisingly allows an advantageous combination treatment of various pathogenic fungi and oomycetes.

SHORT DESCRIPTION OF THE FIGURES

FIG. 1: This figure depicts *Lysobacter capsici* AZ78 resistance to copper ions at different concentrations. *Lysobacter capsici* AZ78 resistance to copper ions is expressed as the logarithmic value of the survival ratio (log SR). SR was calculated as the ratio of the *Lysobacter capsici* AZ78 CFUs developed on LBA amended with copper sulphate at different concentrations to the *Lysobacter capsici* AZ78 CFU developed on LBA. Points with the same letters do not differ significantly according to Tukey's test ($\alpha$=0.01).

Figure 2A:
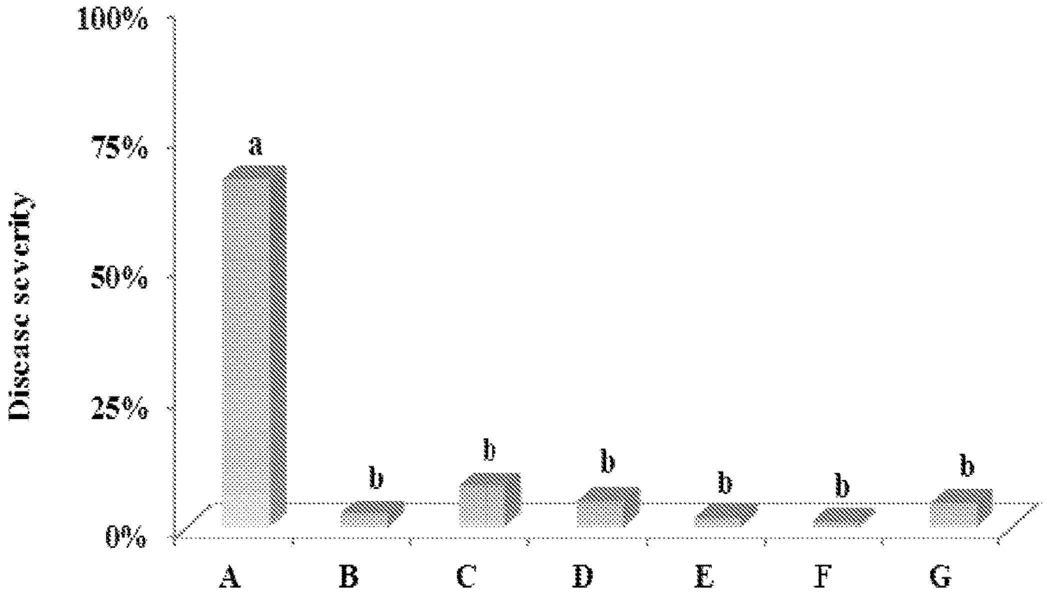
Figure 2B:
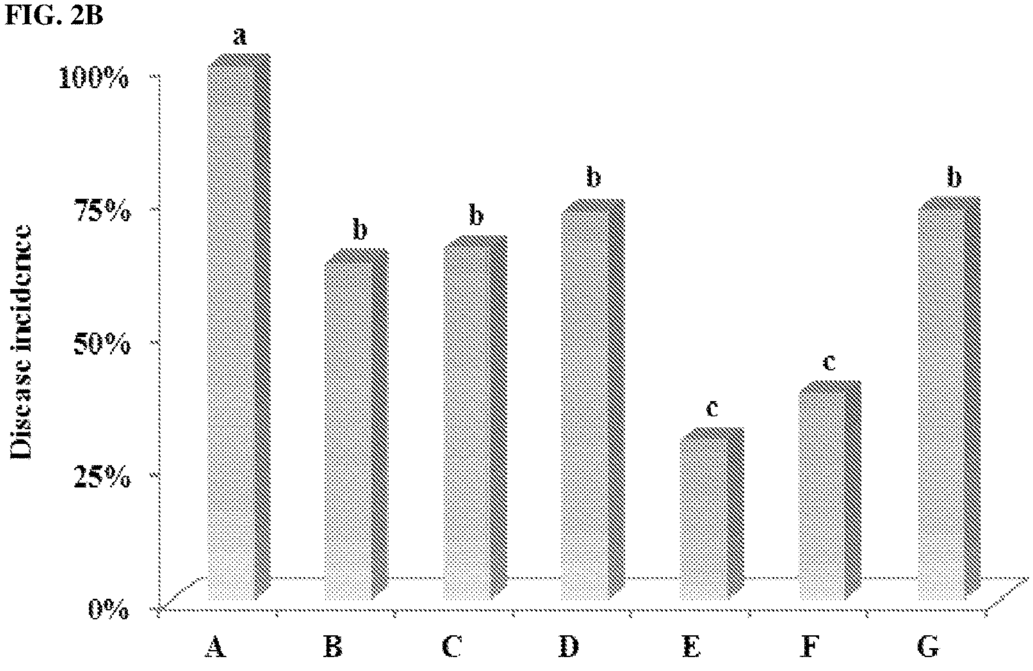

FIGS. 2A-B: This figure illustrates the ability of *Lysobacter capsici* AZ78 to control downy mildew on grapevine plants under controlled greenhouse conditions. *Lysobacter capsici* AZ78 in combination with a copper-based plant protection product (Kocide 3000) (general note: a copper-based plant protection product may be also referred to herein as a copper-based fungicide) at low dosages was also assessed in these experiments. The following treatments were applied: A) untreated; B) Kocide 3000 at 2.5 g $L^{-1}$; C) Kocide 3000 at 1.25 g $L^{-1}$; D) Kocide 3000 at 0.6125 g $L^{-1}$; E) *Lysobacter capsici* AZ78+Kocide 3000 at 1.25 g $L^{-1}$; F) *Lysobacter capsici* AZ78+Kocide 3000 at 0.6125 g $L^{-1}$; G) *Lysobacter capsici* AZ78. FIG. 2A shows the influence on disease severity; FIG. 2B shows the influence on disease incidence.

Figure 3A:
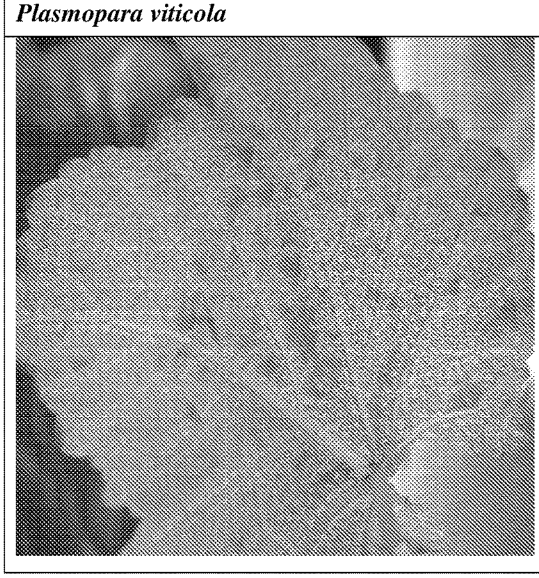
Figure 3A:
Figure 3B:
Figure 3B:

FIGS. 3A-B: This figure shows exemplary pictures of: FIG. 3A) Untreated grapevine plants and grapevine plants treated with *Lysobacter capsici* AZ78 for the control of *Plasmopara viticola*. FIG. 3B) Tomato plants with and without treatment against *Phytophthora infestans* using bacteria of *Lysobacter capsici* AZ78.

Figure 4A:
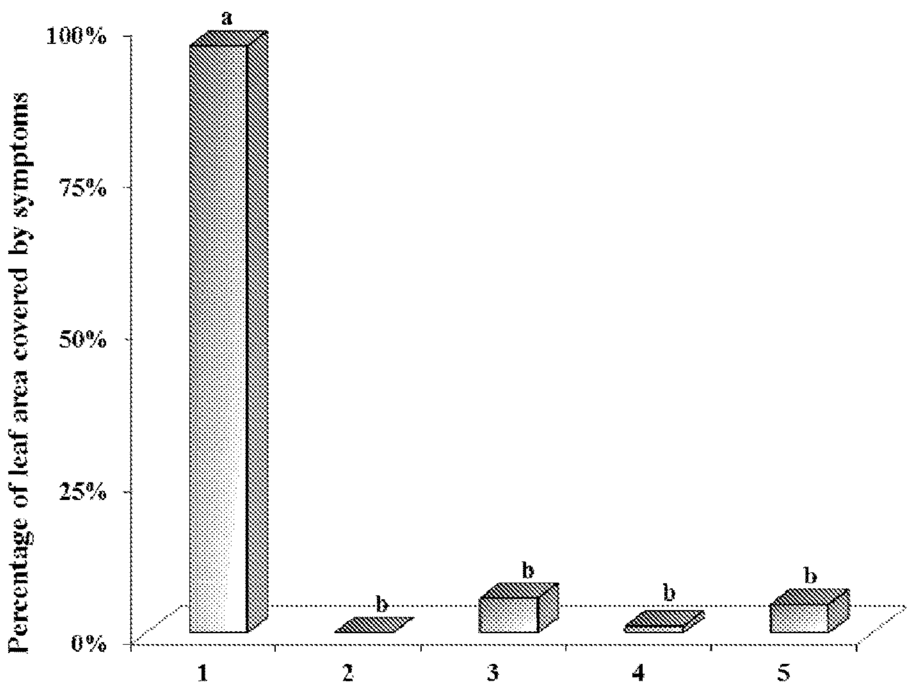
Figure 4B:
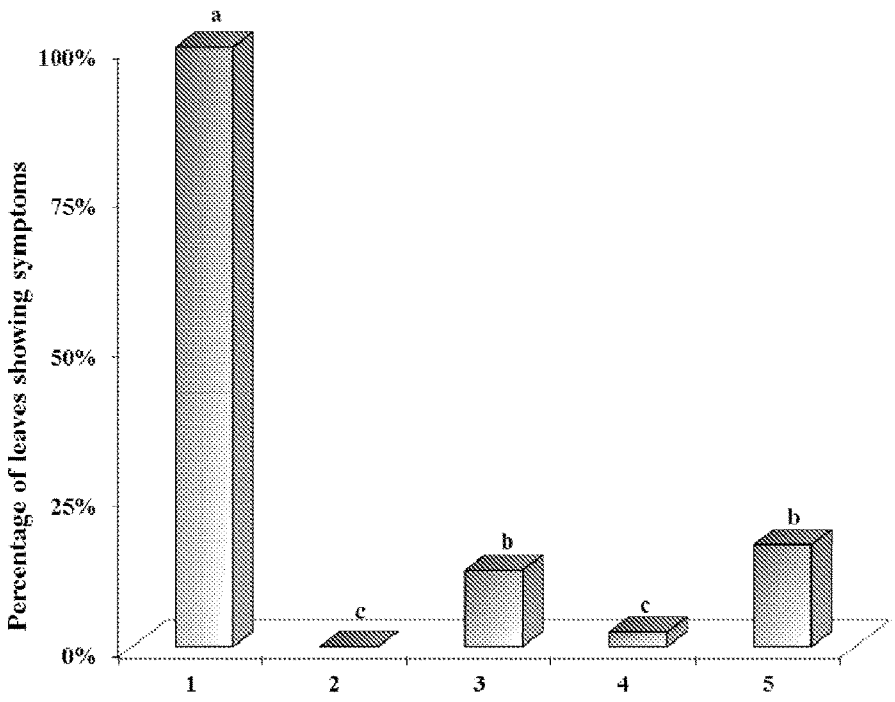

FIGS. 4A-B: This figure depicts the ability of *Lysobacter capsici* AZ78 alone and in combination with a copper-based fungicide to control late blight of tomato caused by *Phytophthora infestans*. The following treatments were applied: 1) untreated; 2) Kocide 3000 at 2.5 g $L^{-1}$; 3) Kocide 3000 at 0.6125 g $L^{-1}$; 4) *Lysobacter capsici* AZ78+Kocide 3000 at 0.6125 g $L^{-1}$; 5) *Lysobacter capsici* AZ78. FIG. 4A shows the influence on the percentage of leaf area covered by symptoms, and FIG. 4B shows the influence on the percentage of leaves showing symptoms.

Figure 5:
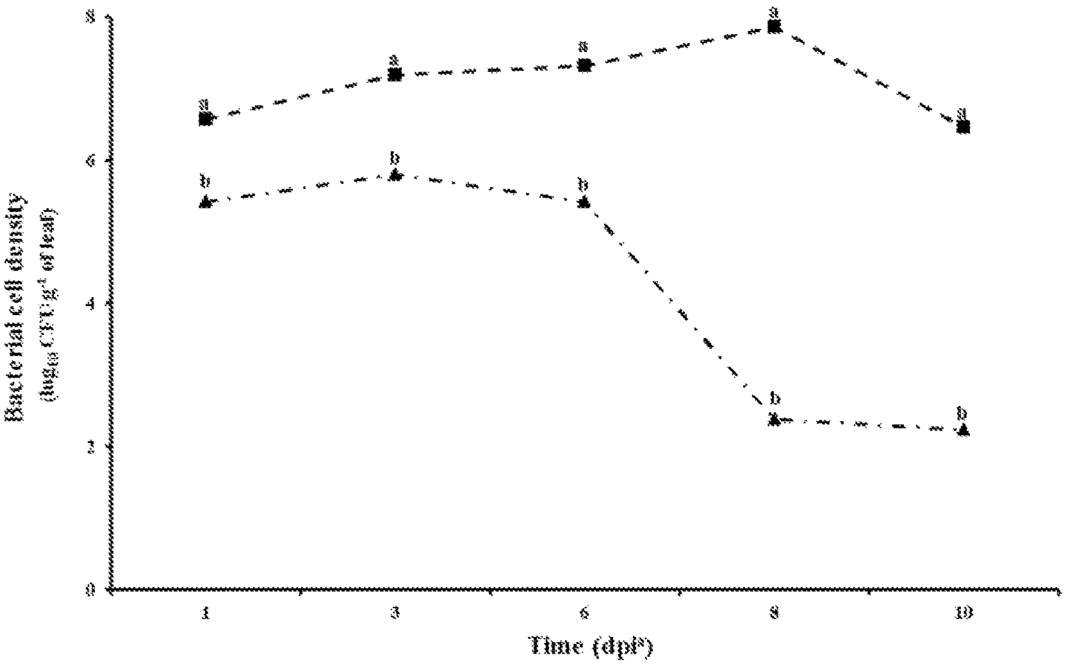

FIG. 5: This figure depicts *Lysobacter capsici* AZ78 persistence on grapevine leaves. The line with triangles represents persistence on plants maintained at 25° C. with 70±10% Relative Humidity (RH); the line with squares represents persistence on plants maintained at 25° C. with 90±10% RH. Bacterial cell density is expressed as $\log_{10}$ CFU $g^{-1}$ of leaf. Points with the same letters do not differ significantly according to Tukey's test ($\alpha$=0.01). [a]dpi=days post inoculation.

Figure 6A:
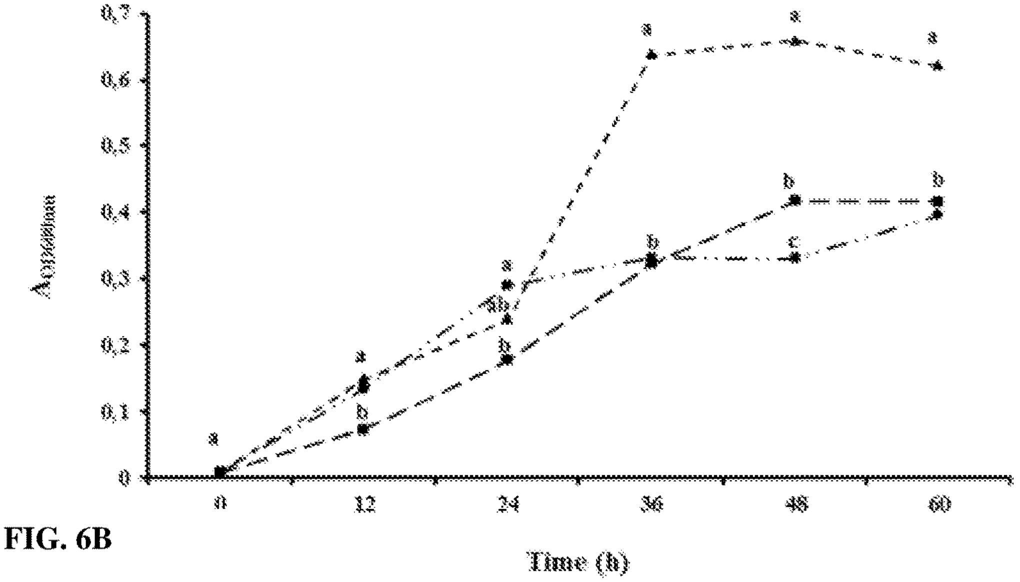
Figure 6B:
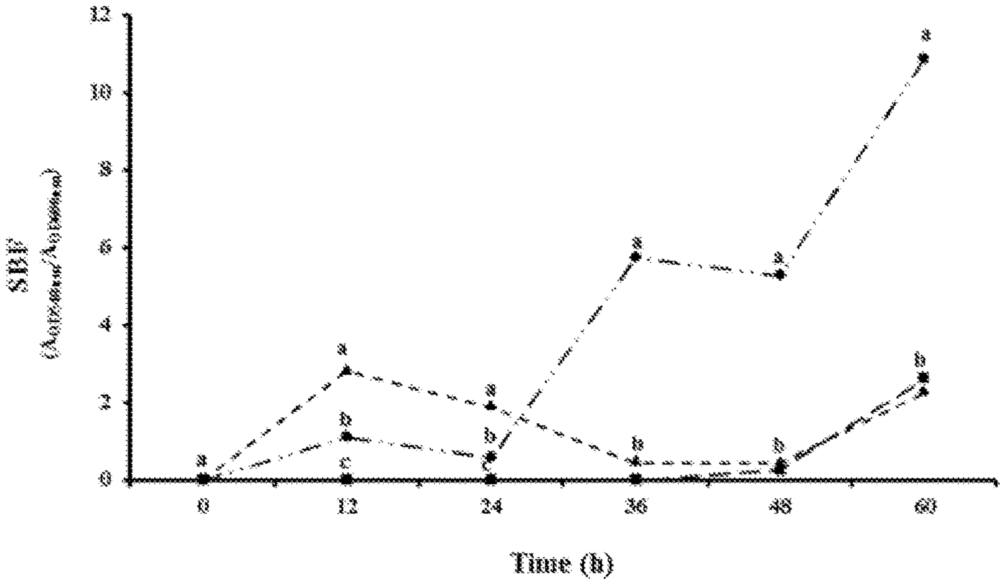

FIGS. 6A-B: This figure illustrates ability of *Lysobacter capsici* AZ78 to produce biofilm in different growth media. FIG. 6A) Bacterial cell density was monitored by scoring the $A_{OD600nm}$ value every twelve hours. FIG. 6B) Specific Biofilm Formation (SBF) was calculated as the ratio of adherent cells ($A_{OD540nm}$ value) to bacterial cell density ($A_{OD600nm}$ value). The liquid media were: KB (triangles), LB (squares) and NB (circles). Points with the same letters do not differ significantly according to Tukey's test ($\alpha$=0.01).

Figure 7A:
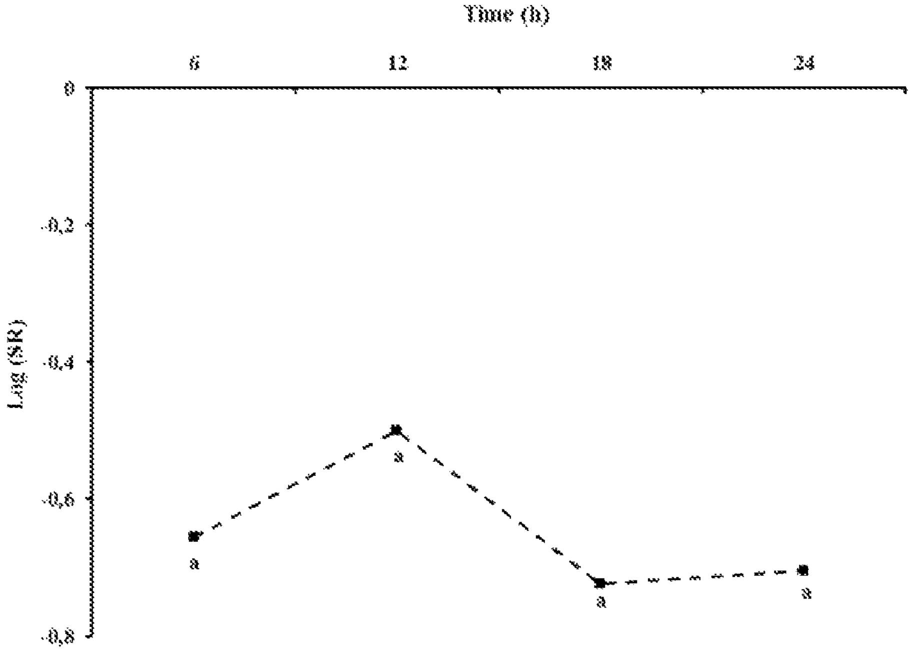
Figure 7B:
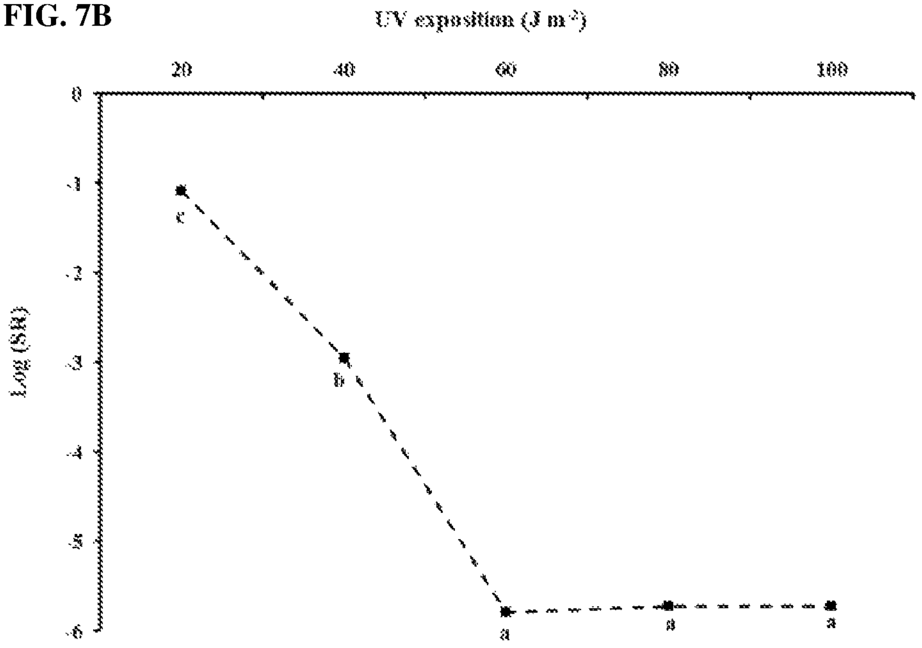

FIGS. 7A-B: This figure depicts *Lysobacter capsici* AZ78 resistance to abiotic stresses. FIG. 7A) Resistance to 24 h exposure to −20° C. FIG. 7B) Survival of *Lysobacter capsici* AZ78 cells exposed to increasing UV irradiation. The ability of *Lysobacter capsici* AZ78 to resist abiotic stresses is expressed as the logarithmic value of the survival ratio (Log SR). SR was calculated as the ratio of *Lysobacter capsici* AZ78 treated cells to *Lysobacter capsici* AZ78 untreated cells. Points with the same letters do not differ significantly according to Tukey's test ($\alpha$=0.01).

FIGS. 8A-M: This figure discloses various nucleic acid sequences related to the present invention. Among those, SEQ ID NOs 5-13 refer to preferred nucleic acid sequences of (housekeeping) genes of *Lysobacter capsici* AZ78 (in this order: 16S rDNA, atpA, atpD, carA, gyrB, recA, rpoA, rpoD and uvrB). These are e.g. suitable for comparative purposes in context with the invention. Among those, SEQ ID NOs 6-13 are particularly preferred sequences.

SUMMARY OF THE INVENTION

The present invention, among others, relates to a novel bacterial strain belonging to *Lysobacter capsici* species, *Lysobacter capsici* AZ78, bacteria of said bacterial strain, and bacterial preparations related thereto.

The present invention further relates to uses of the above for preparing a plant protection product—as well as to plant protection products comprising any of the above.

The present invention also relates to uses of the bacterial strains, bacteria or plant protection products of the invention for preventing or treating a plant disease—as well as corresponding methods of preventing or treating a plant disease.

The present invention further relates to kits of parts comprising *Lysobacter capsici* bacteria or strains or the like together with a composition comprising copper.

The present invention also relates to the use of a composition comprising copper in a method of preventing or treating a plant disease, wherein said composition is used in combination with *Lysobacter capsici* bacteria or strains or the like—as well as methods of preventing or treating a plant disease comprising steps of contacting a plant with a composition comprising copper and a step of contacting the plant with *Lysobacter capsici* bacteria or strains or the like.

The present invention further concerns certain isolated polypeptides that are related to the bacteria of the invention and that are involved in copper resistance—as well as to related nucleic acids.

Generally, the present invention predominantly relates to products, uses and methods as defined in the claims herein.

DETAILED DESCRIPTION OF THE INVENTION

The present inventors have performed numerous studies and have succeeded in solving the above problems.

Accordingly, the present invention, among others, provides novel *Lysobacter capsici* bacteria, particularly those of strain *Lysobacter capsici* AZ78 (herein also abbreviated as "AZ78").

Said novel bacteria of *Lysobacter capsici* AZ78 have several advantageous features. These include, but are not limited to the following: AZ78 belongs to a bacterial genus that does not encompass species associated with human diseases. It is the first case of a *Lysobacter* member able to control *Plasmopara viticola* and *Phytophthora infestans*. The reduction of disease severity is higher than that of other *Lysobacter* bacteria. AZ78 persists well on phyllosphere of crop plants. The physiological characteristics make AZ78 suitable for bio formulation.

Moreover, there are no expected adverse effects on humans or the environment deriving from the application of *Lysobacter capsici*. Accordingly, *Lysobacter capsici* is an environmentally friendly microbial biocontrol agent. The proposed taxonomic designation is *Lysobacter capsici* AZ78. The microorganism is not genetically modified.

Further advantages may e.g. be taken from further disclosure herein below including the Examples herein, and particularly also from the comments in Example 8 herein below.

Specifically, in a first aspect, the present invention concerns a bacterial strain, selected from the group consisting of i) *Lysobacter capsici* AZ78, ii) a strain obtainable from deposit CBS 134400, and iii) a strain comprising a nucleic acid sequence that has at least 99% identity to a sequence selected from the group consisting of SEQ ID NOs: 6-13, especially comprising, for each member of the group consisting of SEQ ID NOs: 6-13, at least one nucleic acid sequence that has at least 99% identity to said member.

As used herein, a strain "obtainable from" a certain deposit will be readily understood by the skilled person. It is particularly intended to include a culture of a bacterial strain that is based on a sample of said deposit. As used herein, a "strain obtainable from" said deposit preferably also includes a "bacterium obtainable from" said deposit and may also be referred to herein as an "*Lysobacter capsici* obtainable from" said deposit, wherein all of the above are included within the bacteria of the present invention. For the purposes herein, a strain "obtainable from" a certain deposit may also mean a strain "available from" said certain deposit.

Generally, the terms "*Lysobacter*" and "*Lysobacter capsici*" herein are used as known in the art. Generally herein, strains of the present invention (and, likewise, bacteria of the present invention) include those of *Lysobacter capsici* AZ78, a strain obtainable from deposit CBS 134400 and variants thereof.

Accordingly, an embodiment of the first aspect relates to *Lysobacter capsici* AZ78. Likewise, an embodiment of the first aspect relates to a strain obtainable from deposit CBS 134400. In accordance with the present invention, *Lysobacter capsici* strain AZ78 has been deposited under the Budapest Treaty at the CBS (Centraalbureau voor Schimmelcultures) on Feb. 21, 2013, and has been assigned accession number CBS 134400 (cf. also the respective receipts of deposit filed herewith).

In addition, an embodiment of the first aspect relates to a strain comprising a nucleic acid sequence that has at least 99% identity to a sequence selected from the group consisting of SEQ ID NOs: 6-13. In a preferred embodiment, said strain comprises, for each member of the group consisting of SEQ ID NOs: 6-13, at least one nucleic acid sequence that has at least 99% identity to said member. As used herein "for each member of the group consisting of SEQ ID NOs: 6-13" means that there is at least one corresponding nucleic acid sequence for each of SEQ ID NOs 6 to 13, wherein said at least one corresponding nucleic acid sequence has the said identity. In other words, said strain may e.g. comprise a nucleic acid sequence that has at least 99% identity to SEQ ID NO: 6, as well as a nucleic acid sequence that has at least 99% identity to SEQ ID NO: 7, as well as a nucleic acid sequence that has at least 99% identity to SEQ ID NO: 8, as well as a nucleic acid sequence that has at least 99% identity to SEQ ID NO: 9, as well as a nucleic acid sequence that has at least 99% identity to SEQ ID NO: 10, as well as a nucleic acid sequence that has at least 99% identity to SEQ ID NO: 11, as well as a nucleic acid sequence that has at least 99% identity to SEQ ID NO: 12, as well as and a nucleic acid sequence that has at least 99% identity SEQ ID NO: 13.

Hence, also variants of *Lysobacter capsici* strain AZ78, as well as variants of a *Lysobacter capsici* obtainable from deposit CBS 134400, are explicitly included within the *Lysobacter capsici* strain of the present invention. Such variants include, but are not limited to mutants of *Lysobacter capsici* strain AZ78, particularly mutants having one or more, or all of the identifying characteristics of *Lysobacter capsici* AZ78, such as one or more of the advantageous features described herein.

Such variants preferably include *Lysobacter capsici* bacteria having a nucleic acid sequence that has at least 99% (preferably at least 99.1, 99.2, 99.3, 99.4, 99.5, 99.6, 99.7, 99.8 or 99.9%) identity to a corresponding nucleic acid sequence of *Lysobacter capsici* AZ78, wherein said nucleic acid sequence is one of the sequences disclosed herein, such as one of SEQ ID NOs: 6 to 13. In certain embodiments, variants include *Lysobacter capsici* bacteria that comprise at least one nucleic acid sequence that has at least 99% identity to a corresponding SEQ ID NO for each of SEQ ID NOs: 6 to 13.

Generally, in certain embodiments herein, at least 99% may be substituted by at least 99.1, 99.2, 99.3, 99.4, 99.5, 99.6, 99.7, 99.8% or at least 99.9%.

Similarly, in a second aspect, the present invention relates to a bacterium of a bacterial strain according to the first aspect or derivable from a bacterial strain as defined in the first aspect.

As used herein, a bacterium "derivable from" a certain bacterial strain will be readily understood by the skilled person. It is particularly intended to include a culture of a bacterium that is based on a sample of such strain, e.g. a sample of said deposit. The term "derivable from" preferably also includes any bacteria obtained after culturing strains or bacteria of the present invention. Accordingly, the "derivable from" preferably also includes any progeny of strains and bacteria of the present invention.

In accordance with what has been disclosed above, the bacteria of the second aspect also include variants of *Lysobacter capsici* AZ78, as well as variants of a *Lysobacter capsici* obtainable from deposit CBS 134400. Such variants include but are not limited to mutants of *Lysobacter capsici* AZ78, particularly mutants having one or more, or all of the identifying characteristics of *Lysobacter capsici* AZ78, such as one or more of the advantageous features described herein. Such variants preferably include *Lysobacter capsici* bacteria having a nucleic acid sequence that has at least 99% (preferably at least 99.1, 99.2, 99.3, 99.4, 99.5, 99.6, 99.7, 99.8% or at least 99.9%) identity to a corresponding nucleic acid sequence of *Lysobacter capsici* AZ78 bacteria, wherein said nucleic acid sequence is one of the sequences disclosed herein, such as one of SEQ ID NOs: 6 to 13. In certain embodiments, variants include *Lysobacter capsici* bacteria that comprise at least one nucleic acid sequence that has at least 99% identity to a corresponding SEQ ID NO for each of SEQ ID NOs: 6 to 13.

Generally herein, the strain of the first aspect and bacteria of the second aspect may be collectively referred herein as "bacteria of the present invention". Accordingly, as used herein, the term "bacteria of the invention" may comprise the strains of the first aspect and the bacteria of the second aspect.

Preferably, the bacteria of the present invention have one, more than one, any combination of, or all of the following features: i) they are not associated with any human disease, ii) they are effective against *Plasmopara viticola*, iii) they are effective against *Phytophthora infestans*, iv) they are more effective as a biocontrol agent than other *Lysobacter* bacteria, v) they persist on plants, vi) they persist on phyllosphere of crop plants, vii) they are able to form bio films, viii) are not negatively affected by stress caused by lack of nutrients (starvation) and do not suffer following exposure to increasing temperatures (mild heat shock), ix) are able to tolerate exposure to UV irradiation, x) are able to tolerate freezing temperatures (e.g. up to −20° C.).

Accordingly, preferably, the bacteria of the present invention are not associated with any human disease. Preferably, the bacteria of the present invention are effective against *Plasmopara viticola*. Preferably, the bacteria of the present invention are effective against *Phytophthora infestans*. Preferably, the bacteria of the present invention are more effective as a biocontrol agent than other *Lysobacter* bacteria. Preferably, the bacteria of the present invention persist on plants, preferably on phyllosphere of crop plants. Preferably, the bacteria of the present invention are able to form biofilms. Preferably, the bacteria of the present invention do not suffer following exposure to increasing temperatures (mild heat shock). Preferably, the bacteria of the present invention are able to tolerate exposure to UV irradiation, particularly UV irradiation as employed in the examples herein. Preferably, the bacteria of the present invention are able to tolerate freezing temperatures (e.g. up to −20° C.; e.g. as employed in the examples herein).

In view of the above, the strains of the first aspect may have any (or any combination) of the above described features. Likewise, the bacteria of the second aspect may have any (or any combination) of these features.

In a third aspect, the present invention relates to a bacterial preparation, selected from the group consisting of i) a preparation of *Lysobacter capsici* AZ78, ii) a preparation of a bacterium obtainable from deposit CBS 134400, iii) a preparation of a bacterium comprising a nucleic acid sequence that has at least 99% identity to a sequence selected from the group consisting of SEQ ID NOs: 6-13, especially comprising, for each member of the group consisting of SEQ ID NOs: 6-13, at least one nucleic acid sequence that has at least 99% identity to said member, and iv) a preparation of a bacterium according to the second aspect.

Accordingly, an embodiment of the third aspect relates to a preparation of *Lysobacter capsici* AZ78. In addition, an embodiment of the third aspect relates to a preparation of a bacterium obtainable from deposit CBS 134400. As used herein, a bacterium "obtainable from" a certain deposit will be readily understood by the skilled person. It is particularly intended to include a bacterium that is contained in a sample of said deposit and also includes any bacteria obtained after culturing such bacterium. A "bacterium obtainable from" said deposit is also included within the bacteria of the present invention. For the purposes herein, a bacterium "obtainable from" a certain deposit may also mean a bacterium "available from" said certain deposit. Also, an embodiment of the third aspect relates to a preparation of a bacterium comprising a nucleic acid sequence that has at least 99% identity to a sequence selected from the group consisting of SEQ ID NOs: 6-13, particularly comprising, for each member of the group consisting of SEQ ID NOs: 6-13, at least one nucleic acid sequence that has at least 99% identity to said member. Hence, the above described variants of *Lysobacter capsici* AZ78 are also envisaged in context with the third aspect. Accordingly, a bacterial preparation of the present invention may also be a preparation comprising variants of bacteria of the present invention, such as variants of *Lysobacter capsici* strain AZ78, wherein said variants are as described hereinabove. Besides, a further embodiment of the third aspect relates to a preparation of a bacterium according to the second aspect.

As used herein, a bacterial preparation preferably refers to a preparation comprising bacteria of the present invention.

Generally herein, the form of the bacteria of the present invention (such as the bacteria contained in a bacterial preparation of the present invention) is not particularly limited. In certain embodiments, the bacterial preparation is a liquid preparation. Accordingly, in certain embodiments, the bacterial preparations herein are suspensions of the bacteria of the invention or the respective *Lysobacter capsici.*

The bacterial preparations herein may preferably comprise additives. Non-limiting examples of such additives include one or more additives selected from the group consisting of wetting agents, adhesives, feeding stimulants and carriers, all of which are well-known to the skilled person. An exemplary wetting agent is Tween 80 and an exemplary carrier is cellulose.

In certain embodiments herein, the bacterial preparations herein additionally comprise or are administered in conjunction with one or more additional plant protection products, preferably copper-containing plant protection products, especially selected from the group consisting of Kocide 3000, Blue Shield DF, Cupravit, Cupravit Bio Evolution, Airone, Airone Pill, Corvit, Iram, Coprantol HI BIO, Idrorame Flow, Poltiglia bordolese, Cobre Nordox Super 75 WG, and any other plant protection products suitable for treating a plant disease that is caused by a fungus or an oomycete selected from the group consisting of *Alternaria alternata, Ascochyta rabiei, Aspergillus flavus, Aspergillus niger, Aspergillus ochraceus, Botrytis cinerea, Colletotrichum gloeosporioides, Fusarium acuminatum, Fusarium avenaceum, Fusarium oxysporum* f. sp. *asparagi, Fusarium oxysporum* f. sp. *lycopersici, Fusarium oxysporum* f. sp. *radicis-lycopersici, Fusarium sambucinum, Fusarium semitectum, Fusarium solani, Penicillium* sp., *Phoma tracheiphila, Phytophthora cactorum, Phytophthora capsici, Phytophthora cinnamomi, Phytophthora infestans, Plasmopara viticola, Pythium ultimum, Rhizoctonia solani, Sclerotinia major, Sclerotinia minor, Sclerotinia sclerotiorum*, and *Thielaviopsis basicola*. The above cited products are commercially available from the following manufactures: Kocide 3000 (Du Pont), Blue Shield DF (Bayer), Cupravit (Bayer Cropscience), Cupravit Bio Evolution (Bayer Cropscience), Airone (Isagro), Airone Pin (Isagro), Corvit (New Agri), Iram (Agrimix), Coprantol HI BIO (Syngenta), Idrorame Flow (Chimiberg), Poltiglia bordolese (Agrisystem), Cobre Nordox Super 75 WG, (Comercial Quichimica Masse)). In particularly preferred embodiments, the copper-containing plant protection product is suitable for treating grapevine downy mildew caused by *Plasmopara viticola* and/or late blight, particularly tomato late blight, caused by *Phytophthora infestans*. Particularly preferred plant protection products for use in conjunction with the (bacterial) plant protection products of the invention are compositions comprising copper as disclosed herein. Hence, the embodiments described in the latter context are also envisaged in connection with the present aspect, and vice versa.

In certain embodiments herein, the bacterial preparations herein additionally comprise or are administered in conjunction with one or more acaricides. In certain embodiments herein, the bacterial preparations herein additionally comprise or are administered in conjunction with one or more insecticides. In certain embodiments herein, the bacterial preparations herein additionally comprise or are administered in conjunction with one or more plant strengtheners, leaf fertilizers and plant resistance inducers.

In line with the above, the bacterial preparations of the third aspect may have any (or any combination) of the preferred features of the bacteria of the invention disclosed above.

In certain embodiments, said bacterial preparation may by itself qualify and/or be referred to as a plant protection product. In certain embodiments, the bacterial preparation is a plant protection product against downy mildews in plants, particularly in grapevine plants, and may also be referred to herein as a bacterial preparation for treating downy mildews in plants. In certain embodiments, the bacterial preparation is a plant protection product against diseases caused by *Phytophthora infestans* in plants, particularly in potatoes and/or tomatoes, and may also be referred to herein as a bacterial preparation for treating tomato late blight or potato late blight in plants.

In a fourth aspect, the present invention relates to the use of a bacterial strain according to the first aspect, a bacterium according to the second aspect, or a bacterial preparation according to the third aspect, for preparing a plant protection product. Accordingly, an embodiment of the fourth aspect relates to the use of a bacterial strain according to the first aspect for preparing a plant protection product. An embodiment of the fourth aspect relates to the use of a bacterium according to the second aspect for preparing a plant protection product. An embodiment of the fourth aspect relates to the use of a bacterial preparation according to the third aspect for preparing a plant protection product.

As used herein, the term "plant protection product", which may also be referred to herein as a "biocontrol agent", is not particularly limited and generally used as it is known in the art. In preferred embodiments, the plant protection product is a bacterial plant protection product, such as a plant protection product comprising bacteria of the present invention. Accordingly, in preferred embodiments, the plant protection product is a bacterial biocontrol agent.

Preferably herein, the plant protection product is a plant protection product against any of the plant diseases disclosed herein. Hence, the plant protection product preferably is a plant protection product against a plant pathogenic fungus and/or a plant pathogenic oomycete. Preferably, the plant protection product is a plant protection product against the oomycetes disclosed herein. Preferred examples of said diseases described elsewhere herein apply also as to the fourth aspect. In preferred embodiments, the plant protection product is a plant protection product against downy mildews in plants, particularly in grapevine plants, and may also be referred to herein as a bacterial preparation for treating downy mildews in plants. In certain embodiments, the plant protection product is a plant protection product against diseases caused by *Phytophthora infestans* in plants, particularly in potatoes and/or tomatoes, and may also be referred to herein as a plant protection product for treating tomato late blight or potato late blight in plants.

Moreover, in a fifth aspect, the present invention relates to a plant protection product comprising a bacterial strain according to the first aspect, at least one bacterium according to the second aspect, or a bacterial preparation according to the third aspect. Generally, the plant protection product of the fifth aspect may be a plant protection product prepared in accordance with the fourth aspect.

One embodiment of the fifth aspect relates to a plant protection product comprising a bacterial strain according to the first aspect. An embodiment of the fifth aspect relates to a plant protection product comprising at least one bacterium according to the second aspect. An embodiment of the fifth aspect relates to a plant protection product comprising a bacterial preparation according to the third aspect.

As used herein, a plant protection product prepared in accordance with the fourth aspect and/or a plant protection product of the fifth aspect may be referred to herein as a "plant protection product of the invention".

Preferably, the plant protection product of the invention is a plant protection product against a plant pathogenic fungus and/or a plant pathogenic oomycete. Accordingly, the plant protection product of the invention may be a plant protection product against a plant pathogenic fungus. Accordingly, the plant protection product of the invention may be a plant protection product against a plant pathogenic oomycete. Preferably, the plant protection product is a plant protection product against oomycetes disclosed herein.

Preferred examples of a plant pathogenic fungus and/or plant pathogenic oomycete in connection with the fourth and fifth aspects herein—and generally preferred examples of a plant pathogenic fungus and/or plant pathogenic oomycete in connection with the present invention—are selected from the group consisting of *Alternaria alternata, Ascochyta rabiei, Aspergillus flavus, Aspergillus niger, Aspergillus ochraceus, Botrytis cinerea, Colletotrichum gloeosporioides, Fusarium acuminatum, Fusarium avenaceum, Fusarium oxysporum* f. sp. *asparagi, Fusarium oxysporum* f. sp. *lycopersici, Fusarium oxysporum* f. sp. *radicis-lycopersici, Fusarium sambucinum, Fusarium semitectum, Fusarium solani, Penicillium* sp., *Phoma tracheiphila, Phytophthora cactorum, Phytophthora capsici, Phytophthora cinnamomi, Phytophthora infestans, Plasmopara viticola, Pythium ultimum, Rhizoctonia solani, Sclerotinia major, Sclerotinia minor, Sclerotinia sclerotiorum*, and *Thielaviopsis basicola.*

Accordingly, it generally will be appreciated by the skilled person that the bacteria and bacterial preparations of the present invention may be used as a plant protection product, particularly as a plant protection product against plant diseases (or in other words a plant protection product against plant diseases or in other words a plant protection product to treat plant diseases).

In line with the above, the plant protection products of the present invention, such as that prepared in accordance with the fourth aspect and those of the fifth aspect, may be characterized by any (or any combination) of the preferred features of the bacteria and bacterial preparations of the invention disclosed above. For example in preferred embodiments of the fourth and fifth aspects, the plant protection product comprises any of the additional agents described in connection of the third aspect, such as additives, acaricides, insecticides, plant strengtheners, leaf fertilizers and/or plant resistance inducers. In particular, in certain embodiments herein, the bacterial preparations herein additionally comprise or are administered in conjunction with one or more additional plant protection products, preferably copper-containing plant protection products, particularly as defined elsewhere herein, especially as described above in context with the third aspect.

In particularly preferred embodiments of the fourth and fifth aspect herein—and generally in context with the invention—said plant pathogenic oomycete is selected from *Plasmopara viticola* and *Phytophthora infestans*. Accordingly, in particularly preferred embodiments of the fourth and fifth aspect herein—and generally in context with the invention—said plant pathogenic oomycete is *Plasmopara viticola*. Accordingly, in particularly preferred embodiments of the fourth and fifth aspect herein—and generally in context with the invention—said plant pathogenic oomycete is *Phytophthora infestans*.

Thus, the fourth aspect preferably relates to the use of a bacterial strain according to the first aspect, a bacterium according to the second aspect, or a bacterial preparation according to the third aspect, for preparing a plant protection product against *Plasmopara viticola* and/or *Phytophthora infestans*. Likewise, the fifth aspect preferably relates to the use of a bacterial strain according to the first aspect, a bacterium according to the second aspect, or a bacterial preparation according to the third aspect, for preparing a plant protection product against *Plasmopara viticola* and/or *Phytophthora infestans*.

In certain embodiments, said plant protection product is a plant protection product against downy mildews in plants, particularly in grapevine plants, and may also be referred to herein as a plant protection product for treating downy mildews in plants. In certain embodiments, said plant protection product is a plant protection product against diseases caused by *Phytophthora infestans* in plants, particularly in potatoes and/or tomatoes, and may also be referred to herein as a plant protection product for treating tomato late blight or potato late blight in plants.

In a sixth aspect, the present invention relates to the use of a bacterial strain according to the first aspect, a bacterium according to the second aspect, a bacterial preparation according to the third aspect, a plant protection product according to the fifth aspect or a plant protection product as defined in the fourth aspect, for preventing or treating a plant disease, particularly a fungal disease and/or an oomycete disease. Accordingly, an embodiment of the sixth aspect relates to the use of a bacterial strain according to the first aspect for preventing or treating a plant disease, particularly a fungal disease and/or an oomycete disease. Accordingly, an embodiment of the sixth aspect relates to a bacterium according to the second aspect for preventing or treating a plant disease, particularly a fungal disease and/or an oomycete disease. Accordingly, an embodiment of the sixth aspect relates to a bacterial preparation according to the third aspect for preventing or treating a plant disease, particularly a fungal disease and/or an oomycete disease. Accordingly, an embodiment of the sixth aspect relates to a plant protection product according to the fifth aspect for preventing or treating a plant disease, particularly a fungal disease and/or an oomycete disease. Accordingly, an embodiment of the sixth aspect relates to or a plant protection product as defined in the fourth aspect for preventing or treating a plant disease, particularly a fungal disease and/or an oomycete disease.

Preferably, in the sixth aspect—and generally in context with the invention—said plant disease is caused by a fungus and/or an oomycete selected from the group consisting of *Alternaria alternata, Ascochyta rabiei, Aspergillus flavus, Aspergillus niger, Aspergillus ochraceus, Botrytis cinerea, Colletotrichum gloeosporioides, Fusarium acuminatum, Fusarium avenaceum, Fusarium oxysporum* f. sp. *asparagi, Fusarium oxysporum* f. sp. *lycopersici, Fusarium oxysporum* f. sp. *radicis-lycopersici, Fusarium sambucinum, Fusarium semitectum, Fusarium solani, Penicillium* sp., *Phoma tracheiphila, Phytophthora cactorum, Phytophthora capsici, Phytophthora cinnamomi, Phytophthora infestans, Plasmopara viticola, Pythium ultimum, Rhizoctonia solani, Sclerotinia maior, Sclerotinia minor, Sclerotinia sclerotiorum*, and *Thielaviopsis basicola.*

Preferably, in the sixth aspect—and generally in context with the invention—said plant disease is caused by an oomycete selected from *Plasmopara viticola* and *Phytophthora infestans.*

More preferably, in the sixth aspect—and generally in context with the invention—said plant disease is caused by *Plasmopara viticola*. More in particular, said disease is downy mildew, particularly grapevine downy mildew. Accordingly, in the sixth aspect—and generally in context with the invention—said plant disease may be downy mildew, preferably grapevine downy mildew. Also preferably, in the sixth aspect—and generally in context with the invention—said plant disease is caused by *Phytophthora infestans*. More in particular, said disease is tomato late blight or potato late blight caused by *Phytophthora infestans*, particularly tomato late blight. Accordingly, in the sixth aspect—and generally in context with the invention—said plant disease is tomato late blight or potato late blight, preferably tomato late blight.

As used herein, the term "treating a plant disease" and suchlike terms are equivalently used with the term "for treating plants against a plant disease". This term preferably also includes the term "for treating plants affected by a plant disease". In any case, it will be appreciated by the skilled person that the bacteria, bacterial strains, bacterial preparations and plant protection products of the invention may be used against plant diseases (which may e.g. be prevented or treated/controlled in context with the present invention). Preferably, said plant diseases are in accordance with the preferred embodiments of any of the particular aspects herein.

Similarly, in a seventh aspect, the present invention relates to method of preventing or treating a plant disease, particularly a fungal disease and/or an oomycete disease, comprising a step of contacting at least one plant with a bacterial strain, bacterium, bacterial composition or plant protection product as defined in any of the above aspects. Preferably, said plant disease is caused by a fungus or an oomycete selected from the group consisting of *Alternaria alternata, Ascochyta rabiei, Aspergillus flavus, Aspergillus niger, Aspergillus ochraceus, Botrytis cinerea, Colletotrichum gloeosporioides, Fusarium acuminatum, Fusarium avenaceum, Fusarium oxysporum* f. sp. *asparagi, Fusarium oxysporum* f. sp. *lycopersici, Fusarium oxysporum* f. sp. *radicis-lycopersici, Fusarium sambucinum, Fusarium semitectum, Fusarium solani, Penicillium* sp., *Phoma tracheiphila, Phytophthora cactorum, Phytophthora capsici, Phytophthora cinnamomi, Phytophthora infestans, Plasmopara viticola, Pythium ultimum, Rhizoctonia solani, Sclerotinia maior, Sclerotinia minor, Sclerotinia sclerotiorum*, and *Thielaviopsis basicola.*

More preferably, said plant disease is caused by an oomycete selected from *Plasmopara viticola* and *Phytophthora infestans*. Particularly, said plant disease is caused by *Plasmopara viticola*. Preferably, said disease is downy mildew, particularly grapevine downy mildew. Particularly, said plant disease is caused by *Phytophthora infestans*. Preferably, said disease is tomato late blight or potato late blight, particularly tomato late blight.

Generally, preferred embodiments of the sixth and seventh aspect include those described in context with the first, second, third, fourth and/or fifth aspects.

In certain preferred embodiments of the uses, plant protection products or methods according to any of the fourth, fifth, sixth and seventh aspects, the plant protection product additionally comprises copper and/or said use or method additionally comprises a step of contacting said plant with a composition comprising copper. Hence, in certain preferred embodiments of the uses, plant protection products or methods according to any of the fourth, fifth, sixth and seventh aspects, the plant protection product additionally comprises copper. Hence, in certain preferred embodiments of the uses, plant protection products or methods according to any of the fourth, fifth, sixth and seventh aspects, said use or method additionally comprises a step of contacting said plant with a composition comprising copper.

Generally, in preferred embodiments, the fourth, fifth, sixth and seventh aspects may be characterized by any (or any combination) of the preferred features of the bacteria and bacterial preparations of the invention disclosed above. For example, the bacterial composition or plant protection product may comprise or be administered in conjunction with any of the additional agents described in connection of the third aspect, such as additives, acaricides, insecticides, plant strengtheners, leaf fertilizers and/or plant resistance inducers. In particular, in certain embodiments herein, the bacterial compositions or plant protection products additionally comprise or are administered in conjunction with one or more additional plant protection products, preferably copper-containing plant protection products, particularly as defined elsewhere herein, especially as described above in context with the third aspect.

Further, in an eighth aspect, the present invention relates to a kit of parts comprising i) a composition comprising copper and ii) a member of the group consisting of a bacterial strain belonging to *Lysobacter capsici*, a bacterium belonging to *Lysobacter capsici*, a bacterial preparation of *Lysobacter capsici*, a bacterial strain according to the first aspect, a bacterium according to the second aspect, a bacterial preparation according to the third aspect, a plant protection product according to the fifth aspect and a plant protection product as defined in the fourth aspect; particularly wherein said composition comprising copper is a copper plant protection product, especially wherein said composition comprising copper comprises at least one copper compound selected from the group consisting of copper hydroxide, copper oxycloride, copper sulphate, tribasic copper sulphate, and copper octanoate.

In certain preferred embodiments of the eighth aspect, said composition comprising copper is a copper plant protection product, especially wherein said composition comprising copper comprises at least one copper compound selected from the group consisting of copper hydroxide, copper oxycloride, copper sulphate, tribasic copper sulphate, and copper octanoate.

In certain embodiments, the composition comprising copper comprises at least one copper compound selected from the group consisting of copper(II) acetate, copper(II) carbonate, basic copper hydroxide, copper naphthenate, copper oleate, copper oxychloride, copper(II) sulfate, basic copper sulfate, and copper zinc chromate.

In particularly preferred embodiments, the composition comprising copper comprises copper hydroxide. Copper plant protection products are well known in the art and are generally commercially available. Particular examples include Bordeaux mixture and Kocide 3000 (containing 15% copper hydroxide, WG, Du Pont de Nemours, USA), which is used in the present examples. Generally herein, preferred embodiments of the composition comprising copper are as defined elsewhere herein, and especially are copper-containing plant protection products as defined in context with the third aspect.

Preferred (final) concentrations of copper may readily be determined by the skilled person and may e.g. be taken from the present examples. Generally, preferred concentration ranges of copper to be used herein are from 10 to 500 mg $L^{-1}$, preferably 50 to 450 mg $L^{-1}$, preferably 50 to 400 mg $L^{-1}$, preferably 90 to 400 mg $L^{-1}$, preferably 90 to 375 mg $L^{-1}$. Particularly preferred concentration ranges are from 10 to 300 mg $L^{-1}$, preferably 20 to 250 mg $L^{-1}$, preferably 50 to 190 mg $L^{-1}$, preferably 90 to 190 mg $L^{-1}$. An exemplary preferred concentration range is from 100-500 mg $L^{-1}$.

Generally, other preferred embodiments of the composition comprising copper correspond to those described elsewhere herein. Generally, certain preferred embodiments of the eighth aspect correspond to any of the preferred embodiments described herein above.

In preferred embodiments, the kits herein or any of its components comprise any of the additional agents described in connection of the third aspect, such as additives, acaricides, insecticides, plant strengtheners, leaf fertilizers and/or plant resistance inducers.

Moreover, in a ninth aspect, the invention relates to the use of a composition comprising copper in a method of preventing or treating a plant disease, particularly a fungal disease and/or an oomycete disease, characterized in that said composition comprising copper is used in combination with a member of the group consisting of a bacterial strain belonging to *Lysobacter capsici*, a bacterium belonging to *Lysobacter capsici*, a bacterial preparation of *Lysobacter capsici*, a bacterial strain according to the first aspect, a bacterium according to the second aspect, a bacterial preparation according to the third aspect, a plant protection product according to the fifth aspect and a plant protection product as defined in the fourth aspect, particularly further characterized in accordance with any of the preceding aspects; especially wherein said plant disease is caused by a fungus or an oomycete selected from the group consisting of *Alternaria alternata, Ascochyta rabiei, Aspergillus flavus, Aspergillus niger, Aspergillus ochraceus, Botrytis cinerea, Colletotrichum gloeosporioides, Fusarium acuminatum, Fusarium avenaceum, Fusarium oxysporum* f. sp. *asparagi, Fusarium oxysporum* f. sp. *lycopersici, Fusarium oxysporum* f. sp. *radicis-lycopersici, Fusarium sambucinum, Fusarium semitectum, Fusarium solani, Penicillium* sp., *Phoma tracheiphila, Phytophthora cactorum, Phytophthora capsici, Phytophthora cinnamomi, Phytophthora infestans, Plasmopara viticola, Pythium ultimum, Rhizoctonia solani, Sclerotinia major, Sclerotinia minor, Sclerotinia sclerotiorum*, and *Thielaviopsis basicola*, particularly wherein said plant disease is caused by an oomycete selected from *Plasmopara viticola* and *Phytophthora infestans*. Particularly, said plant disease is caused by *Plasmopara viticola*. Preferably said disease is downy mildew, especially grapevine downy mildew. Particularly, said plant disease is caused by *Phytophthora infestans*. Preferably, said disease is tomato late blight or potato late blight, particularly tomato late blight.

Generally, certain preferred embodiments of the ninth aspect correspond to any of the preferred embodiments described herein above. Generally, preferred embodiments of the composition comprising copper correspond to those described elsewhere herein. Particularly, in preferred embodiments of the ninth aspect, said composition comprising copper is characterized as in the embodiments described for the third and/or eighth aspect.

In addition, for example, in certain embodiments of the ninth aspect, said plant disease is caused by a fungus or an oomycete selected from the group consisting of *Alternaria alternata, Ascochyta rabiei, Aspergillus flavus, Aspergillus niger, Aspergillus ochraceus, Botrytis cinerea, Colletotrichum gloeosporioides, Fusarium acuminatum, Fusarium avenaceum, Fusarium oxysporum* f. sp. *asparagi, Fusarium oxysporum* f. sp. *lycopersici, Fusarium oxysporum* f. sp. *radicis-lycopersici, Fusarium sambucinum, Fusarium semitectum, Fusarium solani, Penicillium* sp., *Phoma tracheiphila, Phytophthora cactorum, Phytophthora capsici, Phytophthora cinnamomi, Phytophthora infestans, Plasmopara viticola, Pythium ultimum, Rhizoctonia solani, Sclerotinia maior, Sclerotinia minor, Sclerotinia sclerotiorum*, and *Thielaviopsis basicola*, particularly wherein said plant disease is caused by an oomycete selected from *Plasmopara viticola* and *Phytophthora infestans*. Particularly, said plant disease is caused by *Plasmopara viticola*. Preferably, said disease is downy mildew, especially grapevine downy mildew. Particularly, said disease is caused by *Phytophthora infestans*. Preferably, said disease is tomato late blight or potato late blight, particularly tomato late blight.

Moreover, in a tenth aspect, the invention relates to a method of preventing or treating a plant disease, particularly a fungal disease and/or an oomycete disease, comprising a step of contacting at least one plant with a composition comprising copper, characterized in that method further comprises a step of contacting said at least one plant with a member of the group consisting of a bacterial strain belonging to *Lysobacter capsici*, a bacterium belonging to *Lysobacter capsici*, a bacterial preparation of *Lysobacter capsici*, a bacterial strain according to the first aspect, a bacterium according to the second aspect, a bacterial preparation according to the third aspect, a plant protection product according to the fifth aspect and a plant protection product as defined in the fourth aspect, particularly further characterized in accordance with any of the preceding aspects; especially wherein said plant disease is caused by a fungus or an oomycete selected from the group consisting of *Alternaria alternata, Ascochyta rabiei, Aspergillus flavus, Aspergillus niger, Aspergillus ochraceus, Botrytis cinerea, Colletotrichum gloeosporioides, Fusarium acuminatum, Fusarium avenaceum, Fusarium oxysporum* f. sp. *asparagi, Fusarium oxysporum* f. sp. *lycopersici, Fusarium oxysporum* f. sp. *radicis-lycopersici, Fusarium sambucinum, Fusarium semitectum, Fusarium solani, Penicillium* sp., *Phoma tracheiphila, Phytophthora cactorum, Phytophthora capsici, Phytophthora cinnamomi, Phytophthora infestans, Plasmopara viticola, Pythium ultimum, Rhizoctonia solani, Sclerotinia major, Sclerotinia minor, Sclerotinia sclerotiorum*, and *Thielaviopsis basicola*, particularly wherein said plant disease is caused by an oomycete selected from *Plasmopara viticola* and *Phytophthora infestans*. In particular, said plant disease is caused by *Plasmopara viticola*. Preferably, said disease is downy mildew, especially grapevine downy mildew. In particular, said disease is caused by *Phytophthora infestans*. Preferably, said disease is tomato late blight or potato late blight, particularly tomato late blight.

As used herein, the term "treating" or grammatical equivalents, particularly in the context with a plant disease, may be equivalently used with the term "controlling" or grammatical equivalents.

Generally, certain preferred embodiments of the tenth aspect correspond to any of the preferred embodiments described herein above.

Generally, in preferred embodiments, the eighth, ninth and tenth aspects may be characterized by any (or any combination) of the preferred features of the bacteria, bacterial preparations and plant protection products of the invention disclosed above. For example, the bacterial preparations and/or plant protection products may comprise or be administered in conjunction with any of the additional agents described in connection of the third aspect, such as additives, acaricides, insecticides, plant strengtheners, leaf fertilizers and/or plant resistance inducers.

Preferably, said compositions comprising copper are copper-containing plant protection products as defined in context with the preceding aspects, such as the third aspect. In certain preferred embodiments of the tenth aspect, said composition comprising copper is a copper plant protection product, especially wherein said composition comprising copper comprises at least one copper compound selected from the group consisting of copper hydroxide, copper oxycloride, copper sulphate, tribasic copper sulphate, and copper octanoate. In certain embodiments, the composition comprising copper comprises at least one copper compound selected from the group consisting of copper(II) acetate, copper(II) carbonate, basic copper hydroxide, copper naphthenate, copper oleate, copper oxychloride, copper(II) sulfate, basic copper sulfate, and copper zinc chromate. Generally, other preferred embodiments of the composition comprising copper correspond to those described elsewhere herein.

The following embodiments and teachings are generally applicable herein:

Generally herein, embodiments described in connection with any particular aspect of the invention are also contemplated as embodiments of the other aspects of the invention. Generally herein, suchlike embodiments include analogous embodiments in the given context.

Generally, the handling of *Lysobacter capsici* (including, but not limited to culturing, storage, fermentation, formulation and application) is well-known to the skilled person. This particularly applies in view of the teachings of the Examples disclosed herein below. Accordingly, it is e.g. envisaged that suitable concentrations of *Lysobacter capsici* for application to plants can easily be determined by the skilled person.

As non-limiting example, the *Lysobacter capsici* bacteria or bacterial preparations herein may be applied by ground spraying. Exemplary preferred application frequencies herein are from 2 to 15 applications per season, such as from 2 to 12 or from 5 to 9 applications per season, particularly 2, 3, 4, 5, 6, 7, 8, 9, 10, 11, 12, 13, 14 or 15 applications per season. Preferred numbers of application can easily be determined by the skilled person and e.g. depend on disease pressure.

As non-limiting example, the *Lysobacter capsici* bacteria or bacterial preparations herein may be applied in doses of about $10^7$ to $10^9$ bacterial cells per ml of bacterial preparation, preferably of about $0.2 \times 10^8$ to $5 \times 10^8$ bacterial cells per ml of bacterial preparation, preferably of about $0.5 \times 10^8$ to $2 \times 10^8$ bacterial cells per ml of bacterial preparation, such as of about $10^8$ bacterial cells per ml of bacterial preparation as employed in present examples.

Generally, preferred concentration ranges of copper to be employed in the uses and methods of the invention are from 10 to 500 mg $L^{-1}$, preferably 50 to 450 mg $L^{-1}$, preferably 50 to 400 mg $L^{-1}$, preferably 90 to 400 mg $L^{-1}$, preferably 90 to 375 mg $L^{-1}$. Particularly preferred concentration ranges are from 10 to 300 mg $L^{-1}$, preferably 20 to 250 mg $L^{-1}$, preferably 50 to 190 mg $L^{-1}$, preferably 90 to 190 mg $L^{-1}$. An exemplary preferred concentration range is from 100-500 mg $L^{-1}$.

As non-limiting examples, the *Lysobacter capsici* bacteria, bacterial preparations and plant protection products herein may be applied to the shoot, stem, leaves, seeds, and/or vegetative propagules of one or more plants, preferably to the shoot, stem, leaves and/or vegetative propagules of one or more plants, more preferably to the stem and/or leaves, preferably to the leaves of at least one plant.

Generally, the bacterial preparations and plant protection products herein may additionally comprise additives. Non-limiting examples of such additives include one or more additives selected from the group consisting of wetting agents, adhesives, feeding stimulants and carriers, all of which are well-known to the skilled person. An exemplary wetting agent is Tween 80 and an exemplary carrier is cellulose.

Generally, the bacterial preparations and plant protection products herein may additionally comprise or be administered in conjunction with one or more acaricides. In certain embodiments herein, the bacterial preparations and plant protection products herein may additionally comprise or are administered in conjunction with one or more insecticides. In certain embodiments herein, the bacterial preparations and plant protection products herein may additionally comprise or are administered in conjunction with one or more plant strengtheners, leaf fertilizers and/or plant resistance inducers.

Generally, in preferred embodiments of the uses and methods herein the bacteria, bacterial preparations and plant protection products herein are used in an amount effective against a plant disease. An effective amount herein means an amount effective to achieve a significant inhibition of the disease in at least one plant, particularly when compared to a control in the absence of said bacteria, bacterial preparations and plant protection products.

In preferred embodiments herein, the bacteria or bacterial preparations of the invention have plant protection product efficacy and/or biocontrol efficacy, preferably plant protection product efficacy and/or biocontrol efficacy as defined hereinabove.

In preferred embodiments herein, the bacteria, bacterial preparation and plant protection products of the invention are applied to plants that show symptoms of plant disease, such as at least one plant that shows visible signs of downy mildew, particularly grapevine downy mildew and/or potato late blight or tomato late blight, particularly tomato late blight. Such symptoms and signs are well-known to the skilled person and may include yellow circular spots with an oily appearance on grapevine leaves and pale green to brownish-black lesions on tomato leaves respectively incited by *Plasmopara viticola* and *Phytophthora infestans* attacks. Accordingly, in preferred embodiments, the uses and methods disclosed herein are for treating plants that show symptoms of plant disease, such as visible signs of plant disease.

Generally, further embodiments may be taken from the Examples disclosed herein, and also from the further considerations in Example 8 herein below.

The foregoing embodiments and teachings are generally applicable herein.

In an eleventh aspect, the invention relates to an isolated polypeptide selected from i) a polypeptide having the sequence of SEQ ID NO: 2, ii) a polypeptide having the sequence of SEQ ID NO: 4, iii) a copper translocating P-type ATPase obtainable from deposit CBS 134400, iv) a copper resistance protein A obtainable from deposit CBS 134400, v) a polypeptide having a sequence that has at least 70% identity to the sequence of SEQ ID NO: 2, and/or vi) a polypeptide having a sequence that has at least 70% identity to the sequence of SEQ ID NO: 4.

In certain embodiments, the isolated polypeptide (particularly that of alternative v) above) is a polypeptide having a sequence that has at least 75% (particularly at least 80%, especially at least 90%, in particular at least 95%) identity to the sequence of SEQ ID NO: 2.

In certain embodiments, the isolated polypeptide is a copper translocating P-type ATPase having a sequence that has at least 70% (particularly at least 75%, 80%, 90%, or 95%) identity to the sequence of SEQ ID NO: 2, and/or being obtainable from deposit CBS 134400.

In certain embodiments, the isolated polypeptide (particularly that of alternative vi) above) is a polypeptide having a sequence that has at least 75% (particularly at least 80%, especially at least 90%, in particular at least 95%) identity to the sequence of SEQ ID NO: 4.

In certain embodiments, the isolated polypeptide is a copper resistance protein having a sequence that has at least 70% (particularly at least 75%, 80%, 90%, or 95%) identity to the sequence of SEQ ID NO: 4, and/or being obtainable from deposit CBS 134400.

In a twelfth aspect, the invention relates to an isolated nucleic acid selected from a nucleic acid i) encoding a polypeptide according to items i), iii) or v) of the eleventh aspect; ii) encoding a polypeptide according items ii), iv) or vi) of the eleventh aspect; iii) having the sequence of SEQ ID NO: 1 (ctpA); iv) having the sequence of SEQ ID NO: 3 (copA); v) having a sequence that has at least 99% identity to a sequence as defined in any of the above items i) and iii) of the twelfth aspect; vi) having a sequence that has at least 99% identity to a sequence as defined in any of the above items ii), and iv) of the twelfth aspect; vii) encoding the same peptide as a sequence as defined in any one of the above items i) to vi) of the twelfth aspect; and/or viii) capable of hybridizing under stringent conditions to a nucleic acid as defined in any of the above items i) to vii) of the twelfth aspect.

In a particular embodiment, the isolated nucleic acid is capable of hybridizing under stringent conditions to a nucleic acid, whose sequence is SEQ ID NO: 1.

In a particular embodiment, the isolated nucleic acid is capable of hybridizing under stringent conditions to a nucleic acid, whose sequence is SEQ ID NO: 3.

In particular embodiments, the isolated nucleic acid is capable of hybridizing under stringent conditions to a nucleic acid, whose sequence has at least 99% identity to SEQ ID NO: 1 or SEQ ID NO: 3.

In particular embodiments, the isolated nucleic acid is capable of hybridizing under stringent conditions to a nucleic acid, whose sequence encodes the same peptide as a sequence of SEQ ID NO: 1 or SEQ ID NO: 3.

The subject-matter of the eleventh and twelfth aspect is closely correlated to other aspects herein, since it is considered to play an important role in the copper resistance of e.g. the bacterial strain AZ78. Without intending to be bound by theory, the present inventors assume that the product of the ctpA gene is involved in the detoxification of bacterial cell and acts by pumping out copper ions from bacterial cell—and that the copA gene is coding for a copper oxidase that is involved in the oxidation of copper ions. Accordingly, said genes and proteins may advantageously be employed e.g. in various other *Lysobacter* bacteria or *Lysobacter capsici* bacteria. *Lysobacter* bacteria comprising one or more of said nucleotide sequences and/or polypeptides are additionally envisaged as embodiments herein. Likewise, in preferred embodiments herein, the bacteria of the invention comprise a ctpA gene and/or its gene product. Likewise, in preferred embodiments herein, the bacteria of the invention comprise a copA gene and/or its gene product. Likewise, in preferred embodiments herein, the bacteria of the invention comprise a copA and a ctpA gene and/or their gene products.

The Lysobacter capsici strain AZ78 described herein was deposited, pursuant to the Budapest Treaty on the International Recognition of the Deposit of Microorganisms for the Purposes of Patent Procedure, on Feb. 21, 2013, with the Centraalbureau voor Schimmelcultures (CBS), an established International Depositary Authority (IDA) located at Uppsalalaan 8, P.O. Box 85167, 3508 AD UTRECHT, The Netherlands, and has been assigned accession number CBS 134400.

Accordingly, generally in certain embodiments herein, reference to a strain AZ78, a *Lysobacter capsici* AZ78, a *Lysobacter capsici* strain AZ78 and suchlike expressions may be replaced by reference to strain CBS 134400, a *Lysobacter capsici* CBS 134400, a *Lysobacter capsici* strain CBS 134400 and suchlike expressions. Likewise, in particular embodiments of the present invention, reference to a strain AZ78, an *Lysobacter capsici* AZ78, a *Lysobacter capsici* strain AZ78 and suchlike expressions may be replaced by reference to a strain deposited as CBS 134400, a *Lysobacter capsici* deposited as CBS 134400, a *Lysobacter capsici* strain deposited as CBS 134400 and suchlike expressions.

The above explicitly also applies as to the respective bacteria and bacterial preparations in context with the present invention.

EXAMPLES

The following examples are meant to further illustrate, but not limit, the invention. The examples comprise technical features, and it will be appreciated that the invention also relates to any combinations of the technical features presented in this exemplifying section.

Example 1

Exemplary Materials and Methods a. Microorganisms and Plants

*Lysobacter capsici* AZ78 was long term stored in glycerol 40% at −80° C. and routinely grown on Luria Bertani Agar (LBA) in Petri dishes (90 mm diameter) at 27° C. In each experiment, suspensions of AZ78 cells were prepared according to the following procedure: AZ78 was grown for 72 h and bacterial cells were then collected in 5 ml of sterile saline solution (NaCl 0.85%) and transferred to sterile 15 ml tubes. Bacterial cell suspensions were centrifuged (10 000 rpm, 5 min) and pellets were suspended in sterile distilled water to a final optical density at 600 nm ($A_{OD600nm}$) of 0.1 corresponding to ≈$1\times10^8$ CFU $ml^{-1}$. This bacterial concentration was used in all experiments.

All the experiments regarding the biological control of *Plasmopara viticola* were carried out on two-year-old plants of the susceptible grapevine cultivar *Vitis vinifera* cv. Pinot Noir grafted onto Kober 5BB rootstock. Plants were grown in controlled greenhouse conditions (20±0.5° C.; 70±10% relative humidity, RH) in 2.5 L pots containing a mixture of peat and pumice (3:1) for two months until the plants had produced two shoots with at least nine leaves each.

The biocontrol activity of *Lysobacter capsici* AZ78 towards *Phytophthora infestans* has been evaluated in experiments carried out on tomato plantlets (*Solanum lycopersicum* cv. Tondo rosso). In each experiment, tomato seeds were let to pre-germinate by maintaining them at room temperature on sterile filter paper in Petri dishes until the root become visible (96 h). Then, pre-germinated seeds were sown in sterile 50 ml-pots containing sterile peat and grown at 25° C. in clean greenhouse with a 16-h photoperiod. Tomato plantlets were employed in biocontrol experiments of *Phytophthora infestans* when four leaves were produced (approximately one month after planting).

*Plasmopara viticola* was isolated from an untreated vineyard in S. Michele all'Adige (Italy) in 2011 and maintained on grapevine plants by subsequent weekly inoculations. To obtain sporangia, plants with oil spot symptoms were kept overnight in the dark at 20-21° C. and 100% RH. An inoculum of *Plasmopara viticola* was prepared by washing the lower side of grapevine leaves exhibiting freshly sporulating lesions with cold (4-5° C.) distilled water. *Phytophthora infestans* was maintained onto pea agar (125 g of frozen pea, 1.5% agar per liter of distilled water) at 17° C. Fresh sporangia were collected from inoculated plates by adding cold distilled water into the plates and by scraping the mycelial surface using sterile spatulas. In both cases, the sporangia suspension was adjusted to a concentration of $2\times10^5$ sporangia $ml^{-1}$ by counting with a haemocytometer under a light microscope.

b) Determining AZ78 Resistance to Copper

The ability of AZ78 to survive on agar medium amended with copper ions ($Cu^{2+}$) was assessed according to Ritchie and Dittapongpitch (1991) with some modifications. Briefly, volumes of a filter-sterilised copper sulphate solution ($CuSO_4$, Sigma) were added to LBA then poured into Petri dishes in order to obtain the following final concentrations of $CuSO_4$: 100, 200, 300, 400 and 500 μg $ml^{-1}$. For each copper concentration, three Petri dishes were spot inoculated with three drops (30 μl) of a AZ78 cell suspension ($1\times10^8$ CFU $ml^{-1}$) and plates were incubated for 72 h at 27° C. The development of macrocolonies on the medium reflected the ability of AZ78 to tolerate increasingly high copper concentrations (Ritchie and Dittapongpitch, 1991). Confirmation of the degree of resistance to copper was obtained by spreading 100 μl of a serial dilution ($10^{-1}$ to $10^{-7}$) of the AZ78 cell suspension onto LBA and LBA amended with copper sulphate at the concentrations mentioned above. Colony forming units were counted after an incubation period of four days at 27° C. Three plates of each combination (dilution and copper concentration) were prepared and the experiment was repeated twice. The survival ratio (SR) was obtained by dividing the treated population (grown on LBA amended with $CuSO_4$) by the untreated population (grown on LBA only), according to Stockwell et al., (2009).

Genomic DNA of AZ78 was extracted with a Genomic DNA isolation Kit (Qiagen) and used as the template in the PCR reactions aimed at detecting the presence of genes involved in the resistance to copper ions. The method developed by De la Iglesia et al., (2010) and Pavissich et al., (2010) was adopted in order to detect the gene ctpA coding for copper $P_{1B}$-type ATPases, which are involved in copper efflux, while the method developed by Lejon et al., (2007) was employed for the detection of the gene copA coding for a copper oxidase. The to primer pairs copAUF (5'-GGT GCT GAT CAT CGC CTG-3')/copAUR (5'-GGG CGT CGT TGA TAC CGT-3'), Coprun F2 (5'-GG SA SBTACTGG-TRBCAC-3')/Coprun R1 (5'-TGNGHCATCATSGTRT-CRTT-3') (primer sequences: cf. SEQ ID NOs 14-17) and the same mixture composition and temperature cycles as reported respectively by Pavissich et al., (2010) and Lejon et al., (2007) were used in the PCR reactions. PCR products were purified using Exo-Sap (Euroclone S.p.a., Italy) according to the manufacturer instructions. Once purified, DNA amplicons were sequenced using BigDye Terminator v 3.1 and the resulting nucleotide sequences were analysed by BLASTN search to find homologies with DNA sequences already deposited in GenBank. On the basis of DNA homologies new primer pair combinations were designed in order to obtain the full nucleotide sequence of ctpA and copA in *Lysobacter capsici* AZ78. Experiments were carried out twice.

c) Biological Control Experiments i) The ability of AZ78 to control downy mildew on grapevine plants was assessed under controlled greenhouse conditions. AZ78 in combination with a copper-based fungicide (Kocide 3000, 15% copper hydroxide WG, Du Pont de Nemours, USA) at low dosages was also assessed in these experiments. The following treatments were applied: A) untreated; B) Kocide 3000 at 2.5 g $L^{-1}$; C) Kocide 3000 at 1.25 g $L^{-1}$; D) Kocide 3000 at 0.6125 g $L^{-1}$; E) AZ78+Kocide 3000 at 1.25 g $L^{-1}$; F) AZ78+Kocide 3000 at 0.6125 g $L^{-1}$; G) AZ78.

The upper and lower leaf surfaces of the plants were sprayed twice with AZ78 cell suspension, 24 and 6 h before *Plasmopara viticola* inoculation, using a hand spraying device (treatments E, F and G) and with water (untreated control) and Kocide 3000 (treatments B, C, D, E and F) six hours before application of the pathogen using a compressed air hand sprayer. Each plant was sprayed with 40 ml of each treatment preparation.

*Plasmopara viticola* inoculum, prepared as described above, was sprayed onto the abaxial surface of each fully expanded leaf using a compressed air hand sprayer. Inoculated plants were subsequently incubated at 20±0.5° C. (80-99% RH) in the dark for 24 h, then maintained at 25° C. (60-80% RH) with a 16/8-h day/night light regime. Seven days after inoculation, plants were incubated overnight in the dark at 20±0.5° C. and 80-99% RH to stimulate sporulation.

Disease severity (percentage of abaxial leaf area covered with sporulating lesions) and disease incidence (percentage of leaves with visible sporulation) were evaluated at the end of the experiments (cf. e.g. FIG. 3A). Disease was assessed in terms of continuous quantitative variables based on the EPPO standard scale (EPPO, 2004) and expressed as percentages. Each treatment was carried out on five replicates (plants) and independent experiments were carried out three times.

ii) The biological control of tomato late blight through the application of AZ78 was assessed under controlled greenhouse conditions. Also in this case, AZ78 was employed in combination with Kocide 3000. The following treatments were applied: 1) untreated; 2) Kocide 3000 at 2.5 g $L^{-1}$; 3) Kocide 3000 at 0.6125 g $L^{-1}$; 4) AZ78+Kocide 3000 at 0.6125 g $L^{-1}$; 5) AZ78. The upper and lower leaf surfaces of tomato plants were sprayed twice with AZ78 cell suspension, 24 and 6 h before *Phytophthora infestans* inoculation, using a hand spraying device (treatments 3, 4 and 5) and with water (1) and Kocide 3000 (treatments 2, 3 and 4) six hours before application of the pathogen using a compressed air hand sprayer. Each plant was sprayed with 20 ml of each treatment preparation. *Phytophthora infestans* inoculum, prepared as described above, was sprayed onto the entire tomato plant. The plants were kept at 100% RH in the dark at 18° C. for 24 hours and then placed in a growth cabinet at 18° C. Tomato leaves were scored after 5 days and disease severity (percentage of leaf area showing symptoms) and disease incidence (percentage of symptomatic leaves) were evaluated at the end of the experiments (cf. e.g. FIG. 3B). Each treatment was carried out on five replicates (plants) and independent experiments were carried out three times.

AZ78 populations on grapevine and tomato leaves were monitored one hour before the inoculation of the plant pathogenic oomycetes and at the end of the experiments by the dilution plating method. At these two time points, leaf samples of 5 g were collected from plants of each treatment. They were cut and put individually into 100 ml bottles containing 45 ml of sterile saline solution and shaken (200 rpm) for two hours at room temperature. Aliquots of the suspensions were serially diluted and spread onto the surface of LBA amended with kanamycin (50 μg $ml^{-1}$), since AZ78 is naturally resistant to this antibiotic (unpublished). Plates were then incubated for 72 h at 27° C. and colonies resistant to kanamycin with AZ78 colony morphology were counted to determine the amount of AZ78 cells $g^{-1}$ on the grapevine and tomato leaves. The experiment was repeated.

d) AZ78 Persistence on Grapevine Leaves

Greenhouse experiments were carried out to monitor AZ78 persistence on grapevine leaves at two RH levels. Ten grapevine plants were sprayed once with AZ78 suspension following the procedure described above. Over the following ten days, half of the AZ78-treated plants were maintained at 25° C. (70±10% RH) and the other half were maintained at the same temperature but at 90±10% RH. At 1, 3, 6, 8 and 10 days post-application, AZ78 persistence on grapevine leaves was assessed by the dilution plating method described above. The experiment was repeated.

e) Biofilm Production in a Microtitre Plate.

Strain AZ78 was evaluated for its ability to form biofilms on polystyrene microtitre plates using a modified version of the procedure described by Maddula et al., (2006). A volume of 1.5 μl of AZ78 suspension was inoculated into 150 μl per well of three liquid media, LB, King's B (KB) and Nutrient Broth (NB), in 96-well polystyrene plates. Additional wells were not inoculated with the bacterium as negative controls. Plates were incubated at 27° C. for 60 h without shaking and final cell densities were determined ($A_{OD600nm}$). Unattached cells were removed by inverting the plate and tapping it onto absorbent paper. The remaining adherent bacterial cells were fixed to the plates for 20 min at 50° C. and then stained for 1 min with 150 μl per well of crystal violet solution (0.1% in sterile distilled water). Excess stain was removed by inverting the plate then washing twice with distilled water (each wash 250 μl per well). Adherent cells were decolorized with an acetone/ethanol (20%/80%) solution (200 μl per well) for 5 min to release the dye into the solution. A volume of 100 μl was transferred from each well to another 96-well plate and the amount of dye (proportional to the density of adherent cells) was quantified ($A_{OD540nm}$). A 96-well polystyrene plate was used for each time point in the time-course experiment. Twenty wells were filled with each of the tested growth media in each microtitre plate. AZ78 cells were simultaneously inoculated in half of the wells containing the growth media. Cell density and biofilm formation were determined at time zero and at 12 h intervals until 60 h after inoculation (six time points). $A_{OD540nm}$ values (adherent cells) were divided by $A_{OD600nm}$ values (bacterial growth) in order to obtain the specific biofilm formation value (SBF). The experiment was repeated.

f) Evaluating AZ78 Tolerance to Environmental Stresses

Stress response experiments were carried out on suspensions of AZ78 according to Stockwell et al., (2005, 2009)

with some modifications. Briefly, tolerance to starvation stress was assessed by inoculating AZ78 in 15 ml sterile tubes containing 5 ml of sterile potassium phosphate buffer (1 mM, pH 7) and 0.8% NaCl to obtain a final concentration of $1\times10^8$ CFU $ml^{-1}$. Inoculated tubes were maintained at 27° C. for 15 days on a rotary shaker at 200 rpm. AZ78 cell density was assessed by the dilution plating method at 0, 3, 6, 9, 12 and 15 days post-inoculation. SR was calculated by dividing the population at days 3, 6, 9, 12 and 15 by the population at the beginning of the experiment (0 days after inoculation). Three tubes were inoculated for each day.

Tolerance to mild heat shock was measured by incubating sterile 1.5 ml microfuge tubes containing 100 μl of AZ78 cell suspension for 20 min at the following temperatures: 30, 33, 36, 39 and 42° C. After this period, a volume of 900 μl of potassium phosphate buffer (1 mM, pH 7) was added and the suspension was mixed in a vortex for 30 s prior to dilution plating. SR was calculated by dividing the AZ78 population after exposure to each temperature by the population after exposure to 27° C. Three microfuge tubes were used for each temperature.

Tolerance to freezing was assessed by transferring 100 μl aliquots of AZ78 cell suspension into sterile 1.5 ml microfuge tubes that were maintained at −20° C. for 24 h. The viability of AZ78 cells was assessed at 6, 12, 18 and 24 h. At these time points, a volume of 900 μl of 10 mM phosphate buffer (pH 7) was added to each tube immediately after being removed from the freezer. Samples were gently mixed by pipetting and serially diluted in sterile SS ($10^{-1}$ to $10^{-7}$). Volumes of 100 μl of these dilutions were spread onto LBA and enumerable colonies were counted after four days of incubation at 27° C. Three microfuge tubes were used for each time point. SR was calculated by dividing the population after exposure to −20° C. by the population which was not exposed to freezing.

In order to evaluate tolerance to ultraviolet irradiation, dilutions of AZ78 cell suspension ($10^{-1}$ to $10^{-7}$) were spread onto LBA and immediately exposed to UV irradiation (λ 254 nm) at the following doses: 20, 40, 60, 80 and 100 J $m^{-2}$. Following exposure, plates were incubated at 27° C. in the dark for four days, after which colony forming units were counted. Three replicates (Petri dishes) were used for each dilution. SR was calculated by dividing the population after exposure to UV irradiation by the population of AZ78 cells which were not exposed to UV.

All the above-described experiments were carried out at least twice.

g) Statistical Analysis

A two-way ANOVA was carried out on data from the experiments carried out to assess ability to form biofilm ($A_{OD600nm}$ and SBF) and to tolerate copper ions and environmental stresses (SR) to see whether these data could be pooled. SR values obtained from the experiments evaluating tolerance to abiotic stresses and copper ions were $\log_{10}$ transformed beforehand.

Once pooled, data were analysed by ANOVA using the Statistica 7.1 software programme (StatSoft, Tulsa, Okla., USA) and means were compared with a Tukey's test (α=0.01).

Values of disease incidence and disease severity obtained from the greenhouse trials were arcsine-transformed prior to the two-way ANOVA. Once pooled, data were analysed according to the statistical method reported above.

Example 2

*Lysobacter capsici* AZ78 developed macrocolonies when spotted onto LBA amended with copper at concentrations ranging from 100 to 500 μg $ml^{-1}$. Further experiments showed that amendment of copper sulphate to LBA decreased the AZ78 cell density of a tenfold only when the final concentration was 500 μg $ml^{-1}$ (FIG. 1). A concentration of 400 μg $ml^{-1}$ resulted in a logarithmic SR value of −0.42±0.16 while lower concentrations did not cause any particular decrease in AZ78 cell viability (FIG. 1). AZ78 released a brown pigment into the medium when grown on LBA amended with $CuSO_4$ at 400 and 500 μg $ml^{-1}$ concentrations (data not shown).

Example 3

PCR to detect the DNA region associated with the copper-translocating $P_{1B}$-type ATPase (gene ctpA) resulted in amplification of a 726 bp amplicon. The amplicon was sequenced and the resulting nucleotide region was analysed by BLASTN. The highest homology value was found with the gene coding for a $P_{1B}$-type ATPase from the complete genome of *Pseudoxanthomonas suwonensis*, a bacterial species taxonomically related to the genus *Lysobacter*. An 1107 bp region was amplified by using the primer pair specific for copA gene. This sequence showed the highest homology with the gene coding for a copper oxidase from the complete genome of *Stenotrophomonas malthophdia* strain JV3. On the basis of these homologies new primer pairs were designed in order to obtain the complete nucleotide sequence of ctpA and copA in *Lysobacter capsici* AZ78.

Example 4

In light of these results, *Lysobacter capsici* AZ78 was evaluated alone and in combination with a low dose of the copper-based fungicide Kocide 3000, used to control *P. viticola*, under controlled environmental conditions (greenhouse). A huge reduction in the severity of downy mildew was recorded after AZ78 was applied to the grapevine leaves. Where plants were treated with AZ78 only, the mean percentage of leaf area covered with sporulating lesions was 5% whereas the mean for untreated leaves was 67% (Table 1). With respect to disease incidence, the percentage of leaves with visible sporulation was lower on plants treated with AZ78 than on plants treated with water only (100%), but it was not significantly different from copper-treated plants (Table 1). Symptoms were evident on 63% of the leaves of AZ78-treated plants, while on the plants treated with copper at the various doses (2.5, 1.25 and 0.6125 g $L^{-1}$) 73, 76 and 83%, respectively, of leaves were symptomatic (Table 1). The reduction in disease severity resulting from application of AZ78 was not significantly different from the reduction effected by copper (Kocide 3000) at the various doses (Table 1). However, the combination of AZ78 and copper in low doses (1.25 and 0.6125 g $L^{-1}$) reduced the incidence of disease to a greater extent than when the various concentrations of copper or AZ78 were applied alone (Table 1). Disease severity, on the other hand, was not significantly reduced by the combination compared with plants treated with AZ78 or copper alone (Table 1). Exemplary results of these experiments are additionally depicted in FIGS. 2 and 3A.

TABLE 1

| Treatments | Disease incidence[b] | Disease severity[b] |
|---|---|---|
| Untreated[a] | 100 ± 3 a | 67 ± 27 a |
| Kocide 3000 (2.5 g $L^{-1}$) | 63 ± 16 b | 3 ± 2 b |

TABLE 1-continued

| Treatments | Disease incidence[b] | Disease severity[b] |
|---|---|---|
| Kocide 3000 (1.25 g $L^{-1}$) | 66 ± 10 b | 8 ± 22 b |
| Kocide 3000 (0.6125 g $L^{-1}$) | 73 ± 11 b | 5 ± 5 b |
| *Lysobacter capsici* AZ78 + Kocide 3000 (1.25 g $L^{-1}$) | 30 ± 14 c | 2 ± 2 b |
| *Lysobacter capsici* AZ78 + Kocide 3000 (0.6125 g $L^{-1}$) | 39 ± 13 c | 1 ± 1 b |
| *Lysobacter capsici* AZ78 | 63 ± 9 b | 5 ± 5 b |

Biocontrol of *Plasmopara viticola* through prophylactic application of *Lysobacter capsici* AZ78 on grapevine leaves. Disease incidence is expressed as the percentage of symptomatic leaves while disease severity is expressed as the percentage of leaf area covered with sporulating lesions.

[a]Untreated: plants treated with water only.

[b]Mean values ± standard deviations are reported for each treatment. The same letters indicate values which do not differ significantly according to Tukey's test (α = 0.01).

At the same time, combination of *Lysobacter capsici* AZ78 with Kocide 3000 was evaluated also for the control of *Phytophthora infestans* on tomato plants. An important reduction in the severity of tomato late blight was observed on tomato plants treated with AZ78 compared to untreated tomato plants (Table 2). The application of AZ78 only determined a reduction of disease incidence and disease severity equal to the reduction achieved through the employment of Kocide 3000 at low dosage (0.6125 g $L^{-1}$) (FIGS. 3B and 4). An increase in the control of *Phytophthora infestans* was recorded when AZ78 was combined with Kocide 3000 at low dose, obtaining a reduction of disease incidence not statistically different from the reduction obtained with Kocide 3000 at high dose (2.5 g $L^{-1}$) (FIG. 4; Table 2).

TABLE 2

| Treatments | Disease incidence[b] | Disease severity[b] |
|---|---|---|
| Untreated[a] | 96 ± 6 a | 100 ± 0 a |
| Kocide 3000 (2.5 g $L^{-1}$) | 0 ± 0 b | 0 ± 0 c |
| Kocide 3000 (0.6125 g $L^{-1}$) | 6 ± 4 b | 13 ± 5 b |
| *Lysobacter capsic*i AZ78 + Kocide 3000 (0.6125 g $L^{-1}$) | 1 ± 1 b | 2 ± 1 c |
| *Lysobacter capsici* AZ78 | 5 ± 4 b | 17 ± 6 b |

Biocontrol of *Phytophthora infestans* through prophylactic application of *Lysobacter capsici* AZ78 on tomato leaves. Disease incidence is expressed as the percentage of symptomatic leaves while disease severity is expressed as the percentage of leaf area showing symptoms.

[a]Untreated: plants treated with water only.

[b]Mean values ± standard deviations are reported for each treatment. The same letters indicate values which do not differ significantly according to Tukey's test (α = 0.01).

At neither of the two time points AZ78 cells were isolated from leaves of grapevine and tomato plants treated with water or from leaves of plants treated with the different doses of Kocide 3000 only, but they were recovered from leaves of plants treated with AZ78. An AZ78 population of 5.07±0.16 $\log_{10}$ CFU $g^{-1}$ of leaf was recovered from grapevine leaves collected one hour before *Plasmopara viticola* inoculation and a similar population size (5.22±0.02 $\log_{10}$ CFU $g^{-1}$ of leaf) was obtained at the end of the trial. In plants treated with both AZ78 and copper, a reduction of an order of magnitude of AZ78 population size was recorded. At the end of the experiments, the bacterium was recovered at 4.36±0.12 and at 4.28±0.14 $\log_{10}$ CFU $g^{-1}$ of leaf on plants treated with copper at doses of 1.25 and at 0.6125 g $L^{-1}$, respectively. Similar results were achieved in the biocontrol experiments for tomato late blight.

Example 5

In the experiments assessing AZ78 persistence on grapevine leaves over ten days, AZ78 was recovered one day after application at 5.41±0.07 and 6.57±0.50 $\log_{10}$ CFU $g^{-1}$ of leaf of plants kept at normal (60-80%) and high (80-99%) relative humidity, respectively (cf FIG. 5). AZ78 persisted at a constant rate for 10 days on plants exposed to high humidity (6.47±0.16 $\log_{10}$ CFU $g^{-1}$ of leaf after ten days) while at normal humidity the AZ78 population was constant until the $6^{th}$ day post-inoculation and then decreased to 2.39±0.04 $\log_{10}$ CFU $g^{-1}$ of leaf after 8 days; AZ78 was still present after ten days, but at a low concentration (2.24±0.24 $\log_{10}$ CFU $g^{-1}$ of leaf).

Example 6

Given these high survival rates, the present inventors investigated the ability of AZ78 to form biofilm on inert surfaces. Strain AZ78 was grown differently in the three media used in the biofilm production assay and KB was found to be the medium that sustained the highest cell production with a value of $A_{OD600nm}$ (FIG. 6A). Bacterial growth in the other two liquid media, LB and NB, was almost identical and after 60 h AZ78 reached $A_{OD600nm}$ (FIG. 6A). Nonetheless at this time point the SBF value registered in NB was higher than the quantity reached in LB (FIG. 6B). Biofilm was not produced in LB until 48 h and it attained its highest value (SBF=2.62±0.04) after 60 h; AZ78 started to form biofilm between 24 and 36 h in NB (FIG. 6B); the highest SBF value in KB was reached at 12 h and thereafter decreased (FIG. 6B).

Example 7

The present inventors sought to explain the high persistence on grapevine leaves by investigating AZ78 resistance to different abiotic stresses in a series of in vitro experiments. In the first set of experiments, aimed at assessing resistance to starvation, AZ78 was incubated in phosphate buffer and the concentration was monitored over fifteen days. The viability of AZ78 cells slowly decreased and by the end of the experiments the total reduction was 0.70±0.13 $\log_{10}$ CFU $ml^{-1}$. Mild heat shock was induced by exposing AZ78 cell suspension to temperatures ranging from 30 to 42° C. for twenty minutes. Exposure to 30 and 33° C. did not result in any loss of cell viability whereas exposure to 36, 39 and 42° C. reduced viability by $\log_{10}$−0.19±0.06, −0.12±0.08 and −0.35±0.18, respectively.

Incubation at −20° C. slightly decreased the viability of AZ78 cells, although by less than an order of magnitude at all the time points in this experiment and the differences were not significant (FIG. 7A). With respect to AZ78 tolerance to UV light irradiation, the survival ratio drastically decreased when the strain was exposed to 60, 80 and 100 J $m^{-2}$, the reduction being almost six-tenfold, while exposure to 20 and 40 J $m^{-2}$ reduced viability by $\log_{10}$−1 and $\log_{10}$−3, respectively (FIG. 7B).

Example 8

Conclusions and Further Examples and Considerations

Identification of novel microorganisms which are able to effectively control *Plasmopara viticola* and *Phytophthora infestans* may play an important role in lowering the detrimental impact on the environment resulting from frequent use of fungicides/plant protection products to control grapevine downy mildew and tomato or potato late blight. To the best of the inventors' knowledge, *Lysobacter capsici* AZ78 is one of the few bacterial strains being used as biological control agents to control grapevine downy mildew (Tilcher et al., 1994, 2002). Building on this knowledge, the inventors' study e.g. provides the first evidence of copper-tolerance in a member of the *Lysobacter* genus. Without intending to be bound by theory, this characteristic is probably associated with the presence of two genes involved in copper resistance. A first gene in AZ78 genome shows high sequence homology with a gene coding for a copper $P_{1B}$-type ATPase, which is present in the genome of *Pseudoxanthomonas suwonensis*, another member of the Xanthomonadaceae family. These ATPases belong to the heavy metal transporter ATPases, ubiquitous membrane proteins deputed to the efflux of copper ions in various microorganisms (Fu et al., 1995; Ge et al., 1995; Petersen and Møller, 2000; Arguelo et al., 2007). A second gene shows high homologies with a gene coding for a copper oxidase present in the genome of *Stenotrophomonas malthophilia* JV3. The gene copA is coding for enzymes that are involved in the copper sequestration and/or copper transformation mechanisms shared by several bacterial species (Cooksey, 1994; Rensing and Grass, 2003)

This characteristic is remarkable since copper is routinely applied in the control of *Plasmopara viticola* and *Phytophthora infestans* and the existence of a biocontrol agent/plant protection product which tolerates copper ions opens up the possibility of combining this agent with low doses of copper in order to reduce the use of copper-based fungicides in organic cultivation (Dagostin et al., 2011). The present inventors found that simultaneous application of AZ78 and copper enhanced plants' protection against *Plasmopara viticola* and *Phytophthora infestans* compared with the application of AZ78 or copper alone. Moreover, application of copper to AZ78-treated plants reduced the AZ78 cell population by an order of magnitude, showing that the decrease in cell viability observed in vitro is partially conserved in planta.

Application of AZ78 cells to grapevine leaves e.g. resulted in a reduction in the percentage of abaxial leaf area covered by *Plasmopara viticola* sporulating lesions comparable to that following application of a copper-based fungicide (general note: the term "copper-based fungicide" is used equivalently herein with the term "copper-based plant protection product"). Even though this is not considered of particular relevance in practicing the present invention, it may be interesting to conduct future research to investigate the mechanisms underlying the ability of *Lysobacter capsici* AZ78 to control e.g. grapevine downy mildew in planta and whether these mechanisms are modulated when the bacterium is in the presence of copper-based fungicides.

The AZ78 populations on grapevine leaves under controlled conditions were similar at the beginning and at the end of the biocontrol experiments. In particular concurrent experiments aimed at monitoring the persistence of AZ78 cells on grapevine leaves, the present inventors showed that the AZ78 population remains constant until six days after application to plants maintained at 25° C. with a 60-80% RH. However, there were some differences between the degree of persistence measured in the biocontrol experiments and that measured in the experiments specifically designed to assess AZ78 persistence. In the latter experiments, the AZ78 population decreased over 8 days from $10^5$ to $10^2$ cells per gram of leaf, while after the same period $10^5$ cells per gram of leaf were recovered from plants in the biocontrol experiments. This difference may be due to the different conditions the bacterium encountered during the two experiments. While humidity remained constant over the ten days of the persistence experiments, during the biocontrol experiments relative humidity was increased twice, upon infection and upon sporulation of *Plasmopara viticola*. This explanation is confirmed by the constant persistence of AZ78 on plants maintained at high HR for the entire duration of the persistence experiments. Humidity is known to influence bacterial growth (Leben, 1988; Wilson et al., 1999; Cooley et al., 2003), so that high humidity contributes to sustaining a large AZ78 population on leaves. In any case, the skilled person will easily be able to account for issues connected to an influence of humidity based on his knowledge in the art.

It is also worth noting that AZ78 survives well in the grapevine phyllo sphere although it was isolated from the rhizosphere of tobacco plants (unpublished). At the present time, most of the *Lysobacter* strains evaluated for biological control of plant diseases have been isolated from the soil or rhizosphere of cultivated plants, with the single exception of *Lysobacter enzymogenes* C3, which was obtained from the phylloplane of Kentucky bluegrass (Giesler and Yuen, 1998). As a consequence, only this strain has been evaluated for biocontrol of plant pathogens that attack the parts of the plant that grow above the ground (Kilic-Ekici and Yuen, 2003; Kobayashi and Yuen, 2005; Jochum et al., 2006) while most of the *Lysobacter* strains have been evaluated for biocontrol of soil-borne pathogenic fungi and oomycetes (Nakayama et al., 1999; Rondon et al., 1999; Folman et al., 2003; Postma et al., 2008; Puopolo et al., 2010). The results of the inventors' study suggest that soil-borne *Lysobacter* species may also be used for biological control of pathogenic microorganisms that attack the aerial parts of the plants.

Given the persistence on the leaf surface, the present inventors decided to investigate the potential of AZ78 to form biofilm, since it is well documented that bacteria survive on plant surfaces by forming large aggregates (biofilm) (Morris et al., 1997; Dulla and Lindow, 2008). However, little is known about biofilm formation by *Lysobacter* strains. Islam et al. (2005) showed that strain SB-K88 forms dense microcolonies on the rhizoplane of sugar beet plantlets grown from seeds coated with this bacterium and they also reported that SB-K88 adheres to the plant surface by forming fimbriae. The present inventors investigated the ability of AZ78 to form biofilm on inert surfaces in the inventors' study and this is the first time that a *Lysobacter capsici* strain has been shown to form biofilm in vitro. The degree of this ability, however, depended on the composition of the growth medium as evidenced by the fact that the KB medium sustained development of the greatest quantity of bacterial cells but without leading to the formation of bio film. In any case, suitable growth media can easily be established by the skilled person. Since KB contains low amounts of available iron ions (King et al., 1954), it is reasonable to assume that this metal affects the formation of biofilm by *Lysobacter capsici* AZ78, as it does other Gram-negative bacteria such as *Acinetobacter baumannii* and *Pseudomonas aeruginosa*, where biofilm formation is highly influenced by iron source, concentration and bioavailability (Tomaras et al., 2003; Banin et al., 2005). Moreover, it has previously been shown that the other *Lysobacter capsici* member, strain PG4, is unable to produce siderophores and that supplementing the KB medium with $FeCl_3$ enhances its antibacterial properties (Puopolo et al., 2010). Given these data, but without intending to be bound by theory, the present inventors assume that iron availability may play an important role in the persistence in the environment and biocontrol potential of *Lysobacter capsici* members. When bacteria form a biofilm they become more resistant to various environmental factors that affect their persistence (Ophir and Gutnick 1994; Perrot et al., 1998; Elasri and Miller, 1999). The most frequently investigated limiting environmental factors for bacterial persistence in the phyllosphere are starvation, temperature and exposure to UV light (Wilson et al., 1999; Stockwell et al., 2009). Since little is known about the ability of *Lysobacter* species to survive following exposure to these factors, the present inventors wanted to investigate how AZ78 responds to them.

The viability of AZ78 cells was not negatively affected by stress caused by lack of nutrients (starvation) nor did they suffer following exposure to increasing temperatures (mild heat shock). Interestingly, AZ78 was able to tolerate exposure to UV irradiation and freezing temperatures (−20° C.). The survival ratio of AZ78 cells after exposure to these environmental stresses was comparable with that of the epiphytic strain *Pseudomonas fluorescens* 122 and of the soil-borne strain *Pseudomonas fluorescens* Pf5, as reported by Stockwell et al. (2009). AZ78 cell viability was not negatively affected by the lowest UV irradiation dose tested in this study (20 J $m^{-2}$). Sundin and Jacobs (1999) reported that the minimum inhibitory dose for the UV-sensitive strain *Pseudomonas aeruginosa* PAO1 was 5 J $m^{-2}$, from which the present inventors conclude that the sensitivity threshold of strain AZ78 is higher than that of a sensitive bacterial strain.

The results presented by the present inventors e.g. show that *Lysobacter capsici* strain AZ78 is particularly suitable for new sustainable strategies for controlling plant diseases, since it can e.g. establish itself in the grapevine and tomato phyllosphere, can tolerate environmental stresses and, most importantly, drastically reduces the severity of e.g. grapevine downy mildew and tomato late blight. Moreover, *Lysobacter capsici* strain AZ78 is particularly useful as it is resistant to copper.

Example 9

To test the advantageous features of the bacteria of the present invention also in other contexts, the influence of was tested in various other plant diseases, particularly in other plant pathogenic fungi and oomycets. Exemplary results are depicted in the following Table 3:

TABLE 3

In vitro antifungal activity of *Lysobacter capsici* strain AZ78

| Plant pathogenic fungi and oomycetes | Reduction of mycelial growth (%) |
|---|---|
| *Alternaria alternata* | 69% |
| *Ascochyta rabiei* | 80% |
| *Aspergillus flavus* | 18% |
| *Aspergillus niger* | 17% |
| *Aspergillus ochraceus* | 17% |
| *Botrytis cinerea* | 68% |
| *Colletotrichum gloeosporioides* | 79% |
| *Fusarium acuminatum* | 55% |
| *Fusarium avenaceum* | 27% |
| *Fusarium oxysporum* Esp. *asparagi* | 45% |
| *Fusarium oxysporum* Esp. *lycopersici* | 60% |
| *Fusarium oxysporum* Esp. *radicis-lycopersici* | 58% |
| *Fusarium sambucinum* | 70% |
| *Fusarium semitectum* | 47% |
| *Fusarium solani* | 70% |
| *Penicillium* sp. | 24% |
| *Phoma tracheiphila* | 30% |
| *Phytophthora cactorum* | 74% |
| *Phytophthora capsici* | 63% |

TABLE 3-continued

In vitro antifungal activity of *Lysobacter capsici* strain AZ78

| Plant pathogenic fungi and oomycetes | Reduction of mycelial growth (%) |
|---|---|
| *Phytophthora cinnamomi* | 72% |
| *Pythium ultimum* | 55% |
| *Rhizoctonia solani* | 81% |
| *Sclerotinia major* | 79% |
| *Sclerotinia minor* | 79% |
| *Sclerotinia sclerotiorum* | 85% |
| *Thielaviopsis basicola* | 58% |

REFERENCES

Every citation of literature herein is explicitly incorporated by reference herein in its entirety.

Arguello J M, Eren E, Gonzalez-Guerrero M. The structure and function of heavy metal transport $P_{IB}$-ATPases. Biometals 2007; 20:233-248.

Banin E, Vasil M L, Greenberg E P. Iron and *Pseudomonas aeruginosa* biofilm formation. P Natl Acad Sci USA 2005; 102:11076-11081.

Christensen P, Cook F D. *Lysobacter*, a new genus of nonfruiting, gliding bacteria with a high base ratio. Int J Syst Bacteriol 1978; 28:367-393.

Cooksey D A. Molecular mechanisms of copper resistance and accumulation in bacteria. FEMS Microbiol Rev 1994; 14:381-386.

Cooley M B, Miller W G, Mandrell R E. Colonization of *Arabidopsis thaliana* with *Salmonella enterica* and enterohemorrhagic *Escherichia coli* O157:H7 and competition by *Enterobacter asburiae*. Appl Environ Microbiol 2003; 69:4915-4926.

Dagostin S, Schaerer H J, Pertot I, Tamm L. Are there alternatives to copper for controlling grapevine downy mildew in organic viticulture? Crop Prot 2011; 30:776-788.

De la Iglesia R, Valenzuela-Heredia D, Pavissich J P, Freyhoffer S, Andrade S, Correa J A, Gonzalez B. Novel polymerase chain reaction primers for the specific detection of bacterial copper P-type ATPases gene sequences in environmental isolates and metagenomic DNA. Left Appl Microbiol 2010; 50:552-562.

De Souza J T, de Boer M, de Waard P, van Beek T A, Raaijmakers J M. Biochemical, genetic and zoosporicidal properties of cyclic lipopeptide surfactants produced by *Pseudomonas fluorescens*. App Environ Microbiol 2003; 69: 7161-7172.

Dulla G, Lindow S E. Quorum size of *Pseudomonas syringae* is small and dictated by water availability on the leaf surface. P Natl Acad Sci USA 2008; 105:3082-3087.

Elasri M O, Miller R V. Study of the response of a biofilm bacterial community to UV radiation. Appl Environ Microbiol 1999; 65:2025-2031.

EPPO. EPPO Standards PP1/31(3). Efficacy evaluation of fungicides & bactericides. 2004; 2:37-39.

Folman L B, Postma J, Van Veen J A. Ecophysiological characterization of rhizosphere bacterial communities at different root locations and plant developmental stages of cucumber grown on rockwool. Microbial Ecol 2001; 42:586-597.

Folman L B, Postma J, van Veen J A. Characterization of *Lysobacter enzymogenes* (Christensen and Cook 1978)

strain 3.1T8, a powerful antagonist of fungal diseases of cucumber. Microbiol Res 2003; 158:107-115.

Folman L B, De Klein MJEM, Postma J, van Veen J A. Production of antifungal compounds by *Lysobacter enzymogenes* strain 3.1T8 under different conditions in relation to its efficacy as a biocontrol agent of *Pythium aphanidermatum* in cucumber. Biol Control 2004; 31:145-154.

Fry W E, Goodwin S B. Resurgence of the Irish potato famine fungus. Bioscience 1997; 47:363-371.

Fu D, Beeler T J, Dunn T M. Sequence, mapping and disruption of CCC2, a gene that cross-complements the Ca(2+)-sensitive phenotype of csg1 mutants and encodes a P-type ATPase belonging to the Cu(2+)-ATPase subfamily. Yeast 1995; 11:283-292.

Ge Z, Hiratuska K, Taylor D E. Nucleotide sequence and mutational analysis indicate that two *Helicobacter pylori* genes encode a P-type ATPase and cation-binding protein associated with copper transport. Mol Microbiol 1995; 15:97-106.

Gessler C, Pertot I, Perazzolli M. *Plasmopara viticola*: a review of knowledge on downy mildew of grapevine and effective disease management. Phytopathol Mediterr 2011; 50:3-44.

Giesler L J, Yuen G Y. Evaluation of *Stenotrophomonas maltophilia* strain C3 for biocontrol of brown patch disease. Crop Prot 1998; 17:509-513.

Hayward A C, Fegan N, Fegan M, Stirling G R. *Stenotrophomonas* and *Lysobacter*: ubiquitous plant-associated gamma-proteobacteria of developing significance in applied microbiology. J App Microbiol 2010; 108:756-770.

Homma Y, Uchino H, Kanzawa K, Nakayama T, Sayama M. Suppression of sugar beet damping-off and production of antagonistic substances by strains of rhizobacteria. Ann Phytopathol Soc Jpn 1993; 59:282.

Islam M T, Hashidoko Y, Deora A, Itoi T, Tahara S. Suppression of damping-off disease in host plants by rhizoplane bacterium *Lysobacter* sp. strain SB-K88 is linked to plant colonization and antibiosis against soil-borne penosporomycetes. Appl Environ Microbiol 2005; 71:3786-3796.

Jochum C C, Osborne L E, Yuen G Y. *Fusarium* head blight biological control with *Lysobacter enzymogenes* strain C3. Biol Control 2006; 39:336-344.

Kilic-Ekici O, Yuen G Y. Induced resistance as a mechanism of biological control by *Lysobacter enzymogenes* strain C3. Phytopathology 2003; 93:1103-1110.

King E O, Ward M K, Raney D E. Two simple media for the demonstration of pyocyanin and fluorescin. J Lab Clin Med 1954; 44:301-307.

Kobayashi D Y, Yuen G Y. The role of clp-regulated factors in antagonism against *Magnaporthe poae* and biological control of summer patch disease of Kentucky bluegrass by *Lysobacter enzymogenes* C3. Can J Microbiol 2005; 51:719-723.

Leben C. Relative humidity and the survival of epiphytic bacteria with buds and leaves of cucumber plants. Phytopathology 1988; 78:179-185.

Lejon D P H, Nowak V, Bouko S, Pascault N, Mougel C, Martins J M F, Ranjard L. Fingerprinting and diversity of bacterial copA genes in response to soil types, soil organic status and copper contamination. FEMS Microbiol Ecol 2007; 61:424-437.

Lourenço J V, Maffia L A, Romeiro R D, Mizubuti E S G. Biocontrol of tomato late blight with combination of epiphytic antagonists and rhizobacteria. Biol Control 2006; 38:331-340.

Lugtenber B, Kamilova F. Plant-growth-promoting rhizobacteria. Annu Rev Microbiol 2009; 63:541-556.

Maddula VSRK, Zhang Z, Pierson E A, Pierson III L S. Quorum sensing and phenazines are involved in biofilm formation by *Pseudomonas chlororaphis* (*aureofaciens*) strain 30-84 Microbial Ecol 2006; 52:289-301.

Mizubuti E S G, Lourenço J V, Forbes G A. Management of late blight with alternative products.2007; http://www-.globalscienscebook.info/JournalsSup/images/0712/PT_1 (2)106-116o.pdf.

Morris C E, Monier J M, Jacques M A. Methods for observing microbial biofilms directly on leaf surfaces and recovering them for isolation of culturable microorganisms. Appl Environ Microbiol 1997; 63:1570-1576.

Nakayama T, Homma Y, Hashidoko Y, Mizutani J, Tahara S. Possible role of xanthobaccins produced by *Stenotrophomonas* sp. strain SB-K88 in suppression of sugar beet damping-off disease. Appl Environ Microbiol 1996; 65:4334-4339.

Ophir T, Gutnick D L. A role for exopolysaccharides in the protection of microorganisms from dessication. Appl Environ Microbiol 1994; 60:740-745.

Park J H, Kim R, Aslam Z, Jeon C O, Chung Y R. *Lysobacter capsici* sp. nov., with antimicrobial activity, isolated from the rhizosphere of pepper, and emended description of the genus *Lysobacter*. Int J Syst Bacteriol 2008; 58:387-392.

Pavissich J P, Macarena S, Gonzalez B. Sulfate reduction, molecular diversity, and copper amendments effects in bacterial communities enriched from sediments exposed to copper mining residues. Environ Toxicol Chem 2010; 29:256-264.

Perrot F, Jouenne T, Feuilloley M, Vaudry H, Junter G-A. Gel immobilization improves survival of *Escherichia coli* under temperature stress in nutrient-poor natural water. Water Res 1998; 32:3521-3526.

Petersen C, Møller L B. Control of copper homeostasis in *Escherichia coli* by a P-type ATPase, CopA and a MerR-like transcriptional activator, CopR. Gene 2000; 261:289-298.

Postma J, Schilder M T, Bloem J, van Leeuwen-Haagsm W K. Soil suppressiveness and functional diversity of the soil microflora in organic farming systems. Soil Biol Biochem 2008; 40:2394-2406.

Puopolo G, Raio A, Zoina A. Identification and characterization of *Lysobacter capsici* strain PG4: a new health promoting rhizobacterium. J Plant Path 2010; 92:159-166.

Rensing C, Grass G. *Escherichia coli* mechanisms of copper homeostasis in a change environment. FEMS Microbiol Rev 2003; 27:197-213.

Ritchie D F, Dittanpongpitch V. Copper- and streptomycin-resistant strains and host differentiated races of *Xanthomonas campestris* pv. *vesicatoria* in North Carolina. Plant Dis 1991; 75:733-736.

Rondon M R, Borlee B R, Brady S F, Gross J A, Guenthner B J, Manske B, Raffel S J, Weisz J B, Vincelli P, Clardy J, Goodman R M, Handelsmanet J. Biocontrol and root colonization by the gliding bacterium *Lysobacter antibioticus*. Phytopathology 1999; 89:S66.

Stockwell V O, Loper J E. The sigma factor RpoS is required for stress tolerance and environmental fitness of *Pseudomonas fluorescens* Pf-5. Microbiology 2005; 151: 3001-3009.

Stockwell V O, Hockett K, Loper J E. Role of RpoS in stress tolerance and environmental fitness of the phyllosphere bacterium *Pseudomonas fluorescens* strain 122. Phytopathology 2009; 99:689-695.

Sundin G W, Jacobs J L. Ultraviole radiation (UVR) sensitivity analysis and UVR survival strategies of a bacterial community from the phyllosphere of field-grown peanut (*Arachis* hypogeae L.). Microb Ecol 1999; 38:27-38.

Tilcher R, Wolf G A, Brendel G. Effects of microbial antagonists on leaf infestation, sporangia germination and zoospore behaviour of *Plasmopara viticola* (Berk. & Curtis) Berl. & de Toni. Mededelingen—Faculteit Landbouwkundige en Toegepaste Biologische Wetenschappen, Universiteit Gent 1994; 59:919-929.

Tilcher R, Schmidt C, Lorenz D, Wolf G A. About the use of antagonistic bacteria and fungi. In: Boos M, editor. 10*th International Conference on Cultivation Technique and Phytopathological Problems in Organic Fruit-Growing and Viticulture. Proceedings to the Conference from* 4*th to* 7*th Feb.* 2002 *at Weinsberg/Germany* 2002; p. 142-145.

Tomaras A P, Dorsey C W, Edelmann R E, Actis L A. Attachment to and biofilm formation on abiotic surfaces by *Acinetobacter baumannii*: involvement of a novel chaperone-usher pili assembly system. Microbiology 2003; 149:3473-3484.

Wilson M, Hirano S S, Lindow S E. Location and survival of leaf-associated bacteria in relation to pathogenicity and potential for growth within the leaf. Appl Environ Microbiol 1999; 65:1435-1443.

Wong F P, Burr H N, Wilcox W F. Heterothallism in *Plasmopara viticola*. Plant Pathol 2001; 50:427-432.

Zakharchenko N S, Kochetkov V V, Buryanov Y I, Boronin A M. Effect of rhizosphere bacteria *Pseudomonas aureofaciens* on the resistance of micropropagated plants to phytopathogens. Appl Biochem Microbiol 2011; 47:661-666.

The invention claimed is:

1. A plant protection product, comprising a bacterial strain selected from the group consisting of:

i) *Lysobacter capsici* AZ78 ii) a strain obtainable from deposit CBS 134400 iii) a strain comprising a nucleic acid sequence that has at least 99% identity to a sequence selected from the group consisting of SEQ ID NOs: 6-13;

or at least one bacterium or bacterial preparation thereof; and further comprising a copper compound.

2. The plant protection product according to claim 1, wherein said plant protection product is a plant protection product against a plant pathogenic fungus or a plant pathogenic oomycete.

3. A method of preventing or treating a plant disease, comprising a step of contacting at least one plant with a bacterial strain, selected from the group consisting of i) *Lysobacter capsici* AZ78, ii) a strain obtainable from deposit CBS 134400, iii) a strain comprising a nucleic acid sequence that has at least 99% identity to a sequence selected from the group consisting of SEQ ID NOs: 6-13;

or with a bacterium or bacterial composition thereof, or with a plant protection product comprising the said bacterial strain or bacterium or bacterial composition, wherein said method additionally comprises a step of contacting said plant with a composition comprising copper.

4. The method according to claim 3, wherein said composition comprising copper is a copper plant protection product.

5. The plant protection product of claim 1, wherein the said plant protection product is a plant protection product against a plant pathogenic fungus or a plant pathogenic oomycete, selected from the group consisting of *Alternaria alternata, Ascochyta rabiei, Aspergillus flavus, Aspergillus niger, Aspergillus ochraceus, Botrytis cinerea, Colletotrichum gloeosporioides, Fusarium acuminatum, Fusarium avenaceum, Fusarium oxysporum* f. sp. *asparagi, Fusarium oxysporum* f. sp. *lycopersici, Fusarium oxysporum* f. sp. *radicis-lycopersici, Fusarium sambucinum, Fusarium semitectum, Fusarium solani, Penicillium* sp., *Phoma tracheiphila, Phytophthora cactorum, Phytophthora capsici, Phytophthora cinnamomi, Phytophthora infestans, Plasmopara viticola, Pythium ultimum, Rhizoctonia solani, Sclerotinia maior, Sclerotinia minor, Sclerotinia sclerotiorum*, and *Thielaviopsis basicola.*

6. The plant protection product of claim 1, wherein the said plant protection product is a plant protection product against a plant pathogenic oomycete, wherein said plant pathogenic oomycete causes grapevine downy mildew or tomato late blight.

7. The plant protection product of claim 1, wherein the said copper compound is selected from the group consisting of copper hydroxide, copper oxychloride, copper sulphate, tribasic copper sulphate, and copper octanoate.

8. The method of claim 4, wherein said composition comprising copper comprises at least one copper compound selected from the group consisting of copper hydroxide, copper oxychloride, copper sulphate, tribasic copper sulphate, and copper octanoate.

9. The method of claim 4, wherein said plant disease is a fungal disease or an oomycete disease.

10. The method of claim 9, wherein said plant disease is caused by a fungus or an oomycete selected from the group consisting of *Alternaria alternata, Ascochyta rabiei, Aspergillus flavus, Aspergillus niger, Aspergillus ochraceus, Botrytis cinerea, Colletotrichum gloeosporioides, Fusarium acuminatum, Fusarium avenaceum, Fusarium oxysporum* f. sp. *asparagi, Fusarium oxysporum* f. sp. *lycopersici, Fusarium oxysporum* f. sp. *radicis-lycopersici, Fusarium sambucinum, Fusarium semitectum, Fusarium solani, Penicillium* sp., *Phoma tracheiphila, Phytophthora cactorum, Phytophthora capsici, Phytophthora cinnamomi, Phytophthora infestans, Plasmopara viticola, Pythium ultimum, Rhizoctonia solani, Sclerotinia maior, Sclerotinia minor, Sclerotinia sclerotiorum*, and *Thielaviopsis basicola.*

11. The method of claim 9, wherein said plant disease is grapevine downy mildew or tomato late blight.

* * * * *

UNITED STATES PATENT AND TRADEMARK OFFICE
CERTIFICATE OF CORRECTION

PATENT NO. : 9,756,863 B2
APPLICATION NO. : 14/785541
DATED : September 12, 2017
INVENTOR(S) : Gerardo Puopolo et al.

It is certified that error appears in the above-identified patent and that said Letters Patent is hereby corrected as shown below:

On the Title Page

In Puopolo, replace "ac tivity" with --activity--;
In (74), replace "Bicker-Brady" with --Bieker-Brady--.

In the Specification

Column 2, Line 14, replace "*A. chloclioides*" with --*A. cochlioides*--;
Line 42, replace "*Phythopthera*" with --*Phytophthora*--.

Column 5, Line 6, replace "bio formulation" with --bioformulation--;
Line 32, replace "an" with --a--.

Column 6, Line 6, replace "as well as and" with --as well as--;
Line 67, replace "invention"." with --invention."--.

Column 7, Line 11, replace "bio film" with --biofilm--.

Column 8, Lines 59, replace "Quichimica Masse" with --Química Massó--.

Column 13, Line 45, replace "oxycloride" with --oxychloride--;
Line 52, replace "oxycloride" with --oxychloride--.

Column 18, Line 29, replace "according items" with --according to items--.

Column 20, Line 38, replace "a" with --an--;
Line 63, delete "to".

Column 24, Line 25, replace "*malthophdia*" with --*maltophilia*--.

Signed and Sealed this
Fifth Day of February, 2019

Andrei Iancu
*Director of the United States Patent and Trademark Office*

Column 27, Line 15, replace “Arguelo” with --Arguello--;
Line 17-18, replace “malthophilia” with --maltophilia--;
Line 21, replace “2003)” with --2003).--.

Column 29, Line 40, delete “of”;
Line 42, replace “oomycets” with --oomycetes--.

Column 32, Line 26, replace “dessication” with --desiccation--;
Line 47, replace “Leeuwen-Haagsm” with --Leeuwen-Haagsma--;
Line 59, replace “Dittanpongpitch” with --Dittapongpitch--;
Line 65, replace “Handelsmanet” with --Handelsman--.

Column 33, Line 9, replace “Ultraviole” with --Ultraviolet--.